(12) United States Patent
Doherty et al.

(10) Patent No.: US 7,528,163 B2
(45) Date of Patent: May 5, 2009

(54) OPHTHALMIC COMPOSITIONS FOR TREATING OCULAR HYPERTENSION

(75) Inventors: James B. Doherty, Montvale, NJ (US); Meng-Hsin Chen, Westfield, NJ (US); Luping Liu, Plainsboro, NJ (US); Swaminathan R. Natarajan, Scotch Plains, NJ (US); Dong-Ming Shen, Edison, NJ (US); Robert M. Tynebor, Woodbridge, NJ (US)

(73) Assignee: Merck & Co. Inc., Rahway, NJ (US)

( * ) Notice: Subject to any disclaimer, the term of this patent is extended or adjusted under 35 U.S.C. 154(b) by 530 days.

(21) Appl. No.: 10/530,840

(22) PCT Filed: Nov. 4, 2003

(86) PCT No.: PCT/US03/34959

§ 371 (c)(1),
(2), (4) Date: Apr. 8, 2005

(87) PCT Pub. No.: WO2004/043354

PCT Pub. Date: May 27, 2004

(65) Prior Publication Data

US 2006/0020000 A1  Jan. 26, 2006

Related U.S. Application Data

(60) Provisional application No. 60/500,094, filed on Sep. 4, 2003, provisional application No. 60/424,790, filed on Nov. 8, 2002.

(51) Int. Cl.
*A61K 31/415* (2006.01)
*C07D 231/56* (2006.01)

(52) U.S. Cl. ..................... 514/406; 548/362.5
(58) Field of Classification Search .............. 548/362.5; 514/406
See application file for complete search history.

(56) References Cited

U.S. PATENT DOCUMENTS

| | | | |
|---|---|---|---|
| 4,690,931 | A | 9/1987 | Wick et al. |
| 5,151,444 | A | 9/1992 | Ueno et al. |
| 5,296,504 | A | 3/1994 | Stjernschantz et al. |
| 5,352,708 | A | 10/1994 | Woodward et al. |
| 5,422,368 | A | 6/1995 | Stjernschantz et al. |
| 5,573,758 | A | 11/1996 | Adorante et al. |
| 5,889,052 | A | 3/1999 | Klimko et al. |
| 5,925,342 | A | 7/1999 | Adorante et al. |
| 2007/0027188 | A1* | 2/2007 | Chen et al. .................. 514/338 |
| 2008/0032951 | A1* | 2/2008 | Doherty et al. ............... 514/81 |

FOREIGN PATENT DOCUMENTS

| | | |
|---|---|---|
| EP | 058 923 | 9/1993 |
| EP | 1114816 | 9/1999 |
| EP | 1 479 675 | 11/2001 |
| JP | 50157363 | 12/1975 |
| WO | WO 94/13275 A1 | 6/1994 |
| WO | WO 94/28900 A1 | 6/1994 |
| WO | WO 96/33719 A1 | 10/1996 |
| WO | WO 89/10757 A1 | 11/1998 |
| WO | WO 01/70702 A1 | 11/2000 |
| WO | WO 01/46140 A1 | 6/2001 |
| WO | WO 01/70701 | 9/2001 |
| WO | WO 01/72268 A1 | 10/2001 |
| WO | WO 02/24647 A1 | 3/2002 |
| WO | WO 02/42268 A2 | 5/2002 |
| WO | WO 2005/025568 | 3/2005 |

OTHER PUBLICATIONS

S. R. Moore et al., "Development and Aging of Cell Topography in the Human Retinal Pigment Epithelium", 1997, pp. 2016-2026, vol. 38, No. 10, Investigative Ophthalmology & Visual Science.

E. L. Eliel et al., "Chirality in Molecules Devoid of Chiral Centers", 1994, pp. 1119-1190, Stereochemistry of Organic Compounds.

S. M. Berge et al., "Pharmaceutical Salts", 1977, pp. 1-19, vol. 66, No. 1, J. of Pharmaceutical Sciences.

H. Eto et al., "New Antifungal 1,2,4-Triazoles with Difluoro (heteroaryl)methyl Moiety", 2000, pp. 982-990, vol. 48, No. 7, Pharmaceutical Society of Japan.

Smith et al., "Carbonylation of Various Organolithium Reagents. A Novel Approach to Heterocycles via Intramolecular Trapping of Aromatic Acyllithiums", 1999, pp. 2299-2303, J. Chem. Soc. Perken Trans I.

F. Piozzi et al., Azione dell'acido Nitroso su Alcuni Alchilindoli: Una Nuova Sintesi Indazolica., 1959, pp. 638-653, vol. 89, Gazz. Chim ital.

M. Hanner et al., "the Beta Subunit of the High Conductance Calcium-Activated Potassium Channel", 1998, pp. 16289-16296, vol. 273, No. 26, J. of Biological Chemistry.

P. M. Vassallo et al., "Expression of Na, K-ATPase Alpha Subunit Isoforms in the Human Ciliary Body and Cultured Ciliary Epithelial Cells", 1989, vol. 141, pp. 243-252, J. of Cellular Physiology.

Masaharu et al., "Indazolecarboylic Acid Derivatives", Database Caplus; Chemical Abstracts , Database Accession No. 1976:523913.

M. Takayama et al, "Indazolecbarboxylic Acid Derivatives", 1975,Chemical Abstract No. 85:123913, Equivalent to JP 50157363.

* cited by examiner

Primary Examiner—Rebecca L Anderson
(74) Attorney, Agent, or Firm—Sylvia A. Ayler; William Krovatin

(57) ABSTRACT

This invention relates to potent potassium channel blocker compounds of Formula I or a formulation thereof for the treatment of glaucoma and other conditions which leads to elevated intraocular pressure in the eye of a patient. This invention also relates to the use of such compounds to provide a neuroprotective effect to the eye of mammalian species, particularly humans.

7 Claims, No Drawings

OPHTHALMIC COMPOSITIONS FOR TREATING OCULAR HYPERTENSION

CROSS REFERENCE TO RELATED APPLICATIONS

This application is the National Stage of International Application No. PCT/US03/34959 filed on Nov. 4, 2003 which claims the benefit under 35 U.S.C. 119(e) of U.S. Provisional Applications Ser. No. 60/424,790 and 60/500,094 filed Nov. 8, 2002 and Sep. 4, 2003.

BACKGROUND OF THE INVENTION

Glaucoma is a degenerative disease of the eye wherein the intraocular pressure is too high to permit normal eye function. As a result, damage may occur to the optic nerve head and result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by the majority of ophthalmologists to represent merely the earliest phase in the onset of glaucoma.

There are several therapies for treating glaucoma and elevated intraocular pressure, but the efficacy and the side effect profiles of these agents are not ideal. Recently potassium channel blockers were found to reduce intraocular pressure in the eye and therefore provide yet one more approach to the treatment of ocular hypertension and the degenerative ocular conditions related thereto. Blockage of potassium channels can diminish fluid secretion, and under some circumstances, increase smooth muscle contraction and would be expected to lower IOP and have neuroprotective effects in the eye. (see U.S. Pat. Nos. 5,573,758 and 5,925,342; Moore, et al., Invest. Ophthalmol. Vis. Sci 38, 1997; WO 89/10757, WO94/28900, and WO 96/33719).

SUMMARY OF THE INVENTION

This invention relates to the use of potent potassium channel blockers or a formulation thereof in the treatment of glaucoma and other conditions which are related to elevated intraocular pressure in the eye of a patient. This invention also relates to the use of such compounds to provide a neuroprotective effect to the eye of mammalian species, particularly humans. More particularly this invention relates to the treatment of glaucoma and/or ocular hypertension (elevated intraocular pressure) using novel indazole compounds having the structural formula I:

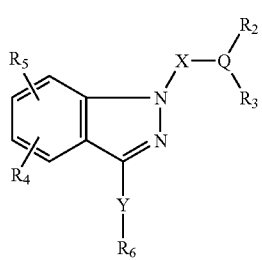

Formula I or a pharmaceutically acceptable salt, enantiomer, diastereomer or mixture thereof: wherein, R represents hydrogen, or $C_{1-6}$ alkyl;
X represents —$(CHR_7)_p$—, or —$(CHR_7)_pCO$—;
Y represents —$CO(CH_2)_n$—, $CH_2$, or —$CH(OR)$—;
Q represents N, or O, wherein $R_2$ is absent when Q is O;
$R_w$ represents H, $C_{1-6}$ alkyl, —$C(O)C_{1-6}$ alkyl, —$C(O)OC_{1-6}$ alkyl, —$SO_2N(R)_2$, —$SO_2C_{1-6}$ alkyl, —$SO_2C_{6-10}$ aryl, $NO_2$, CN or —$CON(R)_2$;
$R_2$ represents hydrogen, $C_{1-10}$ alkyl, OH, $C_{2-6}$ alkenyl, $C_{1-6}$ alkylSR, —$(CH_2)_nO(CH_2)_mOR$, —$(CH_2)_nC_{1-6}$ alkoxy, —$(CH_2)_nC_{3-8}$ cycloalkyl, —$(CH_2)_nC_{3-10}$ heterocyclyl, —$N(R)_2$, —COOR, or —$(CH_2)_nC_{6-10}$ aryl, said alkyl, heterocyclyl, or aryl optionally substituted with 1-3 groups selected from $R^a$;
$R_3$ represents hydrogen, $C_{1-10}$ alkyl, —$(CH_2)_nC_{3-8}$ cycloalkyl, —$(CH_2)_nC_{3-10}$ heterocyclyl, —$(CH_2)_n$ COOR, —$(CH_2)_nC_{6-10}$ aryl, —$(CH_2)_nNHR_8$, —$(CH_2)_nN(R)_2$, —$(CH_2)_nN(R_8)_2$, —$(CH_2)_nNHCOOR$, —$(CH_2)_nN(R_8)CO_2R$, —$(CH_2)_nN(R_8)COR$, —$(CH_2)_nNHCOR$, —$(CH_2)_nCONH(R_8)$, aryl, —$(CH_2)_nC_{1-6}$ alkoxy, $CF_3$, $(CH_2)_nSO_2R$, —$(CH_2)_nSO_2N(R)_2$, —$(CH_2)_nCON(R)_2$, —$(CH_2)_nCONHC(R)_3$, —$(CH_2)_nCONHC(R)_2CO_2R$, —$(CH_2)_nCOR_8$, nitro, cyano or halogen, said alkyl, alkoxy, heterocyclyl, or aryl optionally substituted with 1-3 groups of $R^a$;
or, when Q is N, $R_2$ and $R_3$ taken together with the intervening N atom form a 4-10 membered heterocyclic carbon ring optionally interrupted by 1-2 atoms of O, S, C(O) or NR, and optionally having 1-4 double bonds, and optionally substituted by 1-3 groups selected from $R^a$;
$R_4$ and $R_5$ independently represent hydrogen, $C_{1-6}$ alkoxy, OH, $C_{1-6}$ alkyl, $SO_qC_{1-6}$ alkyl, $COC_{1-6}$ alkyl, COOR, $SO_3H$, —$O(CH_2)_nN(R)_2$, —$O(CH_2)_nCO_2R$, —OPO$(OH)_2$, $CF_3$, $OCF_3$, —$N(R)_2$, nitro, cyano, $C_{1-6}$ alkylamino, or halogen; and
$R_6$ represents hydrogen, $C_{1-10}$ alkyl, —$(CH_2)_nC_{6-10}$ aryl, $NR_cR_d$, —$NR(CH_2)_nC_{6-10}$ aryl, —$N((CH_2)_nC_{6-10}$ aryl$)_2$, —$(CH_2)_nC_{3-10}$ heterocyclyl, —$NR(CH_2)_nC_{3-10}$ heterocyclyl, —$N((CH_2)_nC_{3-10}$ heterocyclyl$)_2$, $(C_{6-10}$ aryl)O—, —$(CH_2)_nC_{3-8}$ cycloalkyl, —COOR, —$C(O)CO_2R$, said aryl, heterocyclyl and alkyl optionally substituted with 1-3 groups selected from $R^a$, wherein the $R^a(s)$ can be attached to any carbon atom or heteroatom selected from N and S;
$R_c$ and $R_d$ independently represent H, $C_{1-6}$ alkyl, $C_{2-6}$ alkenyl, $C_{1-6}$ alkylSR, —$(CH_2)_nO(CH_2)_mOR$, —$(CH_2)_nC_{1-6}$ alkoxy, —$(CH_2)_nC_{3-8}$ cycloalkyl;
or $R_c$ and $R_d$ taken together with the intervening N atom form a 4-10 membered heterocyclic carbon ring optionally interrupted by 1-2 atoms of O, S, C(O) or NR, and optionally having 14 double bonds, and optionally substituted by 1-3 groups selected from $R^a$;
$R_7$ represents hydrogen, $C_{1-6}$ alkyl, —$(CH_2)_nCOOR$ or —$(CH_2)_nN(R)_2$,
$R_8$ represents —$(CH_2)_nC_{3-8}$ cycloalkyl, —$(CH_2)_{n\,3}$-10 heterocyclyl, $C_{1-6}$ alkoxy—or $(CH_2)_nC_{6-10}$ aryl said heterocyclyl, or aryl optionally substituted with 1-3 groups selected from $R^a$;
$R^a$ represents F, Cl, Br, I, $CF_3$, $N(R)_2$, $NO_2$, CN, —O—, —$COR_8$, —$CONHR_8$, —$CON(R_8)_2$, —$O(CH_2)_nCOOR$, —$NH(CH_2)_nOR$, —COOR, —$OCF_3$, $CF_2CH_2OR$, —NHCOR, —$SO_2R$, —$SO_2NR_2$, —SR, $(C_1-C_6$ alkyl)O—, —$(CH_2)_nO(CH_2)_mOR$, —$O(CH_2)_nO(CH_2)_mOR$, —$(CH_2)_n$ $C_{1-6}$ alkoxy, (aryl)O—, —$(CH_2)_nOH$, $(C_1-C_6$ alkyl)S(O)$_m$—, $H_2N$—CN—, $(C_1-C_6$ alkyl)C(O)—, $(C_1$-$C_6$ alkyl)OC(O)NH—, —$(C_1$-$C_6$ alkyl)NR$_w$$(CH_2)_nC_{3-10}$ heterocyclyl-$R_w$, —$(C_1$-$C_6$ alkyl)O$(CH_2)_nC_{3-10}$ heterocyclyl-$R_w$, —$(C_1$-$C_6$ alkyl)S$(CH_2)_nC_{3-10}$ heterocyclyl-$R_w$, —$(C_1$-$C_6$ alkyl)-$C_{3-10}$ heterocyclyl-$R_w$, —$(CH_2)_n$-$Z^1$-C (=Z²)N(R)₂, —(C₂₋₆ alkenyl)NR_w(CH₂)_nC₃₋₁₀ heterocyclyl-R_w, —(C₂₋₆ alkenyl)O(CH₂)_nC₃₋₁₀ heterocyclyl-R_w, —(C₂₋₆ alkenyl)S(CH₂)_nC₃₋₁₀ heterocyclyl-R_w, —(C₂₋₆ alkenyl)-C₃₋₁₀ heterocyclyl-R_w, —(C₂₋₆ alkenyl)-Z¹-C(=Z²)N(R)₂, —(CH₂)_nSO₂R, —(CH₂)_nSO₃H, —(CH₂)_nPO(OR)₂, C₃₋₁₀cycloalkyl, C₆₋₁₀ aryl, C₃₋₁₀ heterocyclyl, C₂₋₆ alkenyl, and C₁-C₁₀ alkyl, said alkyl, alkenyl, alkoxy, heterocyclyl and aryl optionally substituted with 1-3 groups selected from C₁-C₆ alkyl, halogen, CN, NO₂, —(CH₂)_nOH, CON(R)₂ and COOR;

$Z^1$ and $Z^2$ independently represents NR_w, O, CH₂, or S;

m is 0-3;

n is 0-3;

p is 0-3 and q is 0-2.

This and other aspects of the invention will be realized upon inspection of the invention as a whole.

DETAILED DESCRIPTION OF THE INVENTION

The present invention is directed to novel potassium channel blockers of Formula I. It also relates to a method for decreasing elevated intraocular pressure or treating glaucoma by administration, preferably topical or intra-camaral administration, of a composition containing a potassium channel blocker of Formula I described hereinabove and a pharmaceutically acceptable carrier.

In an embodiment of the instant compounds are those compounds where p is 1-3.

One embodiment of this invention is realized when Y is —CO(CH₂)_n and all other variables are as originally described. A subembodiment of this invention is realized when n is 0.

Another embodiment of this invention is realized when Y is CH(OR) and all other variables are as originally described.

Still another embodiment of this invention is realized when Q is N and all other variables are as originally described.

Still another embodiment of this invention is realized when Q is O, wherein R₂ is absent when Q is O and all other variables are as originally described.

In another embodiment R_w is selected from H, C₁₋₆ alkyl, —C(O)C₁₋₁₆ alkyl and —C(O)N(R)₂ and all other variables are as originally described.

In another embodiment X is —(CHR₇)_p—, p is 1-3 and all other variables are as originally described.

In another embodiment X is —(CHR₇)_pCO—, p is 1-3 and all other variables are as originally described.

Still another embodiment of this invention is realized when R₆ is (CH₂)_nC₆₋₁₀ aryl, (CH₂)_nC₃₋₁₀ heterocyclyl, NR_cR_d, or (CH₂)_nC₃₋₈ cycloalkyl, said aryl, heterocyclyl and cycloalkyl optionally substituted with 1 to 3 groups of R^a, and all other variables are as originally described.

Yet another embodiment of this invention is realized when R₇ is hydrogen or Cl 6 alkyl, and all other variables are as originally described.

Yet another embodiment of this invention is realized when Y is —CO(CH₂)_n, and Q is N. A sub-embodiment of this invention is realized when n is 0.

Still another embodiment of this invention is realized when Y is —CO(CH₂)_n, Q is N, R₂ is hydrogen, C₁₋₁₀ alkyl or C₁₋₆ alkylOH and R₃ is C₁₋₁₀ alkyl or (CH₂)_nC₃₋₁₀ heterocyclyl, said heterocyclyl optionally substituted with 1 to 3 groups of R^a.

Still another embodiment of this invention is realized when Y is —CO(CH₂)_n, Q is N, and R₂ and R₃ taken together with the intervening N atom form a 410 membered heterocyclic carbon ring optionally interrupted by 1-2 atoms of O, S, C(O) or NR, and optionally having 1-4 double bonds, and optionally substituted by 1-3 groups selected from R^a Another embodiment of the instant invention is realized when R^a is selected from F, Cl, Br, I, CF₃, N(R)₂, NO₂, CN, —O—, —CONHR₈, —CON(R₈)₂, —O(CH₂)_nCOOR, —NH(CH₂)_nOR, —COOR, —OCF₃, CF₂CH₂OR, —NHCOR, —SO₂R, —SO₂NR₂, —SR, (C₁-C₆ alkyl)O—, —(CH₂)_nO(CH₂)_mOR, —(CH₂)_nC₁₋₆ alkoxy, (aryl)O—, —(CH₂)_nOH, (C₁-C₆ alkyl)S(O)_m—, H₂N—C(NH)—, (C₁-C₆ alkyl)C(O)—, —(CH₂)_nPO(OR)₂, C₂₋₆ alkenyl, and C₁-C₁₀ alkyl, said alkyl and alkenyl, optionally substituted with 1-3 groups selected from C₁-C₆ alkyl, and COOR.

Examples of compounds to be used in this invention are found in Tables 1 and 4:

TABLE 1

[Indazole scaffold structure with R₁ at 6-position, R₂-CH< at 3-position bearing an oxygen, and N-CH₂-C(=O)-R₃ at N1-position]

| R1 | R2 | R3 |
|---|---|---|
| H | Phenyl | —CH₂CH₂N(CH₂CH₂CH₃)₂ (di-n-propylaminoethyl-type) |
| H | Phenyl | —CH₂CH₂N-linked 5-thiazolyl |
| H | Phenyl | —CH₂N(CH₂CH₂CH₃)₂ |
| H | Phenyl | 2-(HN)-thiazole linkage |
| H | Phenyl | —CH₂CH₂N-linked 2-thiazolyl |
| H | Phenyl | —CH₂CH₂NH-cyclohexyl |
| H | Phenyl | —CH₂CH₂N(CH₂CH₃)(CH₂CH₂CH₃) |
| OMe | Phenyl | —CH₂N(CH₂CH₃)(CH₂CH₂CH₃) (attachment point shown) |
| OMe | Phenyl | —CH₂CH₂NH-cyclohexyl |

TABLE 1-continued
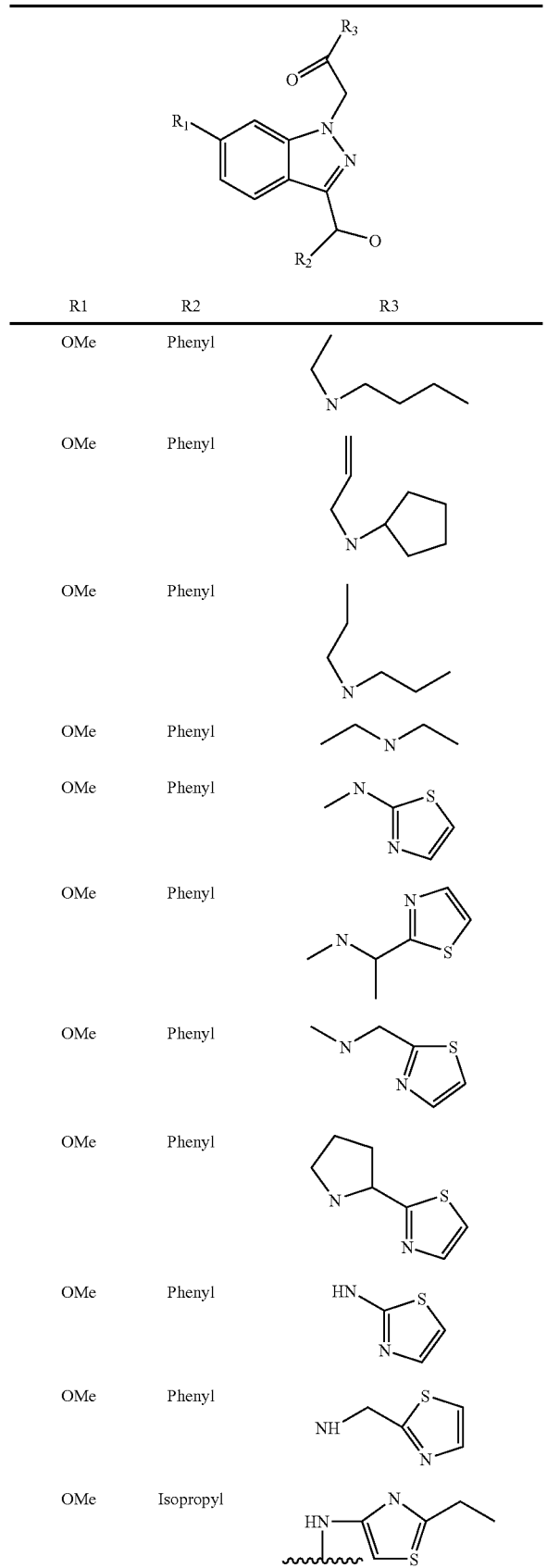
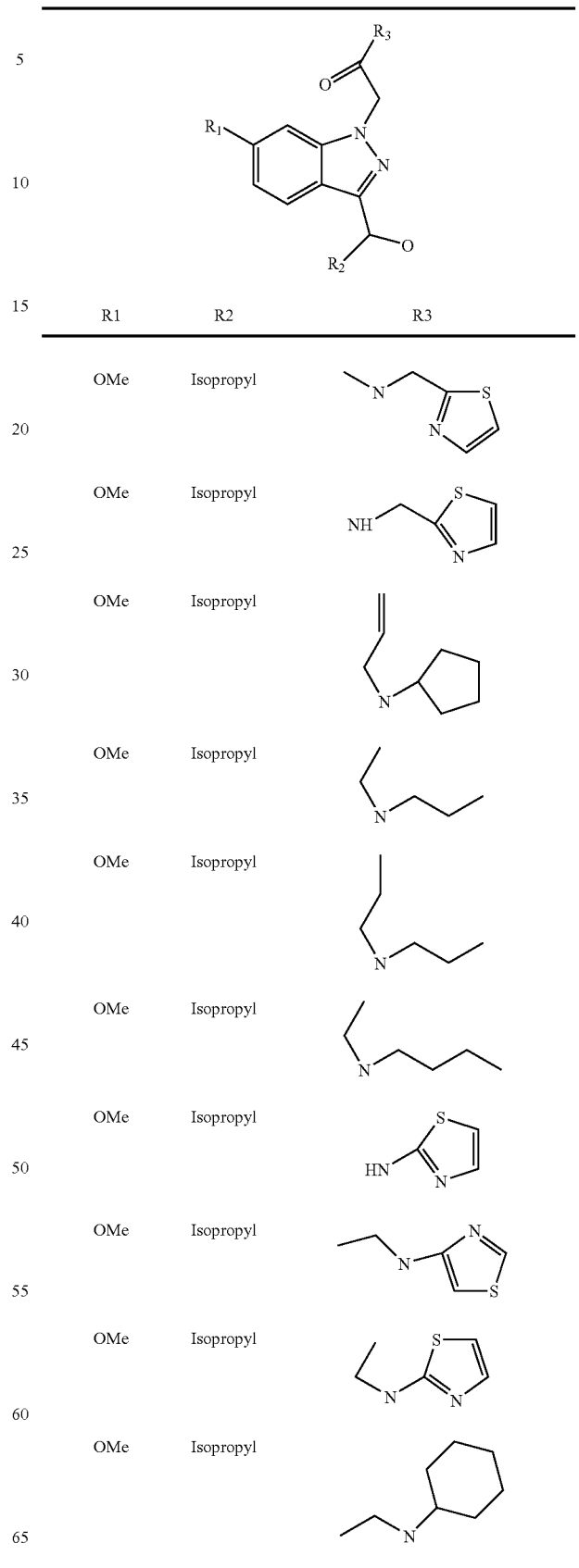

TABLE 1-continued
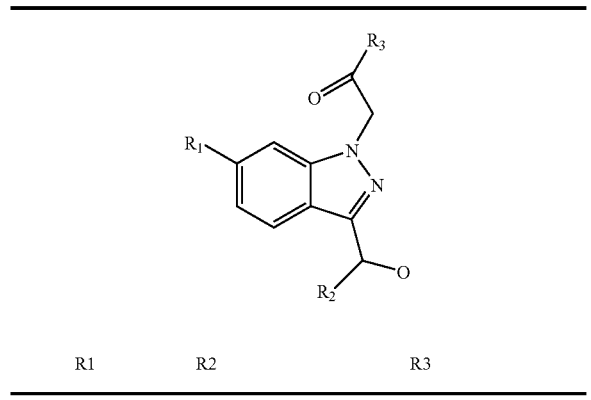
| R1 | R2 | R3 |
|---|---|---|
| OMe | Isopropyl | 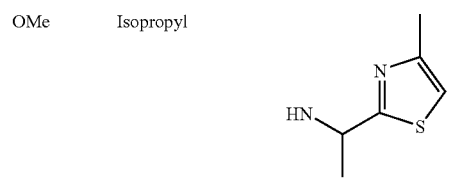 |
| OMe | Isopropyl | 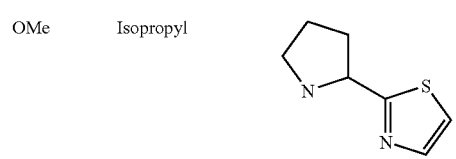 |
TABLE 2
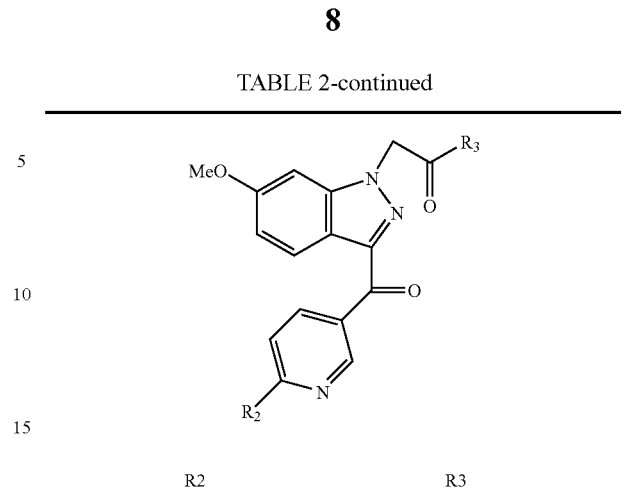
TABLE 2-continued
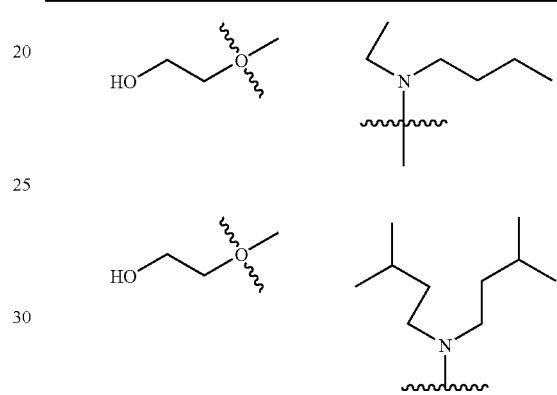
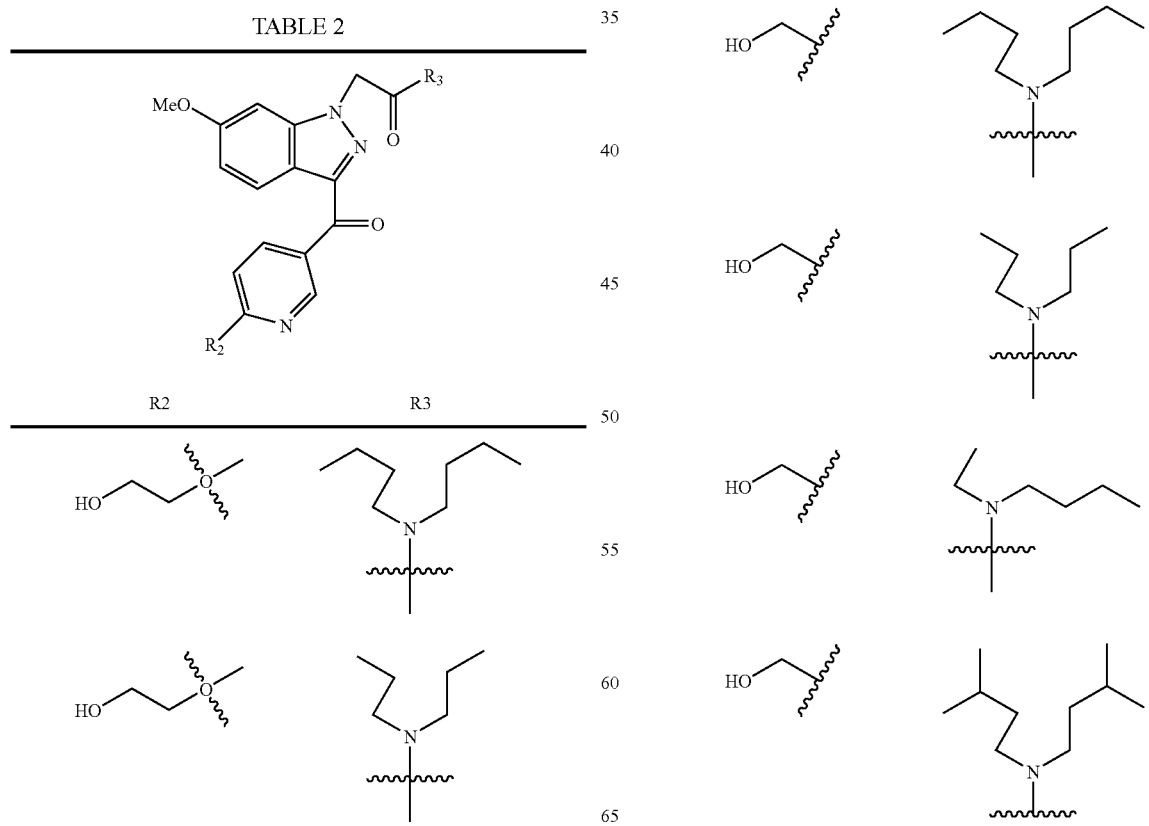

TABLE 2-continued
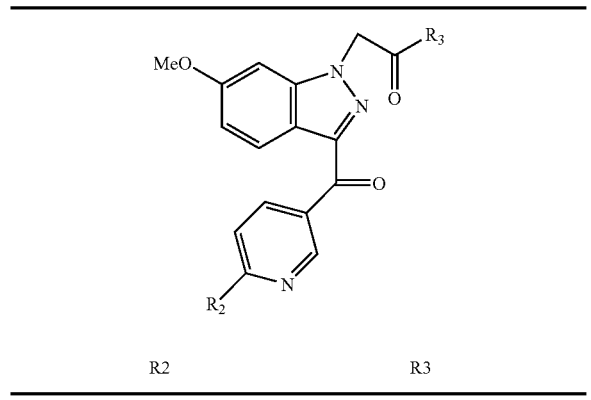
| R2 | R3 |
|---|---|
| 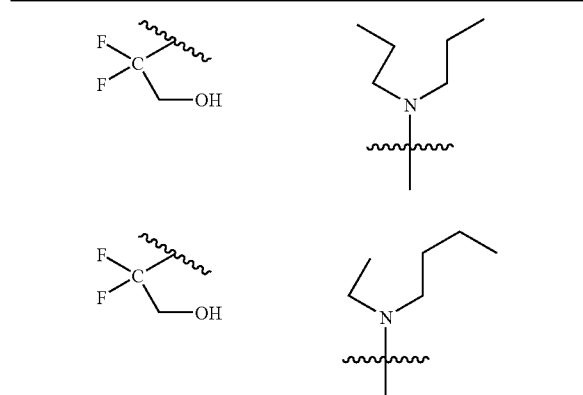 | |
| 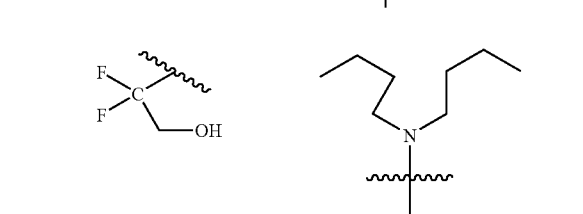 | |
| 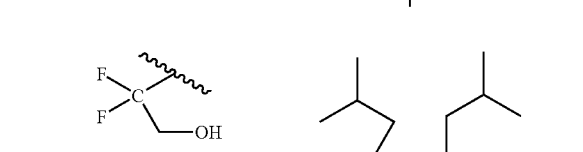 | |
| 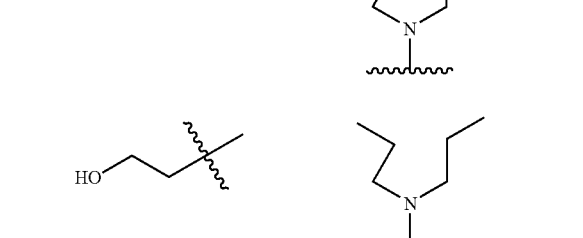 | |
| 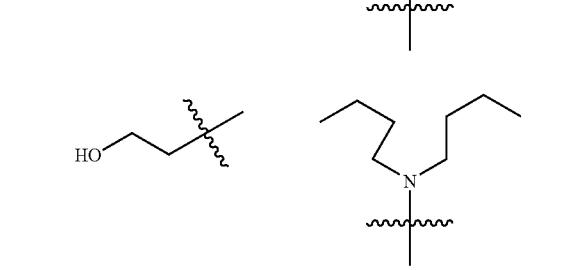 | |
TABLE 2-continued
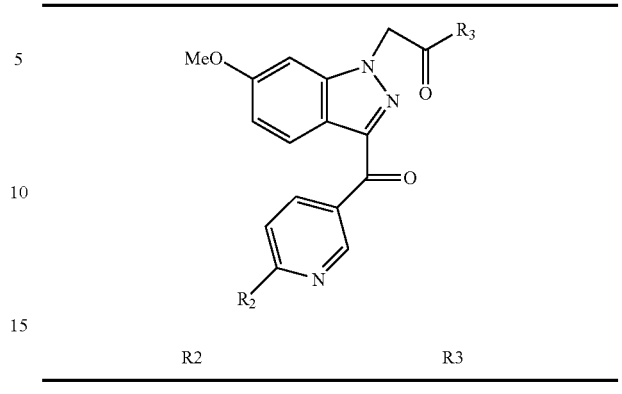
| R2 | R3 |
|---|---|
| 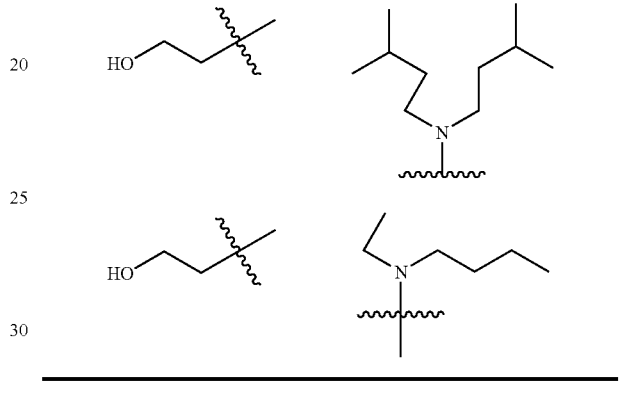 | |
TABLE 3
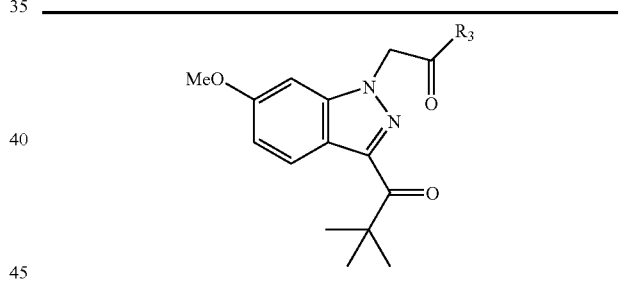
| R3 |
|---|
| 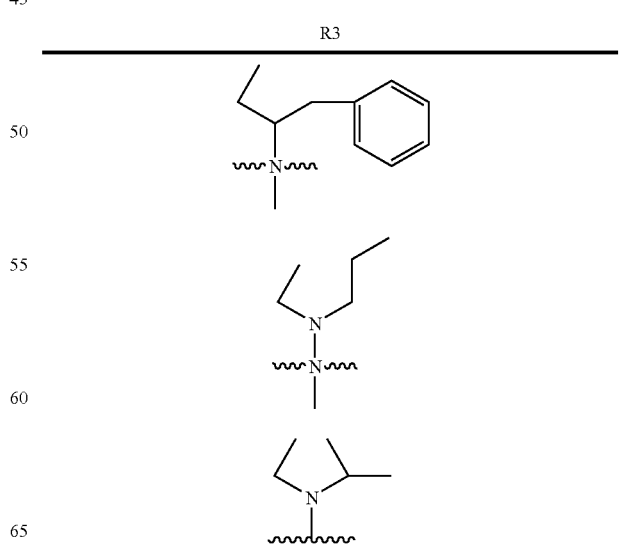 |

TABLE 3-continued
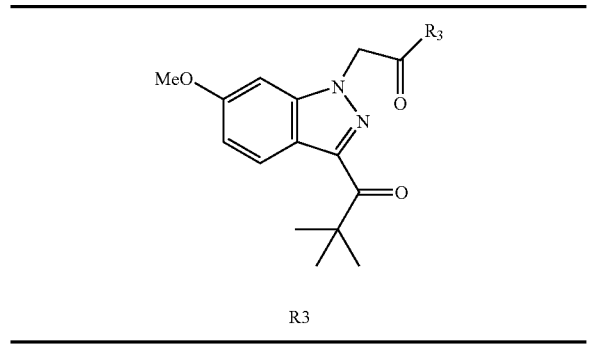
R3
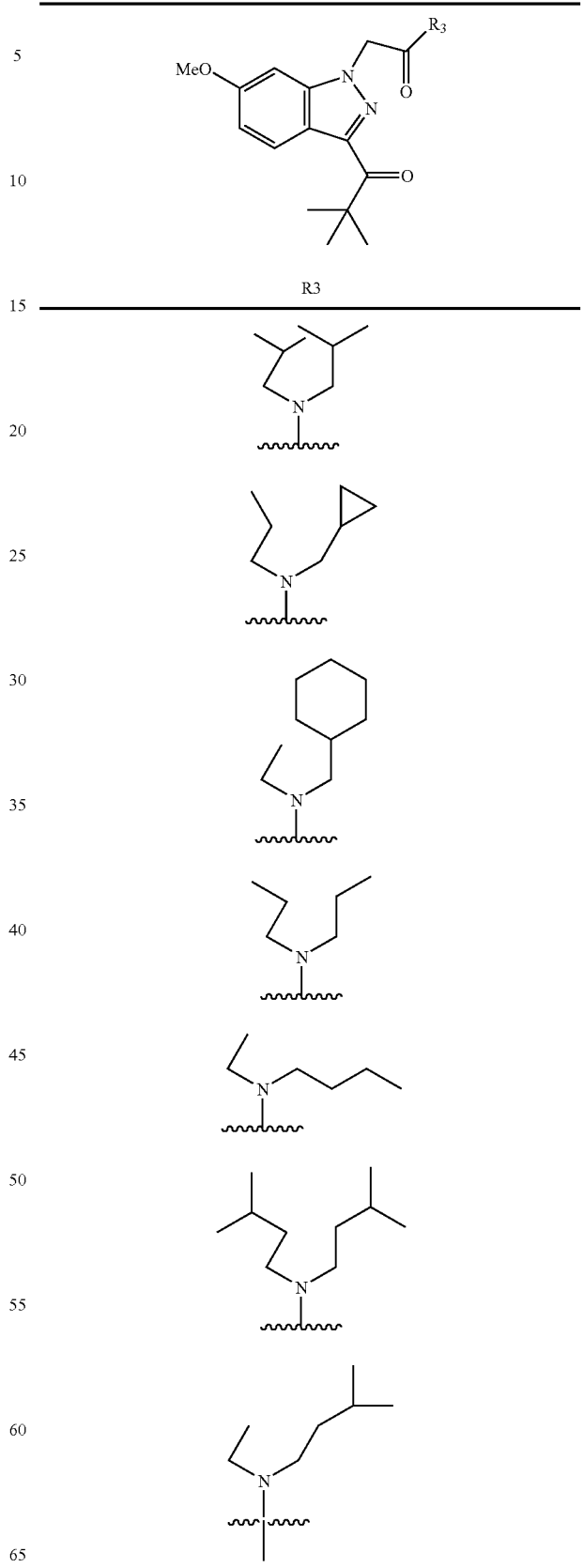

TABLE 3-continued
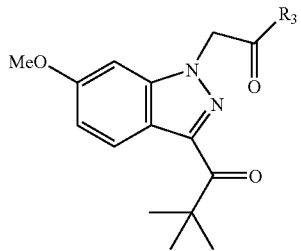
| R3 |
|---|
| 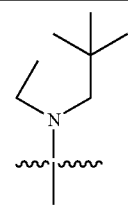 |
| 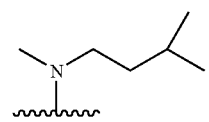 |
| 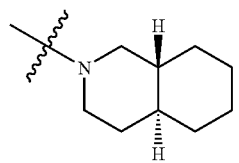 |
| 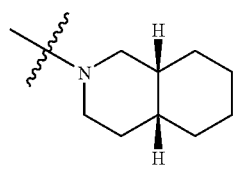 |
| 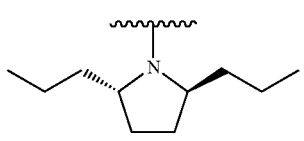 |
| 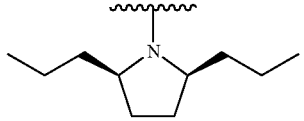 |
|  |
| 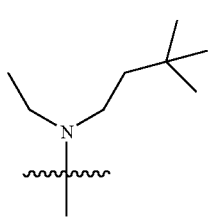 |
TABLE 3-continued
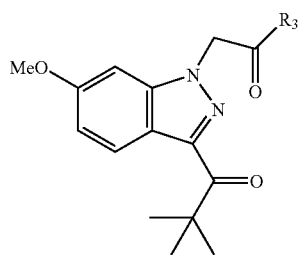
| R3 |
|---|
| 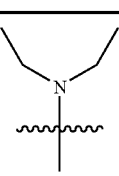 |
| 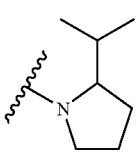 |
| 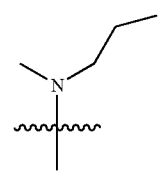 |
TABLE 4
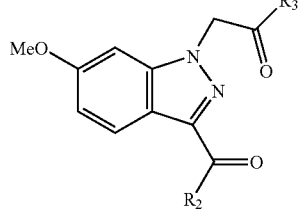
| R2 | R3 |
|---|---|
| 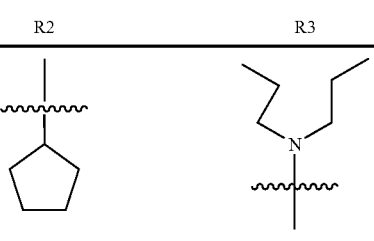 | |
| 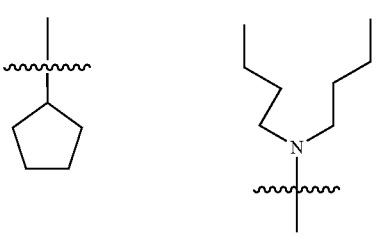 | |

TABLE 4-continued

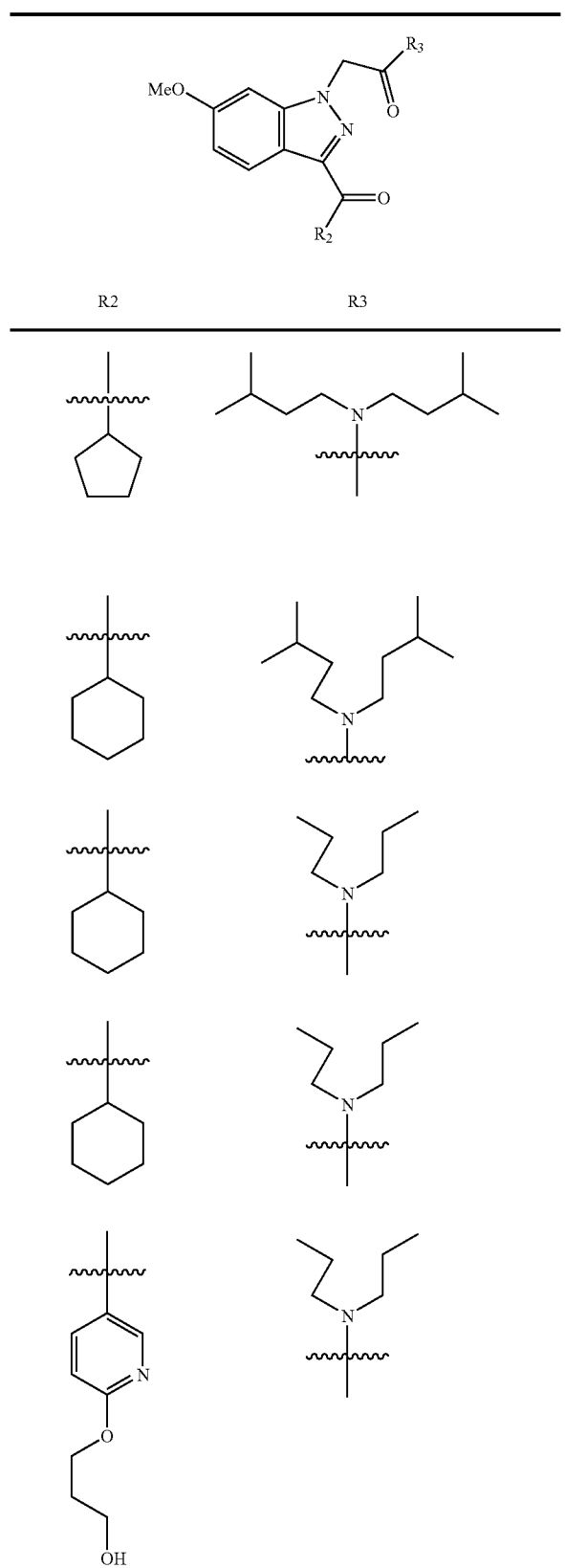

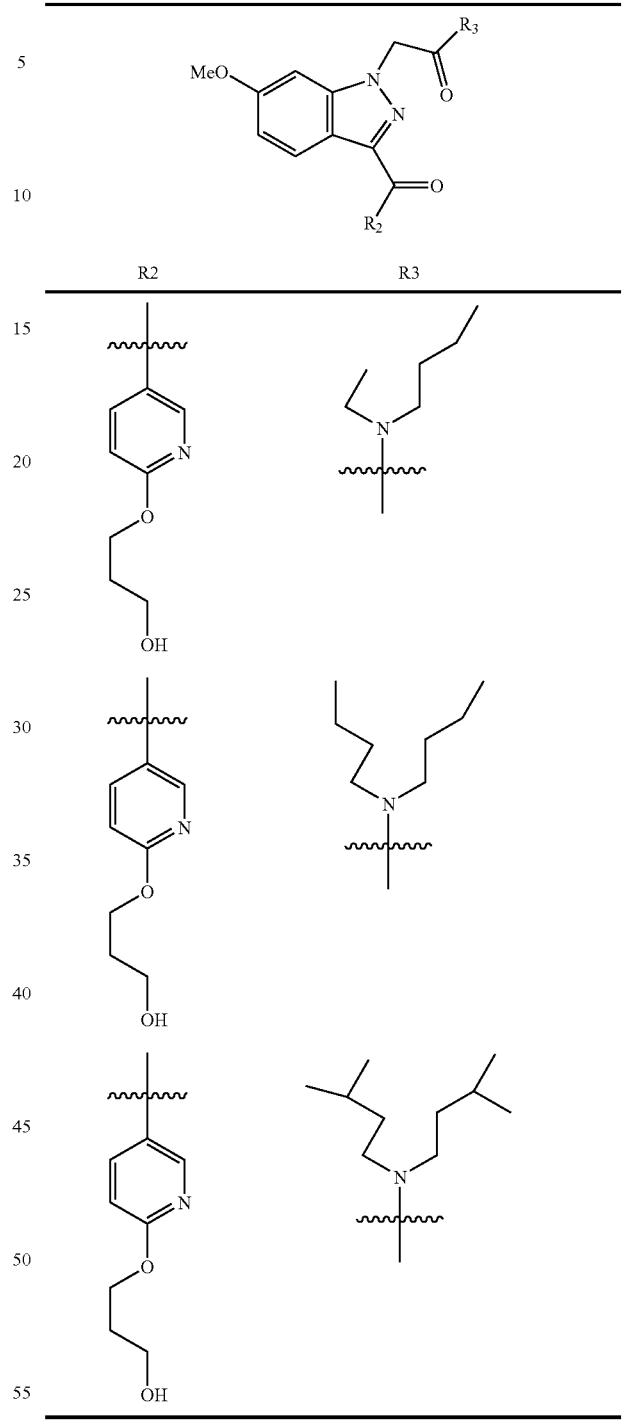

or a pharmaceutically acceptable salt, enantiomer, diastereomer or mixture thereof.

The invention is described herein in detail using the terms defined below unless otherwise specified.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S.

A. Wilen Stereochemistry of Carbon Compounds (John Wiley and Sons, New York 1994), in particular pages 1119-1190).

When any variable (e.g. aryl, heterocycle, $R^1$, $R^6$ etc.) occurs more than one time in any constituent, its definition on each occurrence is independent at every other occurrence. Also, combinations of substituents/or variables are permissible only if such combinations result in stable compounds.

When $R^a$ is —O— and attached to a carbon it is referred to as a carbonyl group and when it is attached to a nitrogen (e.g., nitrogen atom on a pyridyl group) or sulfur atom it is referred to a N-oxide and sulfoxide group, respectively.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopropyl cyclopentyl and cyclohexyl. When the alkyl group is said to be substituted with an alkyl group, this is used interchangeably with "branched alkyl group".

Cycloalkyl is a specie of alkyl containing from 3 to 15 carbon atoms, unless otherwise defined, without alternating or resonating double bonds between carbon atoms. It may contain from 1 to 4 rings, which are fused. Examples of such cycloalkyl elements include, but are not limited to, cyclopropyl, cyclobutyl, cyclopentyl, cyclohexyl and cycloheptyl.

Alkenyl is $C_2$-$C_6$ alkenyl.

Alkoxy refers to an alkyl group of indicated number of carbon atoms attached through an oxygen bridge, with the alkyl group optionally substituted as described herein. Said groups are those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

Halogen (halo) refers to chlorine, fluorine, iodine or bromine.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms; Examples of aryl groups are phenyl, naphthyl, tetrahydronaphthyl, indanyl, biphenyl, phenanthryl, anthryl or acenaphthyl and phenanthrenyl, preferably phenyl, naphthyl or phenanthrenyl. Aryl groups may likewise be substituted as defined. Preferred substituted aryls include phenyl and naphthyl.

The term heterocyclyl or heterocyclic, as used herein, represents a stable 3- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. A fused heterocyclic ring system may include carbocyclic rings and need include only one heterocyclic ring. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, dihydropyrrolyl, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. Preferably, heterocycle is selected from 2-azepinonyl, benzimidazolyl, 2-diazapinonyl, dihydroimidazolyl, dihydropyrrolyl, imidazolyl, 2-imidazolidinonyl, indolyl, isoquinolinyl, morpholinyl, piperidyl, piperazinyl, pyridyl, pyrrolidinyl, 2-piperidinonyl, 2-pyrimidinonyl, 2-pyrollidinonyl, quinolinyl, tetrahydrofuryl, tetrahydroisoquinolinyl, and thienyl.

The term "heteroatom" means O, S or N, selected on an independent basis.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, thienyl and triazolyl. Additional nitrogen atoms may be present together with the first nitrogen and oxygen or sulfur, giving, e.g., thiadiazole.

This invention is also concerned with compositions and methods of treating ocular hypertension or glaucoma by administering to a patient in need thereof one of the compounds of formula I in combination with a β-adrenergic blocking agent such as timolol, betaxolol, levobetaxolol, carteolol, levobunolol, a parasympathomimetic agent such as epinephrine, IOPIDINE (Apraclonidine), brimonidine, clonidine, para-aminoclonidme, carbonic anhydrase inhibitor such as dorzolamide, acetazolamide, metazolamide or brinzolamide, an EP4 agonist (such as those disclosed in WO 02/24647, WO 02/42268, EP I 114816, WO 01/46140 and WO 01/72268), a prostaglandin such as latanoprost, travaprost, unoprostone, RESCULA (Unoprostone isoproyl), S 1033 (compounds set forth in U.S. Pat. Nos. 5,889,052; 5,296,504; 5,422,368; and 5,151,444); a hypotensive lipid such as LUMIGAN (Bimatorrost) and the compounds set forth in U.S. Pat. No. 5,352,708; a neuroprotectant disclosed in U.S. Pat. No. 4,690,931, particularly eliprodil and R-eliprodil as set forth in WO 94/13275, including memantine; or an agonist of 5-HT2 receptors as set forth in PCT/US00/31247, particularly 1-(2-aminopropyl)-3-methyl-IH-imdazol-6-ol fumarate and 2-(3-chloro-6-methoxy-indazol- I-yl)- I-methyl-ethylamine. An example of a hypotensive lipid (the carboxylic acid group on the a-chain link of the basic prostaglandin structure is replaced with electrochemically neutral substituents) is that in which the carboxylic acid group is replaced with a C i-6 alkoxy group such as $OCH_3$ ($PGF_{2a}$ I-$OCH_3$), or a hydroxy group ($PGF_{2a}$ I-OH).

Preferred potassium channel blockers are calcium activated potassium channel blockers. More preferred potassium channel blockers are high conductance, calcium activated potassium (Maxi-K) channel blockers. Maxi-K channels are a family of ion channels that are prevalent in neuronal, smooth muscle and epithelial tissues and which are gated by membrane potential and intracellular $Ca^{2+}$.

The present invention is based upon the finding that maxi-K channels, if blocked, inhibit aqueous humor production by inhibiting net solute and $H_2O$ efflux and therefore lower IOP. This finding suggests that maxi-K channel blockers are useful for treating other ophthamological dysfunctions such as macular edema and macular degeneration. It is known that lowering IOP promotes blood flow to the retina and optic nerve. Accordingly, the compounds of this invention are useful for treating macular edema and/or macular degeneration.

It is believed that maxi-K channel blockers which lower IOP are useful for providing a neuroprotective effect. They are also believed to be effective for increasing retinal and optic nerve head blood velocity and increasing retinal and optic nerve oxygen by lowering IOP, which when coupled together benefits optic nerve health. As a result, this invention further relates to a method for increasing retinal and optic nerve head blood velocity, increasing retinal and optic nerve oxygen tension as well as providing a neuroprotective effect or a combination thereof.

A number of marketed drugs function as potassium channel antagonists. The most important of these include the compounds Glyburide, Glipizide and Tolbutamide. These potassium channel antagonists are useful as antidiabetic agents. The compounds of this invention may be combined with one or more of these compounds to treat diabetes.

Potassium channel antagonists are also utilized as Class 3 antiarrhythmic agents and to treat acute infarctions in humans. A number of naturally occuring toxins are known to block potassium channels including Apamin, lberiotoxin, Charybdotoxin, Noxiustoxin, Kaliotoxin, Dendrotoxin(s), mast cell degranuating (MCD) peptide, and β-Bungarotoxin (β-BTX). The compounds of this invention may be combined with one or more of these compounds to treat arrhythmias.

Depression is related to a decrease in neurotransmitter release. Current treatments of depression include blockers of neurotransmitter uptake, and inhibitors of enzymes involved in neurotransmitter degradation which act to prolong the lifetime of neurotransmitters.

Alzheimer's disease is also characterized by a diminished neurotransmitter release. Three classes of drugs are being investigated for the treatment of Alzheimer's disease cholinergic potentiators such as the anticholinesterase drugs (e.g., physostigmine (eserine), and Tacrine (tetrahydroaminocridine)); nootropics that affect neuron metabolism with little effect elsewhere (e.g., Piracetam, Oxiracetam; and those drugs that affect brain vasculature such as a mixture of ergoloid mesylates amd calcium channel blocking drugs including Nimodipine. Selegiline, a monoamine oxidase B inhibitor which increases brain dopamine and norepinephrine has reportedly caused mild improvement in some Alzheimer's patients. Aluminum chelating agents have been of interest to those who believe Alzheimer's disease is due to aluminum toxicity. Drugs that affect behavior, including neuroleptics, and anxiolytics have been employed. Anxiolytics, which are mild tranquilizers, are less effective than neuroleptics The present invention is related to novel compounds which are useful as potassium channel antagonists.

The compounds within the scope of the present invention exhibit potassium channel antagonist activity and thus are useful in disorders associated with potassium channel malfunction. A number of cognitive disorders such as Alzheimer's Disease, memory loss or depression may benefit from enhanced release of neurotransmitters such as serotonin, dopamine or acetylcholine and the like. Blockage of Maxi-K channels maintains cellular depolarization and therefore enhances secretion of these vital neurotransmitters.

The compounds of this invention may be combined with anticholinesterase drugs such as physostigmine (eserine) and Tacfine (tetrahydroaminocridine), nootropics such as Piracetam, Oxiracetam, ergoloid mesylates, selective calcium channel blockers such as Nimodipine, or monoamine oxidase B inhibitors such as Selegiline, in the treatment of Alzheimer's disease. The compounds of this invention may also be combined with Apamin, lberiotoxin, Charybdotoxin, Noxiustoxin, Kaliotoxin, Dendrotoxin(s), mast cell degranuating (MCD) peptide, β-Bungarotoxin (β-BTX) or a combination thereof in treating arrythmias. The compounds of this invention may further be combined with Glyburide, Glipizide, Tolbutamide or a combination thereof to treat diabetes.

The herein examples illustrate but do not limit the claimed invention. Each of the claimed compounds are potassium channel antagonists and are thus useful in the decribed neurological disorders in which it is desirable to maintain the cell in a depolarized state to achieve maximal neurotransmitter release. The compounds produced in the present invention are readily combined with suitable and known pharmaceutically acceptable excipients to produce compositions which may be administered to mammals, including humans, to achieve effective potassium channel blockage.

For use in medicine, the salts of the compounds of formula I will be pharmaceutically acceptable salts. Other salts may, however, be useful in the preparation of the compounds according to the invention or of their pharmaceutically acceptable salts. When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N[1]-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutaminc, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The preparation of the pharmaceutically acceptable salts described above and other typical pharmaceutically acceptable salts is more fully described by Berg et al., "Pharmaceutical Salts,". J. Pharm. Sci., 1977:66:1-19.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, sex and response of the individual patient, as well as the severity of the patient's symptoms.

The maxi-K channel blockers used can be administered in a therapeutically effective amount intravaneously, subcutaneously, topically, transdermally, parenterally or any other method known to those skilled in the art.

Ophthalmic pharmaceutical compositions are preferably adapted for topical administration to the eye in the form of solutions, suspensions, ointments, creams or as a solid insert. Ophthalmic formulations of this compound may contain from 0.01 ppm to 1% and especially 0.1 ppm to 1% of medicament. Higher dosages as, for example, about 10% or lower dosages can be employed provided the dose is effective in reducing intraocular pressure, treating glaucoma, increasing blood flow velocity or oxygen tension. For a single dose, from between 0.01 to 5000 ng, preferably 0.1 to 500 ng, and especially 1 to 100 ng of the compound can be applied to the human eye.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethyl-cellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopailitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a microparticle formulation. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyactylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

Suitable subjects for the administration of the formulation of the present invention include primates, man and other animals, particularly man and domesticated animals such as cats and dogs.

The pharmaceutical preparation may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

The ophthalmic solution or suspension may be administered as often as necessary to maintain an acceptable IOP level in the eye. It is contemplated that administration to the mamalian eye will be about once or twice daily.

For topical ocular administration the novel formulations of this invention may take the form of solutions, gels, ointments, suspensions or solid inserts, formulated so that a unit dosage comprises a therapeutically effective amount of the active component or some multiple thereof in the case of a combination therapy.

The following examples given by way of illustration is demonstrative of the present invention.

Definitions of the terms used in the examples are as follows:
SM—Starting material,
DMSO—dimethyl sulfoxide,
TLC—thin layer chromatography,
SGC—silica gel chromatography,
PhMgBr—phenylmagnesiumbromide
h=hr=hour,
THF—tetrahydrofuran,
DMF—dimethylformamide,
min—minute,
LC/MS—liquid chromatography/mass spectrometry,
HPLC—high performance liquid chromatography,
PyBOP—Benzotriazol-1-yloxytris-(dimethyl amino)phosphonium hexafluorophosphate,
equiv=eq=equivalent,
NBS—N-Bromosuccinamide and
AEBN—2,2'-azobisisobutyronitrile.

The compounds of this invention generally can be made, with modification where appropriate, in accordance with Schemes 1 and/or 2. Examples 1-17 are also produced in accordance with Schemes 1 and/or 2.

Scheme 1
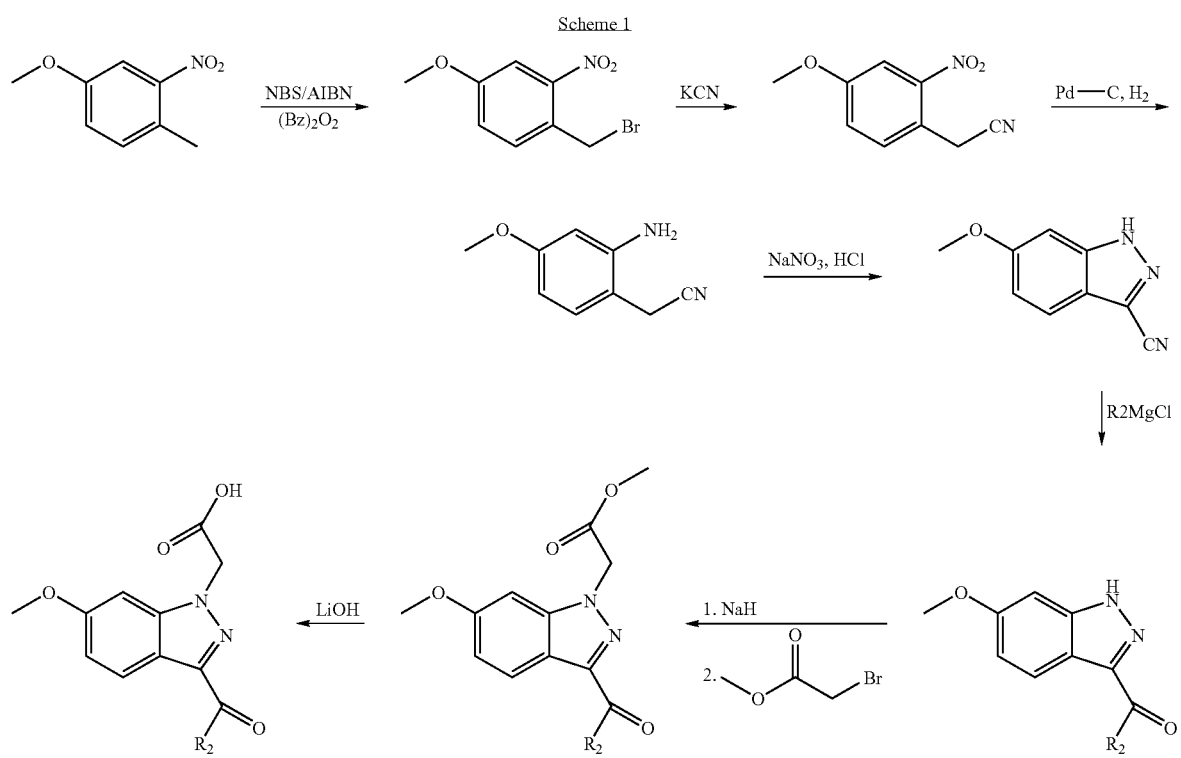
Scheme 2
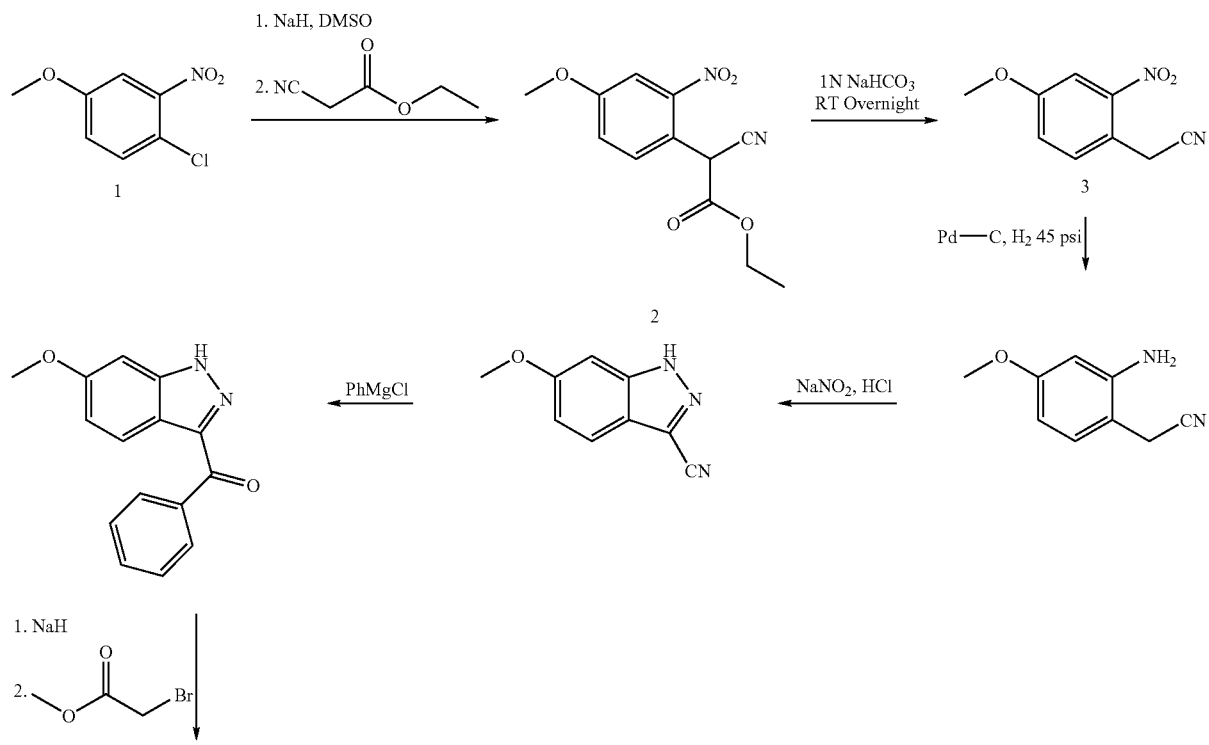

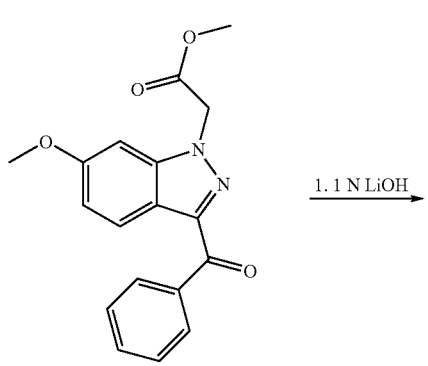

In Scheme 1 nitroanisole is brominated using NBS (N-bromosuccinimide), AIBN and benzoyl peroxide. Treatment of the bromonitroanisole with potassium cyanide yielded the cyanonitroanisole. Conversion of the nitro group to an amine is accomplished by hydrogenation. The amine is then treated with sodium nitrite and HCl to yield the indazole ring. In this reaction as soon as the diazonium is generated by nitrosation of the aniline moiety it is trapped intramolecularily by the acidic benzyl cyanide. Tautomerization of the resultant derivative gives the indazole nucleus. Treatment of the nitrite with a Gringard followed by hydrolysis of the resultant imino-magnesium complex gives the desired alkyl/aryl ketone. Derivation of the head group is achieved by treatment of the indazole with NaH to deprotonate the nitrogen followed by addition of methylbromoacetate to form the requisite ester. The acid is obtained by hydrolysis with LiOH.

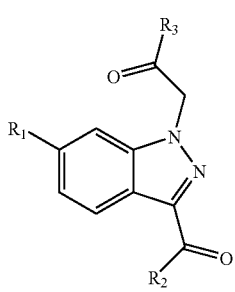

Figure 1

In Scheme 2, 1-Chloro-3-nitroanisole is treated with a cyanoester salt generated by the treatment of ethyl cyano acetate with NaH in DMSO to yield product 2 [(ethyl cyano (4-methoxy-2-nitrophenyl)acetate]. Hydrolysis and Decarboxylation with 1N sodium bicarbonate generates 3 (4-methoxy-2-nitro phenyl acetonitrile). The rest of the subsequent steps in the synthesis remaines the same from Scheme 1. This synthesis can be used, for example, to generate an indazole with a methoxy in the $R_1$ position and an isopropyl in the $R_2$ position (see FIG. 1). The acid of this compound can be used to generate a series of analogs by peptide coupling.

In addition, one of ordinary skill in the art would appreciate that in the schemes above if the amine is replaced with alcohols then the corresponding O-derivatives will follow.

Preparative Example 1

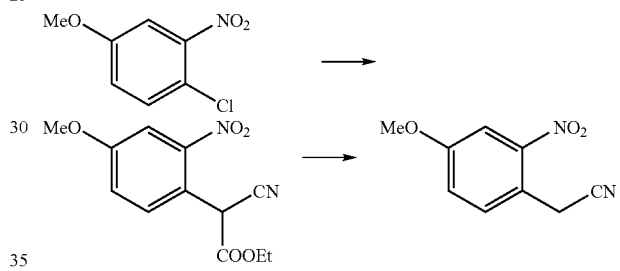

In a 500 mL flask was charged 336 mmoles (13.44 g; 60%) of NaH. Under argon 150 mL of DMSO was added, followed by dropwise addition of 32 mL of ethyl cyanoacetate (2.2 equiv.; 352 mmloes) at 5° C. After all the addition the reaction was warmed up to room temperature over 1 h. 30 g of starting nitrobenzene derivative was added (160 mmoles) as a powder. The reaction mixture was heated in a closed system at 90° C. for 8 hours. Acidification and standard work-up gave a crude oily residue which was purified over a silica-gel column to give 39 g of desired crystalline product which was decarboxylated to give the benzylnitrile as follows. Thirty eight grams of starting material obtained above was dissolved in 400 mL of 1N sodium carbonate. The homogenous solution was stirred at rt for two days. TLC analysis indicated competion of reaction. The reaction mixture was acidified and extracted with ethyl acetate (100 mL×4). The combined organic phases was dried over sodium sulfate and concentrated and residue was subjected to SGC to give the desired product.

$^1$H NMR CDCL3: 7.72 (1H, d, J=3 Hz); 7.61 (1H, d, J=8.5 Hz); 7.25 (1H, dd, J=3 and 8.5 Hz); 4.17 (2H, s); 3.94 (3H, s). LCMS [M+H]=193.

Preparative Example 2

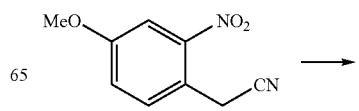

27

-continued

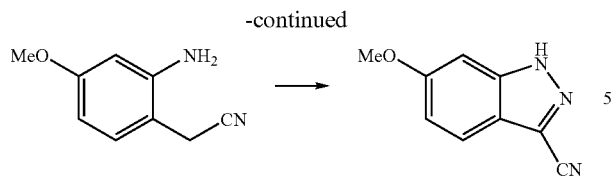

10 g of benzylnitrile derivative was dissolved in THE 20 mL followed by dilution with 50 mL of methanol. The reaction mixture was taken in a pressure tube, Pd—C (10% wt/10 mole %) was added and the reaction mixture was hydrogenated at 40 psi. After the requisite amount of hydrogen for the reduction of the $NO_2$ group was consumed the reaction was stopped. TLC analysis indicated a spot to spot convenrsion. The reaction mixture was filtered over a pad of celite and the filtrate was concentrated to a solid and used in the next step directly. Crude aniline derivative (52 mmoles was dissloved/suspended in 2N HCl (150 mL), cooled to 5° C. followed by the addition of 5.4 g of sodium nitrite in 10 mL of water. The reaction mixture was allowed to stir for 1 h with gradual warming to room temperature. TLC analysis indicated complete consumption of SM(starting material) and the formation of a new spot. The reaction mixture was extracted with ethyl acetate (100 mL×4); organic phase was collected, dried and concentrated. The residue was purified by SGC to give desired product. LCMS [M+H]=174

Preparative Example 3

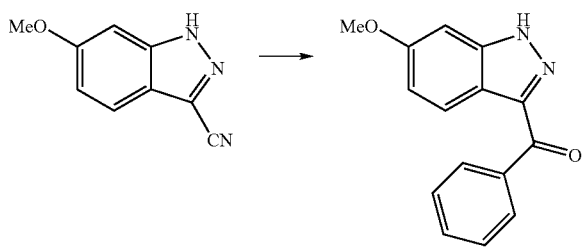

Nitrile (1.5 g, from Preparative Example 2) was dissolved in 20 mL of dry THF and under argon 3 equiv. of PhMgBr (1M in THF) was added at 5° C. The reaction mixture was stirred at room temperature for 1 h. The reaction was carefully quenched by addition of water and 1N HCl (15 mL). The quenched reaction mixture was stirred at room temperature for 1 hour then extracted with ethyl acetate (20 mL X3); combined organic phases were dried over sodium sulfate and

28 concentrated to a solid residue which was azeotroped with toluene three times and used in the next step directly. LCMS [M+H]=253

EXAMPLE 1

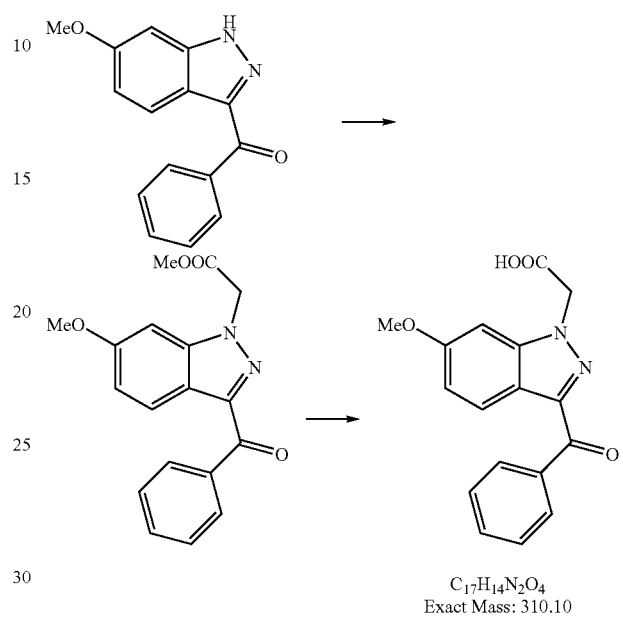

$C_{17}H_{14}N_2O_4$
Exact Mass: 310.10

Benzoyl derivative (8.6 mmoles, obtained from Preparative Example 3) was dissolved in 8 mL of DMF followed by the addition of 1.2 equiv. of NaH (60% solution in mineral oil). After stirring at room temperature for 15 min 1.5 equiv. of methyl bromoacetate was added and the reaction mixture was stirred for additional 0.5 h. TLC analysis indicated completion of reaction. Standard aqueous work-up followed by SGC purification of the crude material gave 2.2 grams of desired acetate derivative. Hydrolysis of the methyl ester was carried out using LiOH. Ester (2.2 g; 6.8 mmoles) was dissolved in 100 mL of THF followed by the addition of 1M LiOH (15 mL). The reaction was complete in 0.5 h according to TLC and LCMS. Acidification by addition of 15 mL of 1N HCl followed by extraction with ethyl acetate and evaporation of solvent gave solid residue which was 95% pure by HPLC and suitable to be used in the coupling step. LCMS [M+H]=311Example 2

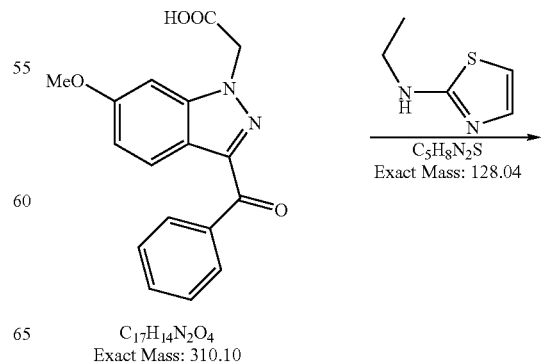

$C_{17}H_{14}N_2O_4$
Exact Mass: 310.10

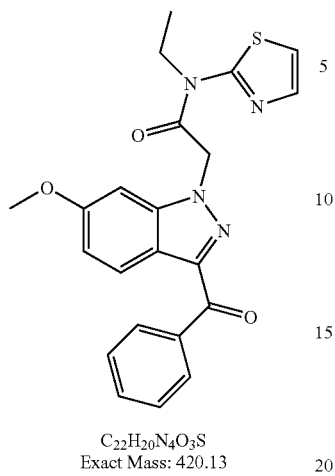

C₂₂H₂₀N₄O₃S
Exact Mass: 420.13

Acid (300 mg from Example 1) was coupled with N-ethyl-5-aminothiazole derivative (1.2 equiv.) using PyBOP (2.2 equiv.) and Hunigs base (3 equiv) in acetonitrile (5 mL) at 90° C. The reaction was complete in 45 min. Standard work-up followed by SGC purification gave the desired product as a white foam. LCMS [M+H]=421

Examples 4 through 14 as shown below, are made, with some modification, by the addition of the NR₂ group in accordance with Schemes 1 and 2 and Examples 1-3.

EXAMPLE 3

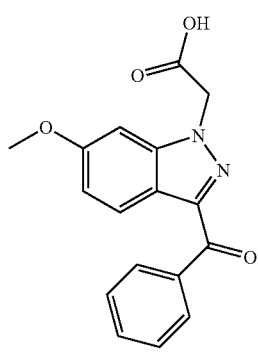

C₁₇H₁₄N₂O₄
Exact Mass: 310.10

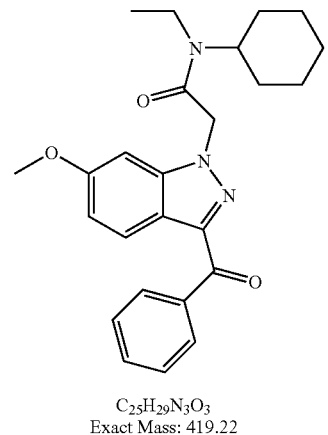

C₂₅H₂₉N₃O₃
Exact Mass: 419.22

LCMS [M+H]=420

EXAMPLE 4

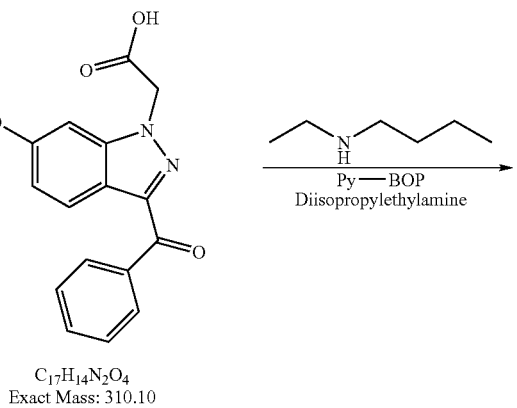

C₁₇H₁₄N₂O₄
Exact Mass: 310.10

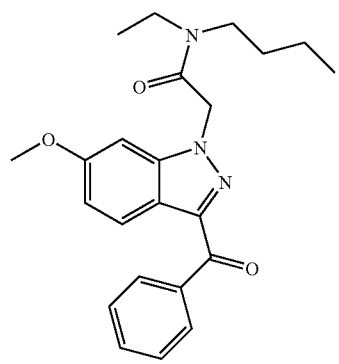

C₂₃H₂₇N₃O₃
Exact Mass: 393.21

LCMS [M+H]=394

EXAMPLE 5
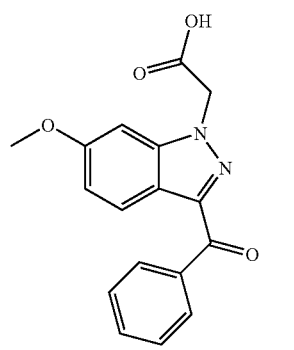
C$_{17}$H$_{14}$N$_2$O$_4$
Exact Mass: 310.10
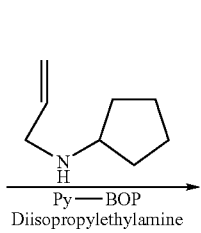
Py—BOP
Diisopropylethylamine
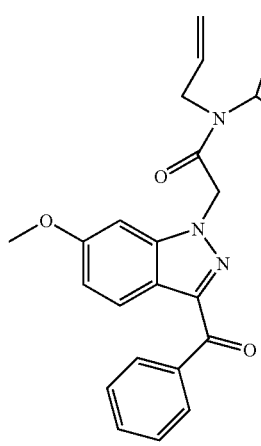
C$_{25}$H$_{27}$N$_3$O$_3$
Exact Mass: 417.21
LCMS [M+H]=418
EXAMPLE 6
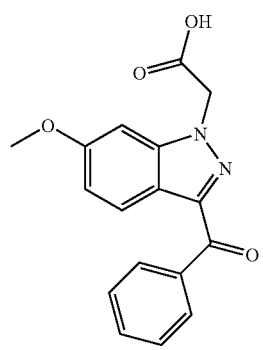
C$_{17}$H$_{14}$N$_2$O$_4$
Exact Mass: 310.10
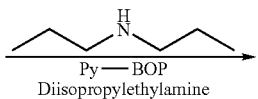
Py—BOP
Diisopropylethylamine
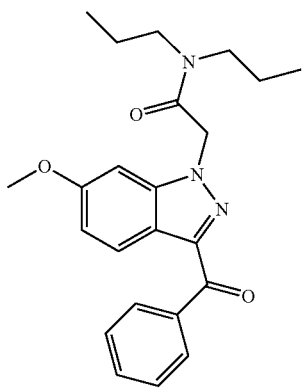
C$_{23}$H$_{27}$N$_3$O$_3$
Exact Mass: 393.21
EXAMPLE 7
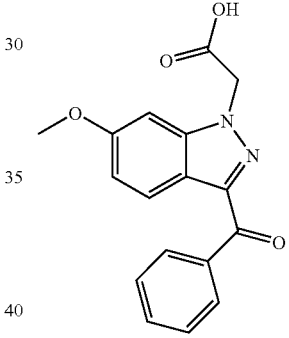
C$_{17}$H$_{14}$N$_2$O$_4$
Exact Mass: 310.10
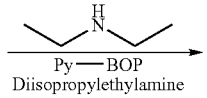
Py—BOP
Diisopropylethylamine
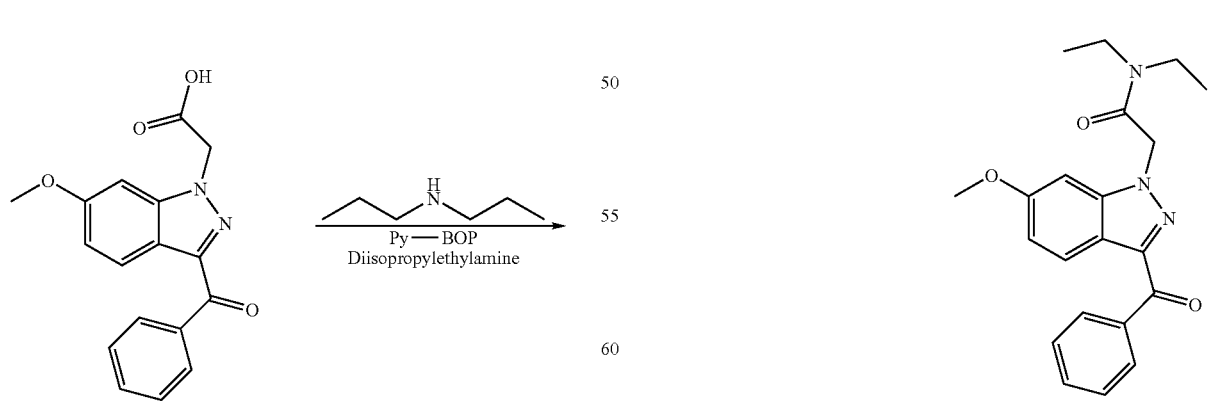
C$_{21}$H$_{23}$N$_3$O$_3$
Exact Mass: 365.17
LCMS [M+H]=366

EXAMPLE 8
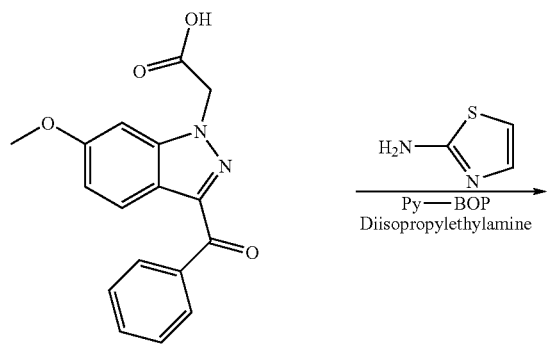
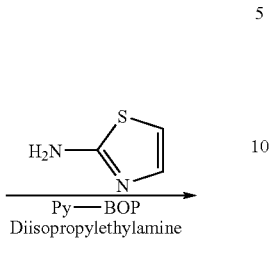
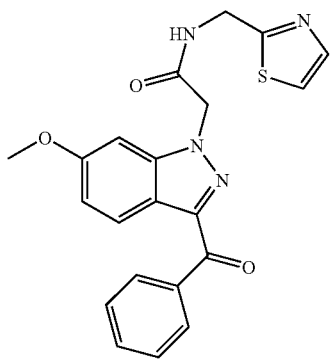
LCMS [M+H]=393
EXAMPLE 9
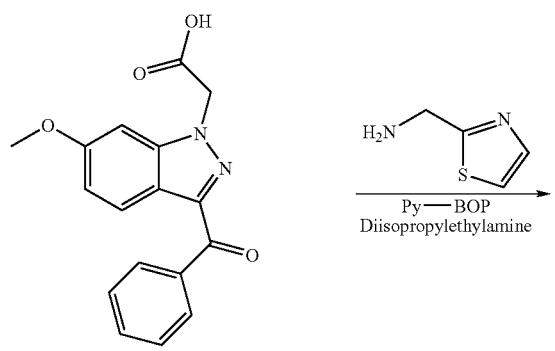
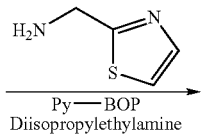
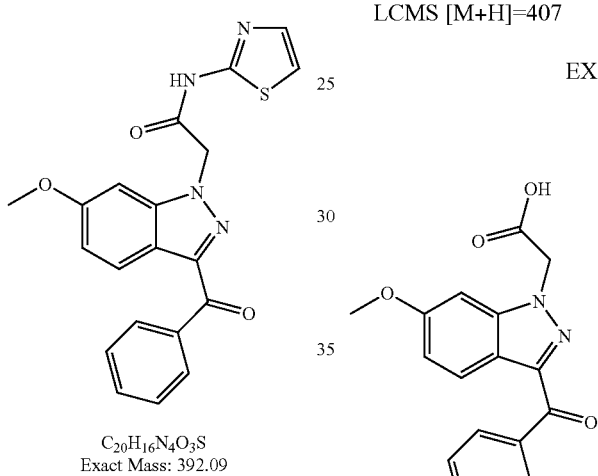
LCMS [M+H]=407
EXAMPLE 10
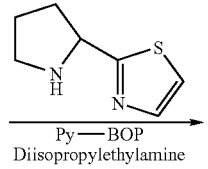
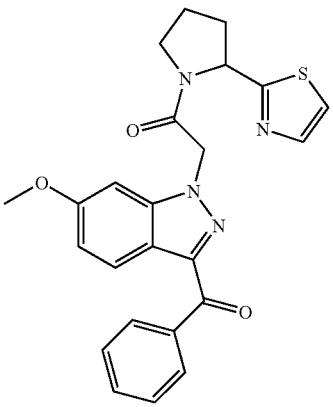
LCMS [M+H]=447

EXAMPLE 11

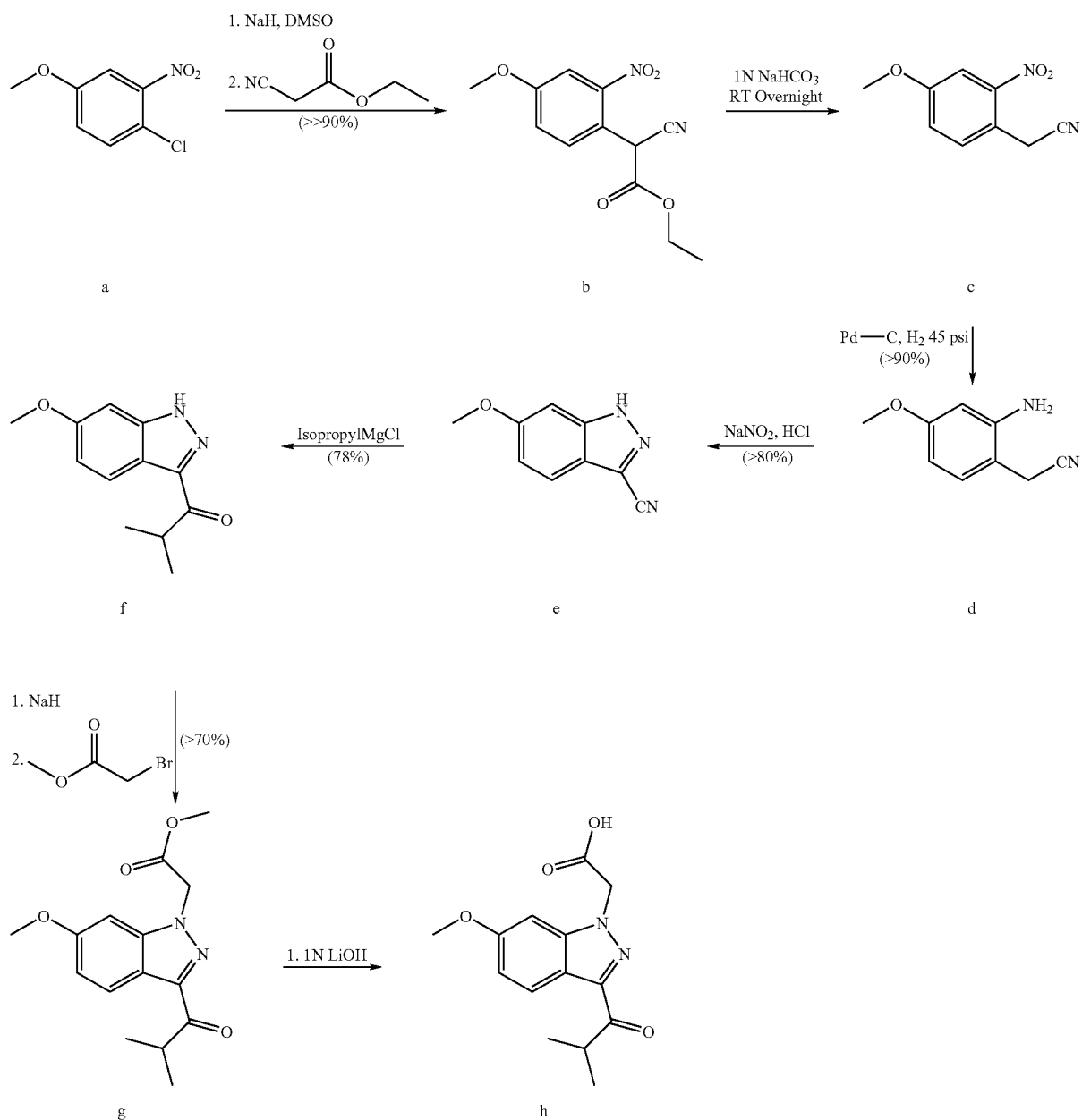

Weighed out 4.15 g of indazole (compound e, Preparative Example 2) and azeoptroped water with 2 toluene (100 ml) washings, pulling off toluene azeotrope by rotovap. Dried thoroughly under high vacuum and performed argon purges. Dissolved in 40 ml dry THF and 92 ml dry ether under argon. Cooled to 5° C. in ice water bath. Charged 3 eq of isopropylmagnesium chloride (36 ml of a 2M solution in THF) and stired for 0.5 hour at room temp. Carefully charged 1N HCl (240 ml) and stired for 1 h. Monitored reaction by LC. Extracted with EtOAc, rotovaped to provided compound f. LCMS [M+H]=219

Starting Material (3.40 g, Compound f) was weighed out into flask and dried with toluene (100 ml) and azeotrope removed by rotovap and high vacuum. Charged 20 ml DMF and 3 eq NaH (0.5761 g) and allowed to stir for 15 min. Charged 2.5 eq methyl bromoacetate (3.8 ml) under cooling. Ran LC/MS upon completion of addition. Continued monitoring by LC/MS. Compound g was produced. LCMS [M+H] =291

SM ester (compound g, 2.23 g) was weighed out into round bottom flask. Charged 115 ml THF and 16 ml LiOH allowed to stir overnight. Ran LC/MS. Charged 20 ml 1 N HCl. Extracted with EtOAc, rotovaped. Ran LC/MS upon completion of addition. Continued monitoring by LC/MS. Purified by column chromatography to produce the acid, compound h.

1H NMR CDCL3: 8.25 (1H, d, J=8.5 Hz); 7.0 (1H, dd, J=3 and 8.5 Hz); 6.65 (1H, d, J=3 Hz); 5.21 (2H, s); 3.94 (3H, s); 3.8 (2H, s); 1.6 (1H, m); 1.25 (6H, d, J=7 Hz). LCMS [M+H] =277

Preparative Example 4

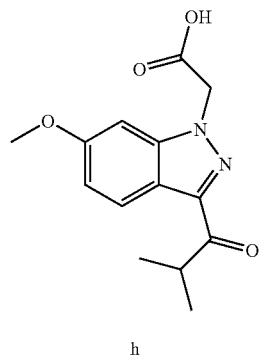

h

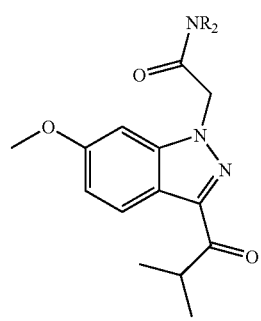

i

Compound h (from Example 11) is coupled with an amine NH(R)$_2$ in the presence of py-BOP and a base, such as diisopropylethylamine to provide compound i such as Examples 12-17, following the procedures described below in Examples 12 and 13.

EXAMPLE 12

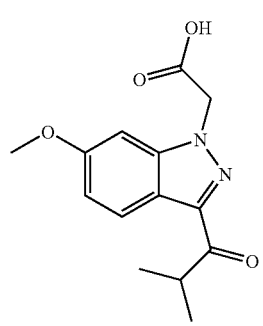

C$_{14}$H$_{16}$N$_2$O$_4$
Exact Mass: 276.11

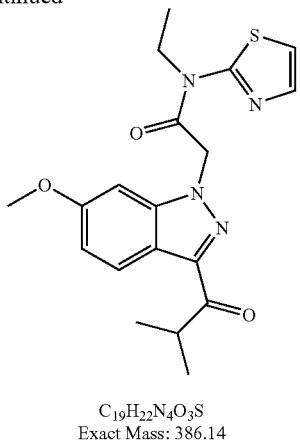

C$_{19}$H$_{22}$N$_4$O$_3$S
Exact Mass: 386.14

Charged acid compound h (100 mg) from Example 11, 0.3204 g Py-BOP, 0.19 ml diisopropylethylamine, 0.07 g 2-ethylaminothiazole, and 3.5 ml acetonitrile into oven dried test tube with a test tube. Heated to 90° C. and allowed to react for 45 min. Reaction was treated with saturated NaCl and extracted with ethyl acetate. Solvent rotovaped off and product purified by column chromatography to provide the desired compound i where R=N-ethyl-2-thiazolyl. Product analyzed by NMR and LC/MS. LCMS [M+H]=387

EXAMPLE 13

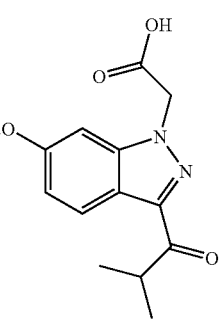

C$_{14}$H$_{16}$N$_2$O$_4$
Exact Mass: 276.11

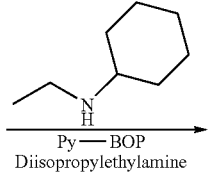

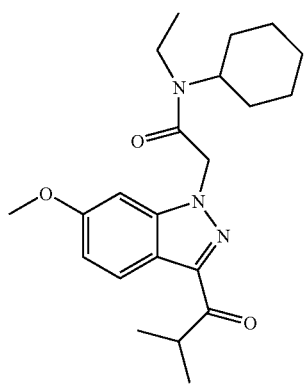

C$_{22}$H$_{31}$N$_3$O$_3$
Exact Mass: 385.24

Charged 100 mg of acid (Compound h, from Example 11) 0.3204 g Py-BOP, 0.19 ml diisopropylethylamine, and 0.1 ml, N-ethylcyclohexylamine and 3.5 ml acetonitrile into oven dried test tube with a test tube. Heated to 90° C. and allowed to react for 45 min. Reaction was treated wtih saturated NaCl and extracted with ethyl acetate. Solvent rotovaped away and product purified by column chromatography. Purified product analyzed by NMR and LC/MS. LCMS [M+H]=386

The following examples 14-17 were made using methods in accordance with Preparative Example 4 and Examples 12-13 and substituting the appropriate amine starting material.

EXAMPLE 14

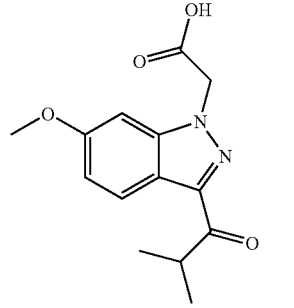

$C_{14}H_{16}N_2O_4$
Exact Mass: 276.11

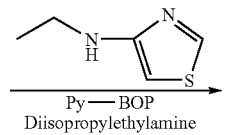

EXAMPLE 15

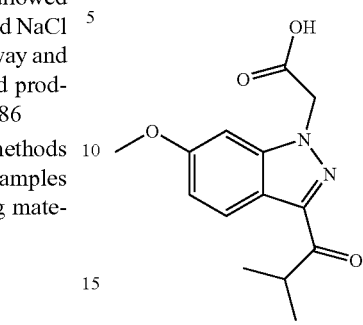

$C_{14}H_{16}N_2O_4$
Exact Mass: 276.11

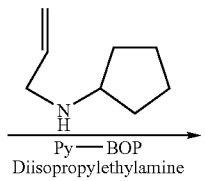

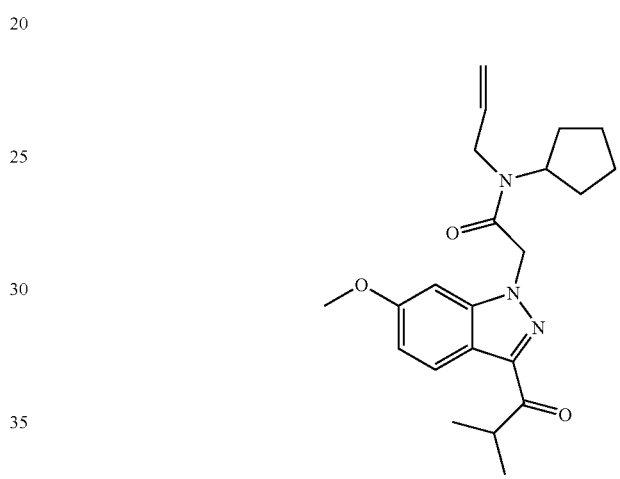

$C_{22}H_{29}N_3O_3$
Exact Mass: 383.22

LCMS [M+H]=384

EXAMPLE 16

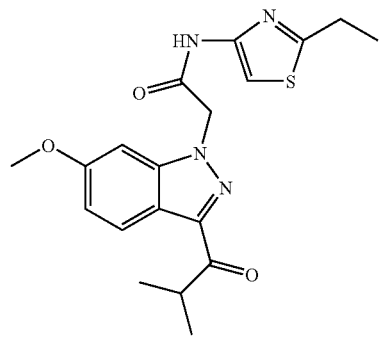

$C_{19}H_{22}N_4O_3S$
Exact Mass: 386.14

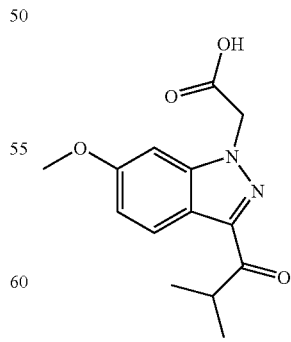

$C_{14}H_{16}N_2O_4$
Exact Mass: 276.11

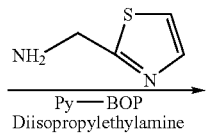

LCMS [M+H]=387

-continued

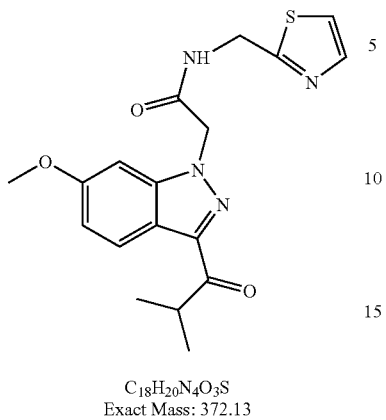

C₁₈H₂₀N₄O₃S
Exact Mass: 372.13

LCMS [M+H]=373

EXAMPLE 17

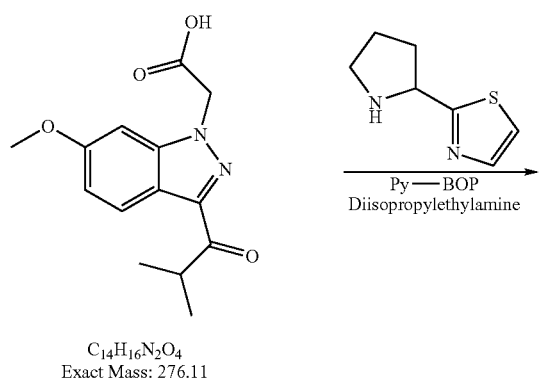

C₁₄H₁₆N₂O₄
Exact Mass: 276.11

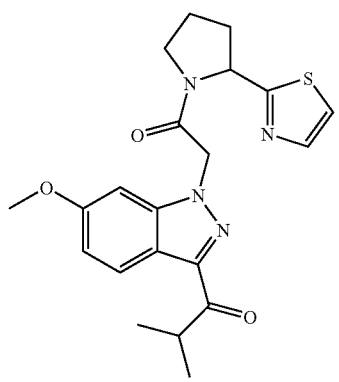

C₂₁H₂₄N₄O₃S
Exact Mass: 412.16

LCMS [M+H]=413

Examples 18 through 26 were made in accordance with Preparative Examples 5 through 14.

PREPARATIVE EXAMPLE 5

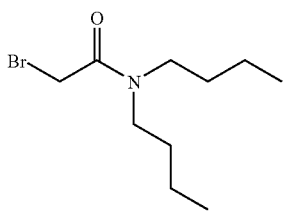

A solution of 1.99 g (10 mmol) of bromoacetate bromide in 20 mL of $CH_2Cl_2$ was cooled down to −78° C. and TEA (1.21 g, 12 mmol) was added dropwise. The reaction mixture stirred for 20 min before dibutyl amine (1.54 g, 12 mmol) was added dropwise. After reaction completed and the mixture was washed with 1N HCl, $H_2O$, brine, dried over $MgSO_4$, and concentrated in vacuo to yield a brown oil. The material was used without any further purification.

$^1$H NMR (CDCl$_3$) δ: 0.95 (6H, m), 1.35 (4H, m), 1.55 (4H, m), 3.30 (4H, m), 3.85 (2H, s).

PREPARATIVE EXAMPLE 6

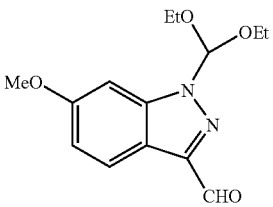

Step A:

To a solution of dibromide (23.2 g, by-product of Example 1, step-3) in acetic acid was added sodium acetate (22.5 g). The mixture was placed in oil bath and refluxed for a couple of hours until reaction completed. The mixture was cooled to room temperature and then poured into ice/water to give desired compound as an off-white solid. The solid was isolated by filtration and dried over nitrogen atmosphere.

$^1$H NMR (CDCl$_3$): & 10.23 (1H, s); 8.19 (1H, d); 7.02 (1H, dd); 6.96 (1H, d); 3.90 (3H, s).

Step B:

To the intermediate from Step A was added triethyl orthoformate (40 ml) and heated to 130° C. for a couple of hours. The resulting mixture was concentrated to dry to give title compound as a brown solid (11.9 g).

$^1$H NMR (DMSO): δ 10.08 (1H, s); 7.98 (1H, d); 7.25 (1H, d); 7.02 (1H, dd); 6.81 (1H, s); 3.82 (3H, s); 3.52 (4H, q); 1.11 (6H, t).

PREPARATIVE EXAMPLE 7

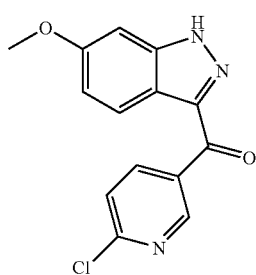

To a solution of 5-iodo-2-chloropyridine (2.56 g, 10.78 mmol) in THF (10 mL) was added iPrMgBr dropwise at −78° C. The reaction stirred for 1 h before Preparative Example 6 (1.71 g, 6.10 mmol) was added as a solution in THF (5 mL). After 2 h and the reaction was quenched with 1N NaOH and extracted with EtOAc. The combined organic layers were washed with brine, dried over MgSO$_4$, and concentrated in vacuo. To a solution of the crude product in toluene (50 mL) was added MnO$_2$ (2.173 g, 25.0 mmol) and the reaction mixture was heated to 130° C. After 1 h the reaction was complete, filtered through a celite pad, and concentrated in vacuo. The crude product was dissolved in THF (10 mL) and 4 mL of 1N HCl was added dropwise. The reaction stirred at RT until TLC analysis indicated completion. The reaction mixture was cooled to 0° C. and the solid precipitate was collected (1.131 g, 64%). $^1$H NMR (CD$_3$OD) δ: 3.900 (3H, s), 7.013 (1H, d), 7.062 (1H, s), 7.627 (1H, d), 8.672 (1H, d), 9.306 (1H, s).

PREPARATIVE EXAMPLE 8

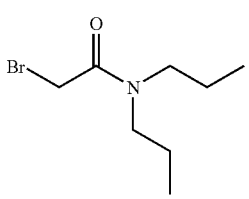

This intermediate was prepared as described in Preparative Example 5, but dipropyl amine was used in place of dibutyl amine.

$^1$H NMR (CDCl$_3$) δ: 0.95 (6H, m), 1.60 (4H, m), 3.25 (4H, m), 3.82 (2H, s).

PREPARATIVE EXAMPLE 9

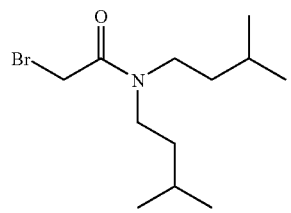

This intermediate was synthesized as described in Preparative Example 5, but diisoamyl amine was used in place of dibutyl amine.

$^1$H NMR (CDCl$_3$) δ: 0.95 (12H, m), 1.40 (2H, m), 1.60 (4H, m), 3.30 (4H, m), 3.82 (2H, s).

PREPARATIVE EXAMPLE 10

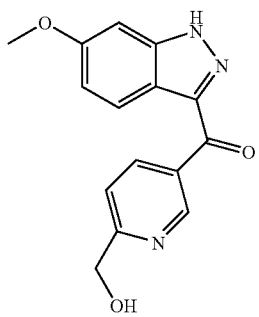

To a stirring solution of Preparative Example 14 (275 mg, 1.02 mmol) in CH$_3$N was added TEA (0.169 mL, 1.22 mmol), DMAP (12 mg, 0.102 mmol), and tert-butoxycarbonyl anhydride (265 mg, 1.22 mmol). After 30 min the reaction was diluted with EtOAc and extracted with H$_2$O, brine, dried over MgSO$_4$, and condensed in vacuo. To the crude material was added peracetic acid (0.159 mL, 1.278 mmol) at 0° C. TLC indicated the reaction was complete after 1.5 h and the reaction mixture was concentrated in vacuo. The crude material was purified via silica gel chromatography. The N-oxide was dissolved in CH$_2$Cl$_2$ and TFAA was added dropwise at 0° C. The reaction warmed up to RT and stirred overnight. To the completed reaction was diluted with H$_2$O and EtOAc and the pH was adjusted to 13-14 with 1N NaOH. The aqueous layer was washed with EtOAc and the combined organic layers were washed with H$_2$O, brine, dried over MgSO$_4$, and condensed in vacuo to yield the desired product (52 mg, 18%).

¹H NMR (CDCl₃) δ: 3.90 (3H, s), 4.95 (2H, s), 6.85 (1H, s), 7.05 (1H, d), 7.50 (1H, d), 8.30 (1H, d), 8.68 (1H, d), 9.64 (1H, s).

PREPARATIVE EXAMPLE 11

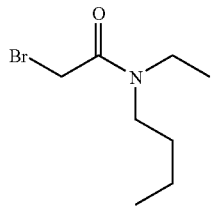

This intermediate was synthesized as described in Preparative Example 5, but N,N-ethylbutyl amine was used in place of dibutyl amine.

¹H NMR (CDCl₃) δ: 0.95-0.99 (3H, m), 1.15-1.26 (3H, m), 1.35 (2H, m), 3.59 (2H, m), 3.30-3.40 (4H, m), 3.86 (2H, s).

PREPARATIVE EXAMPLE 12

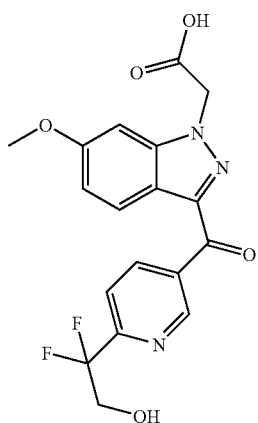

Step A:

To a solution of 2-pyridineacetic acid, 5-bromo-α,α-difluoro-, ethyl ester (13.4 g; prepared according to "Ero, H.; Haneko, Y.; Sakamoto, T. Chem Pharm. Bull. 2000, 48, 982.") in ethanol was added sodium borohydride (2.3 g) portion-wise at 0° C. After stirring at 0° C. for 1 hour, the mixture was poured into water and extracted with ethyl acetate. The organic layer was washed with 1N NaOH$_{aq}$, brine, dried (MgSO₄), and concentrated under reduced pressure to afford crude alcohol. The crude alcohol in methylene chloride was added imidazole (4.1 g) and TBS-Cl (8.3 g) at 0° C. The mixture was stirred for 1 hour. The reaction was poured into 0.1 N HCl$_{aq}$ extracted with methylene chloride. The organic layer was washed with brine, dried (MgSO₄) and evaporated. The residue was purified by silica gel (100% methylene chloride) to give the desired compound as a colorless oil (13.5 g).

¹H NMR (CDCl₃): δ 8.75 (1H, d); 7.95 (1H, dd); 7.57 (1H, d); 4.20 (2H, t); 0.82 (9H, s); 0.02 (6H, s).

Step B:

The desired compound was prepared by a procedure similar to the one described for Preparative Example 14.

¹HNMR (DMSO): δ 9.35 (1H, d); 8.65 (1H, dd); 8.14 (1H, d); 7.88 (1H, d); 7.10 (1H, d); 7.03 (1H, dd); 4.05 (2H, t); 3.85 (3H, s). LC-MS (M+H)=334.2.

Step C:

To a solution of the intermediate from Step B (200 mg, 0.602 mmol) and Cs₂CO₃ (586 mg, 1.806 mmol) in DM (4 mL) was added ethyl bromoacetate (0.134 mL, 1.204 mmol). After 40 min the reaction was complete and quenched with H₂O. The reaction mixture was extracted with EtOAc and the combined organic layers were washed with H₂O, brine, dried over MgSO₄, and concentrated in vacuo. The material was used with no further purification.

¹H NMR (CDCl₃) δ: 1.286 (3H, m), 3.915 (3H, s), 4.296 (4H, m), 5.209 (2H, s), 6.738 (1H, s), 7.063 (1H, d), 7.871 (1H, d), 8.310 (1H, d), 8.708 (1H, d), 9.527 (1H, s).

Step D:

To a solution of the intermediate from Step C was added 12 mL of THF/EtOH/H₂O (1:1:1) followed by the addition of 150 mg of NaOH. After 1 h the reaction was complete and the THF and EtOAc were removed in vacuo. The aqueous layer was extracted with ether, acidified to pH 2, diluted with EtOAc, washed with H₂O, dried over MgSO₄, and concentrated in vacuo. The crude product was used with no further purification.

¹H NMR (CD₃OD) δ: 3.909 (3H, s), 4.157 (2H, t), 5.374 (2H, s), 7.027 (1H, d), 7.103 (1H, s), 7.881 (1H, d), 8.201 (1H, d), 8.764 (1H, d), 9.462 (1H, s).

PREPARATIVE EXAMPLE 13

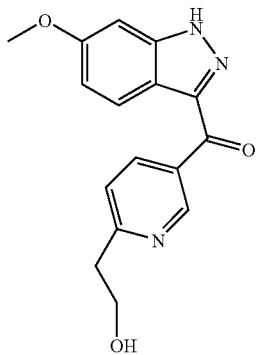

Step A:

To a solution of 2,5-dibromopyridine (2.4 g) in toluene was added tributylallyltin (3.4 ml) and dichlorobis(triphenylphosphine) palladium (0.7 g) under nitrogen atmosphere. The mixture was refluxed for a couple of hours and concentrated under reduced pressure. The residue was re-dissolved in "wet ether" and added DBU (3 ml) slowly to give a cloudy solution. The mixture was filtered over a pad of silica gel and concentrated. The residue was dissolved in methylene chloride/methanol=1/1 solution and cooled to −78° C. To this solution was bubbled though ozone until the reaction mixture became a blue color. The reaction was warmed to 0° C. and added sodium borohydride (0.5 g) portion-wise. After stirring at 0° C. for 1 hour, the mixture was poured into water and extracted with ethyl acetate. The organic layer was washed with 1N NaOH$_{aq}$, brine, dried (MgSO₄), and concentrated under reduced pressure to afford crude alcohol. The alcohol was purified by silica gel (methylene chloride/ethyl acetate=1/1) to give desired alcohol. To a solution of alcohol in methylene chloride was added imidazole (0.4 g) and TBS-Cl (0.8 g) at 0° C. The mixture was stirred for 1 hour. The reaction was poured into 0.1 N HCl$_{aq}$ extracted with methylene chloride. The organic layer was washed with brine, dried (MgSO$_4$) and evaporated. The residue was purified by silica gel (100% methylene chloride) to give desired compound (1.05 g).

$^1$HNMR (CDCl$_3$): δ 8.61 (1H, d); 7.73 (1H, dd); 7.14 (1H, d); 3.97 (2H, t); 2.96 (2H, t); 0.86 (9H, s); −0.02 (6H, s).

Step B:

The Preparative Example 13 was prepared by the procedure similar to the one described for Preparative Example 14. The desired Preparative Example 13 was precipitate out in pH>10.

$^1$H NMR (DMSO): δ 9.23 (1H, d); 8.43 (1H, dd); 8.11 (1H, d); 7.46 (1H, d); 7.04 (1H, dd); 6.99 (1H, d); 4.85 (2H, t); 3.83 (3H, s); 2.97 (2H, t). LC-MS (M+H)=298.4

PREPARATIVE EXAMPLE 14

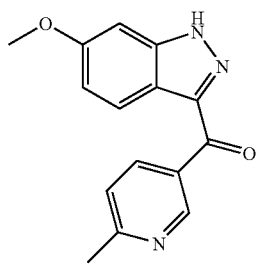

To a solution of 5-bromo-2-methylpyridine (736 mg, 4.31 mmol) in THF (15 mL) was added nBuLi dropwise (2.156 mL, 5.39 mmol, 2.5 M in hexanes) at −78° C. The reaction stirred for 1 h before Preparative Example 6 (1.00 g, 3.59 mmol) was added as a solution in THF (5 mL). The starting material was consumed after 2 h and the reaction was quenched with 1N NaOH and extracted with EtOAc. The combined organic layers were washed with brine, dried over MgSO$_4$, and concentrated in vacuo. A solution of the crude product in toluene (20 mL) was added MnO$_2$ (0.414 g, 4.77 mmol) and the reaction mixture was heated to 130° C. After 1 h the reaction was complete, filtered through a celite pad, and concentrated in vacuo. The crude product was dissolved in THF and 4 mL of 1N HCl was added dropwise. After 1 h reaction mixture was cooled to 0° C. and the solid precipitate was collected (380 mg, 40.0%). $^1$H NMR (DMSO) δ: 2.553 (3H, s), 3.832 (3H, s), 7.000 (1H, d), 7.089 (1H, s), 7.451 (1H, d), 8.100 (1H, d), 8.430 (1H, d), 9.220 (1H, s).

PREPARATIVE EXAMPLE 16

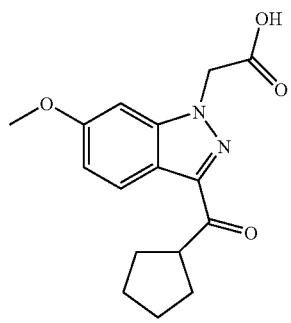

Step A:

To a solution of Intermediate 5 (500 mg, 2.048 mmol) and NaH (163 mg, 4.096 mmol, 60% dispersion in oil washed with hexane) in DMF (10 mL) was added ethyl bromoacetate (0.272 mL, 2.457 mmol). After 40 min the reaction was complete and quenched with H$_2$O. The reaction mixture was extracted with EtOAc and the combined organic layers were washed with H$_2$O, brine, dried over MgSO$_4$, and concentrated in vacuo. The material was used with no further purification (597 mg, 88% yield). $^1$H NMR (CDCl$_3$) δ: 1.295 (3H, t), 1.684 (2H, m), 1.792 (2H, m), 2.000 (4H, m), 3.904 (3H, s), 4.047 (1H, m), 4.284 (2H, q), 5.167 (2H, s), 6.680 (1H, s), 6.991 (1H, d), 8.270 (1H, d).

Step B:

To a solution of the intermediate from Step A dissolved in methanol (10 mL) was added 5N NaOH (3.6 mL). After 2 h the reaction was complete and the methanol was removed in vacuo. The resulting aqueous layer was extracted with ether, acidified to pH 2, diluted with EtOAc, washed with H$_2$O, dried over MgSO$_4$, and concentrated in vacuo. The crude product was used with no further purification (409 mg, 75% yield). $^1$H NMR (CD$_3$OD) δ: 1.696 (4H, m), 1.887 (2H, m), 1.980 (2H, m), 3.885 (3H, s), 4.074 (1H, m), 5.303 (2H, s), 6.943 (1H, d), 7.033 (1H, s), 8.105 (1H, d).

PREPARATIVE EXAMPLE 17

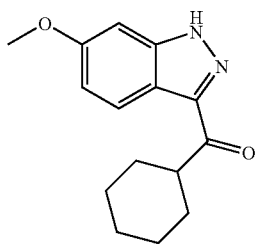

The desired compound was prepared by a procedure similar to the one described for Intermediate 5, but cyclohexyl magnesium bromide was used in place of cyclopentyl magnesium bromide. $^1$H NMR (CDCl$_3$) δ: 1.327 (1H, m), 1.479

(2H, m), 1.604 (2H, m), 1.781 (1H, m), 1.861 (2H, m), 2.000 (2H, m), 3.641 (1H, m), 3.902 (3H, s), 6.923 (1H, s), 7.008 (1H, d), 8.259 (1H, d).

PREPARATIVE EXAMPLE 18

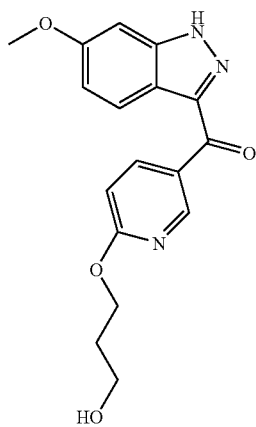

Step A:

To a solution of 5-iodo-2-chloropyridine (2.56 g, 10.78 mmol) in THF (10 mL) was added iPrMgBr dropwise at −78° C. The reaction stirred for 1 h before Intermediate 8 (1.71 g, 6.10 mmol) was added as a solution in THF (5 mL). After 2 h and the reaction was quenched with 1N NaOH and extracted with EtOAc. The combined organic layers were washed with brine, dried over MgSO$_4$, and concentrated in vacuo. To a solution of the crude product in toluene (50 mL) was added MnO$_2$ (2.173 g, 25.0 mmol) and the reaction mixture was heated to 130° C. After 1 h the reaction was complete, filtered through a celite pad, and concentrated in vacuo. The crude product was dissolved in THF (10 mL) and 4 mL of 1N HCl was added dropwise. The reaction stirred at RT until TLC analysis indicated completion. The reaction mixture was cooled to 0° C. and the solid precipitate was collected (1.131 g, 64%). $^1$H NMR (CD$_3$OD) δ: 3.900 (3H, s), 7.013 (1H, d), 7.062 (1H, s), 7.627 (1H, d), 8.672 (1H, d), 9.306 (1H, s).

Step B:

To a solution of the intermediate from Step A (275 mg, 1.02 mmol), DMAP (12 mg, 0.102 mmol), and TEA (0.169 mL, 1.22 mmol) in acetonitrile (10 mL) was added tert-butoxy-carbonyl anhydride (265 mg, 1.22 mmol). After 40 min the reaction was complete and quenched with H$_2$O. The reaction mixture was extracted with EtOAc and the combined organic layers were washed with H$_2$O, brine, dried over MgSO$_4$, and concentrated in vacuo to yield 3.14 mg of the desired product. $^1$H NMR (CDCl$_3$): δ 1.771 (9H, s), 3.967 (3H, s), 7.113 (1H, d), 7.513 (1H, d), 7.717 (1H, s), 8.291 (1H, d), 8.724 (1H, d), 9.487 (1H, s).

Step C:

500 mg (12.5 mmol) of NaH (60% dispersion in mineral oil) was washed 3× with hexane and dried under nitrogen. 1,3-propane-di-ol (5 mL) was added to the dry NaH and the reaction stirred for 20 min at 60° C. To the reaction mixture was added the intermediate from Step B (487 mg, 1.25 mmol) as a solution in THF (5 mL). The reaction continued to stir for 3 h at 60° C. Upon completion, the 1° F. was removed in vacuo, diluted with EtOAc, washed with H$_2$O, brine, dried over MgSO$_4$, and concentrated in vacuo. The crude material was dissolved in 10 mL of EtOAc and cooled to 0° C. HCl (g) was then bubbled until the solution was saturated. After 2 hours analysis via LCMS indicated that all of the starting material was consumed and the solid precipitate was collected. $^1$H NMR (DMSO): δ 1.862 (2H, m), 3.555 (2H, t), 3.822 (3H, s), 4.391 (2H, m), 6.965 (2H, m), 7.073 (1H, s), 8.088 (1H, d), 8.466 (1H, d), 9.090 (1H, s).

EXAMPLE 18

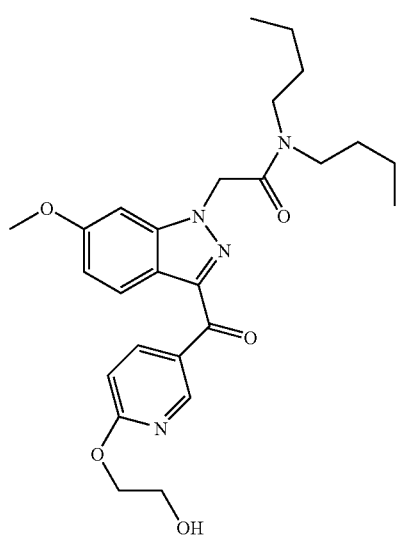

Step A:

To a solution of Preparative Example 6 (600 mg g, 2.08 mmol) and Cs$_2$CO$_3$ (2.028 g, 6.24 mmol) in DMF (14 mL) was added Preparative Example 5 (809 mg, 3.24 mmol). After 35 min the reaction was complete and poured into ice water. The solid precipitate was collected to yield 950 mg of the desired product (quantitative).

$^1$H NMR (CDCl$_3$) δ: 0.919 (3H, t), 0.975 (3H, t), 1.327 (4H, m), 1.596 (4H, m), 3.408 (4H, m), 3.926 (3H, s), 5.275 (2H, s), 6.864 (1H, s), 7.053 (1H, d), 7.491 (1H, d), 8.321 (1H, d), 8.563 (1H, d), 9.425 (1H, d).

Step B:

800 mg (20.0 mmol) of NaH (60% dispersion in mineral oil) was washed 3× with hexane and dried under nitrogen. Ethylene glycol (14 mL) was added to the dry NaH and the reaction stirred for 20 min at 50° C. To the reaction mixture was added the intermediate from the previous step (916 mg, 2.0 mmol) as a solution in THF (12 mL). The reaction was stirred over night at 50° C. The reaction mixture was poured into ice water and the solid precipitate was collected. The crude product was purified via silica gel chromatography to yield the desired product (688 mg, 71.1%).

$^1$H NMR (CDCl$_3$) δ: 0.903 (3H, m), 0.987 (3H, m), 1.372 (4H, m), 1.584 (4H, m), 3.405 (4H, m), 3.922 (3H, s), 4.028

(2H, m), 4.640 (2H, m), 5.288 (2H, s), 6.858 (1H, s), 6.953 (1H, d), 7.050 (1H, d), 8.302 (1H, d), 8.579 (1H, d), 9.360 (1H, s).

EXAMPLE 19

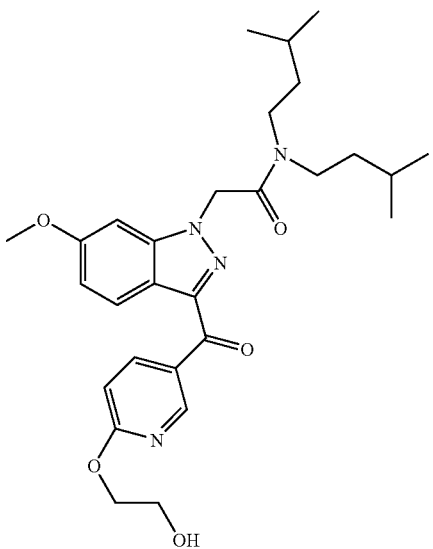

Step A:

This compound was prepared as described in Step A of Example 1 but Preparative Example 9 was used in place of Preparative Example 5.

$^1$H NMR (CDCl$_3$) δ: 0.857 (6H, d), 0.943 (6H, d), 1.380-1.604 (6H, m), 3.338 (4H, m), 3.834 (3H, s), 5.196 (2H, s), 6.748 (1H, s), 6.974 (1H, d), 7.400 (1H, d), 8.208 (1H, d), 8.503 (1H, d), 9.336 (1H, s).

Step B:

This compound was prepared as described in Step B of Example 18. Purified via SiO$_2$ preparatory plate (1:1 hexane/EtOAc).

$^1$H NMR (CDCl$_3$) δ: 0.909 (6H, d), 0.975 (6H, d), 1.503-1.624 (6H, m), 3.441 (4H, m), 3.925 (3H, s), 4.032 (2H, m), 4.610 (2H, m), 5.282 (2H, s), 6.863 (1H, s), 6.954 (1H, d), 7.054 (1H, d), 8.324 (1H, d), 8.585 (11H, d), 9.354 (1H, s).

EXAMPLE 20

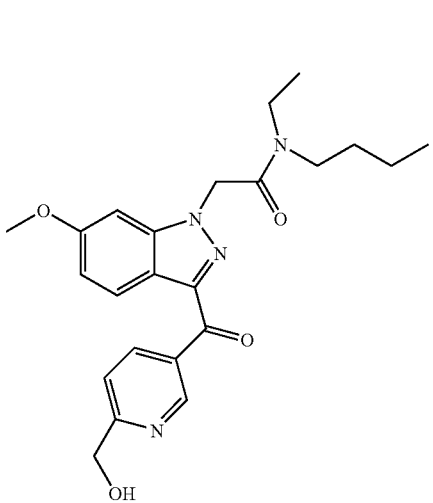

Using Preparative Example 10, this compound was prepared as described in Step A of Example 1 but Preparative Example 11 was used in place of Preparative Example 5. Purified via SiO$_2$ preparatory plate chromatography.

$^1$H NMR (CDCl$_3$) δ: 0.924 (3H, m), 1.158-1.440 (7H, m), 3.442 (4H, m), 3.932 (3H, s), 4.956 (2H, s), 5.310 (2H, s), 6.871 (1H, s), 7.081 (1H, d), 7.559 (1H, d), 8.314 (1H, d), 8.712 (1H, d), 9.673 (1H, s).

EXAMPLE 21

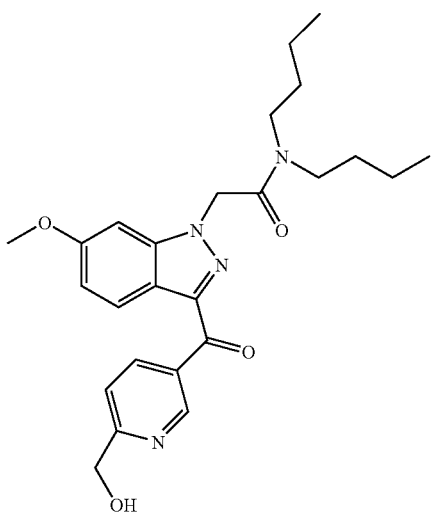

Using Preparative Example 10, this compound was prepared as described in Step A of Example 18. Purified via SiO$_2$ preparatory plate chromatography.

$^1$H NMR (CDCl$_3$) δ: 0.916 (3H, t), 0.965 (3H, t), 1.379 (4H, m), 1.589 (4H, m), 3.414 (4H, m), 3.925 (3H, s), 4.896 (2H, m), 5.285 (2H, s), 6.865 (1H, s), 7.045 (1H, d), 7.443 (1H, d), 8.311 (1H, d), 8.615 (1H, d), 9.578 (1H, s).

EXAMPLE 22

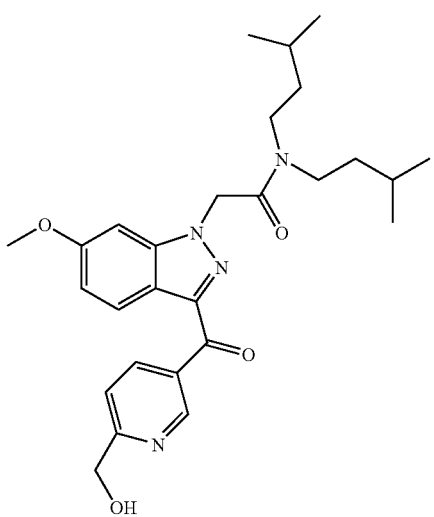

Using Preparative Example 10, this compound was prepared as described in Step A of Example 1 but Preparative Example 9 was used in place of Preparative Example 5. Purified via SiO₂ preparatory plate chromatography.

¹H NMR (CDCl₃) δ: 0.910 (6H, d), 0.992 (6H, d), 1.450-1.700 (6H, m), 3.411 (4H, m), 3.933 (3H, s), 4.973 (2H, s), 5.297 (2H, s), 6.847 (1H, s), 7.082 (1H, d), 7.568 (1H, bs), 8.332 (1H, d), 8.744 (1H, bs), 9.701 (1H, s).

EXAMPLE 23

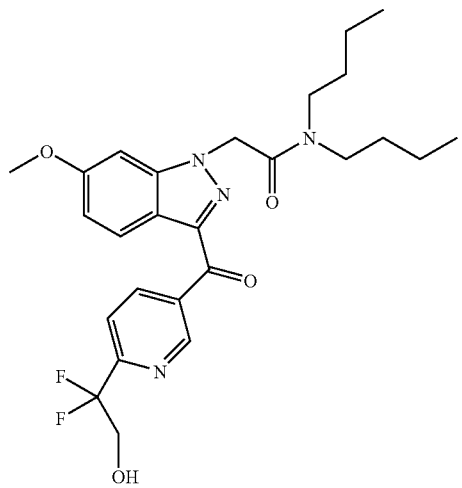

To Preparative Example 12 (21 mg, 0.053 mmol), HOBt (14.3 mg, 0.106 mmol), and EDC (30.3 mg, 0.159 mmol) was added NMP((1 mL) and DIPEA (0.027 mL, 0.159 mmol). After 10 minutes dibutyl amine (0.014 mL, 0.106 mmol) was added to the reaction and the mixture stirred overnight at room temperature. Upon completion the reaction was diluted with water and extracted with EtOAc. The combined organic layers were washed with 1N HCl, water, brine, dried over MgSO₄, and concentrated in vacuo. The final product was purified via reverse phase liquid chromatography (25-100% acetonitrile in H₂O). The product was purified via silica gel chromatography (EtOAc/hexane=1/1).

¹H NMR (CHCl₃): δ 9.55 (1H, d); 8.73 (1H, dd); 8.32 (1H, d); 7.88 (1H, d); 7.07 (1H, dd); 6.86 (1H, d); 5.29 (2H, s); 4.32 (2H, t); 3.93 (3H, s); 3.38 (4H, m); 1.60 (4H, m); 1.40-1.28 (4H, m); 0.97 (3H, t); 0.92 (3H, t). LC-MS (M+H)=503.7.

EXAMPLE 24

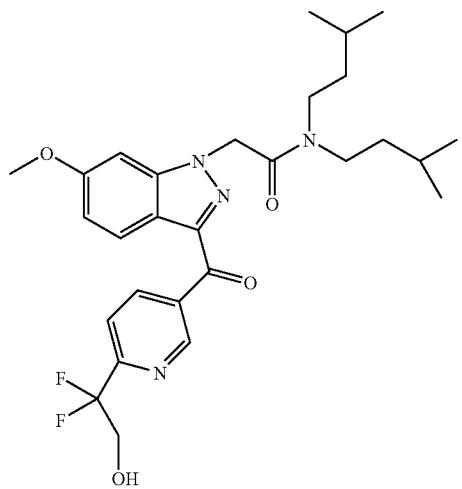

This compound was made as described in Example 23 but diisoamyl amine was used in place of dibutylamine. The product was purified via silica gel chromatography (EtOAc/hexane=1/1).

¹H NMR (CHCl₃): δ 9.55 (1H, d); 8.73 (1H, dd); 8.33 (1H; d); 7.88 (1H, d); 7.07 (1H, dd); 6.87 (1H, d); 5.27 (2H, s); 4.32 (2H, t); 3.94 (3H, s); 3.40 (4H, m); 1.67-1.43 (6H, m); 0.97 (6H, d); 0.92 (6H, d). LC-MS (M+H)=531.3

EXAMPLE 25

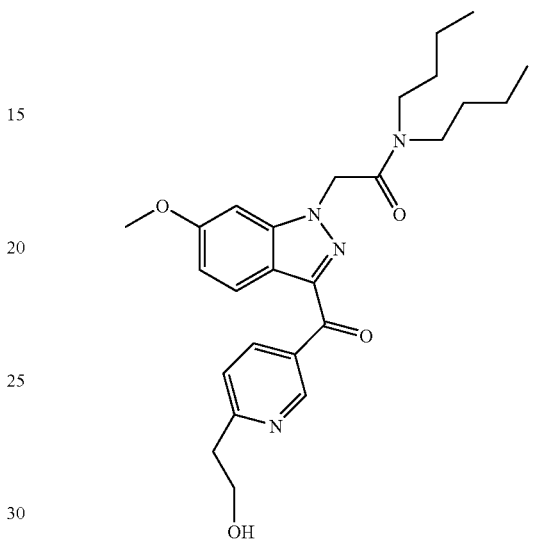

To a solution of Preparative Example 13 (150 mg) and Cs2CO3 (500 mg) in DMF was added Preparative Example 5 (150 mg). After reaction completed, the mixture was poured into ice/water to give precipitate. This compound was purified by silica gel (methylene chloride/ethyl acetate=1/1).

¹H NMR (CHCl₃): δ 9.57 (1H, d); 8.57 (1H, dd); 8.32 (1H, d); 7.39 (1H, d); 7.06 (1H, dd); 6.86 (1H, d); 5.30 (2H, s); 4.11 (2H, t); 3.93 (3H, s); 3.42 (2H, t); 3.38 (2H, t); 3.20 (2H, m); 1.57 (4H, m); 1.40-1.28 (4H, m); 0.98 (3H, t); 0.92 (3H, t). LC-MS (M+H)=467.4.

EXAMPLE 26

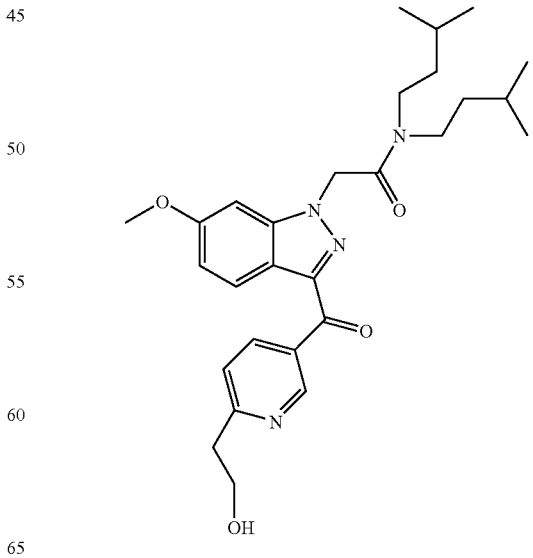

The desired compound was prepared by the procedure described in Example 25 using Preparative Example 9 instead of Preparative Example 5. This compound was purified by silica gel (hexanes/ethyl acetate=1/3).

¹H NMR (CHCl₃): δ 9.58 (1H, d); 8.58 (1H, dd); 8.32 (1H, d); 7.41 (1H, d); 7.06 (1H, dd); 6.86 (1H, d); 5.29 (2H, s); 4.11 (2H, t); 3.93 (3H, s); 3.40 (4H, m); 3.22 (2H, m); 1.74-1.40 (6H, m); 0.98 (6H, t); 0.92 (6H, t). LC-MS (M+H)=495.4.

Another method for the preparation of compounds for this invention is outlined in Scheme 3. Commercially available aniline 1 was converted to amide 2. The latter was cyclized based on a known method to give indole 3 (see K. Smith, G. A. El-Hiti, G. J. Pritchard, A. Hamilton J. Chem. Soc. Perkin Trans. 11999, 2299-2303). This indole was converted to indazole 4 via a modified procedure of P. Piozzi and M. Dubini (Gazz Chim Ital 1959, 89, 638). Subsequent conversion to the desired amides compounds 8 was similar to what has been described above.

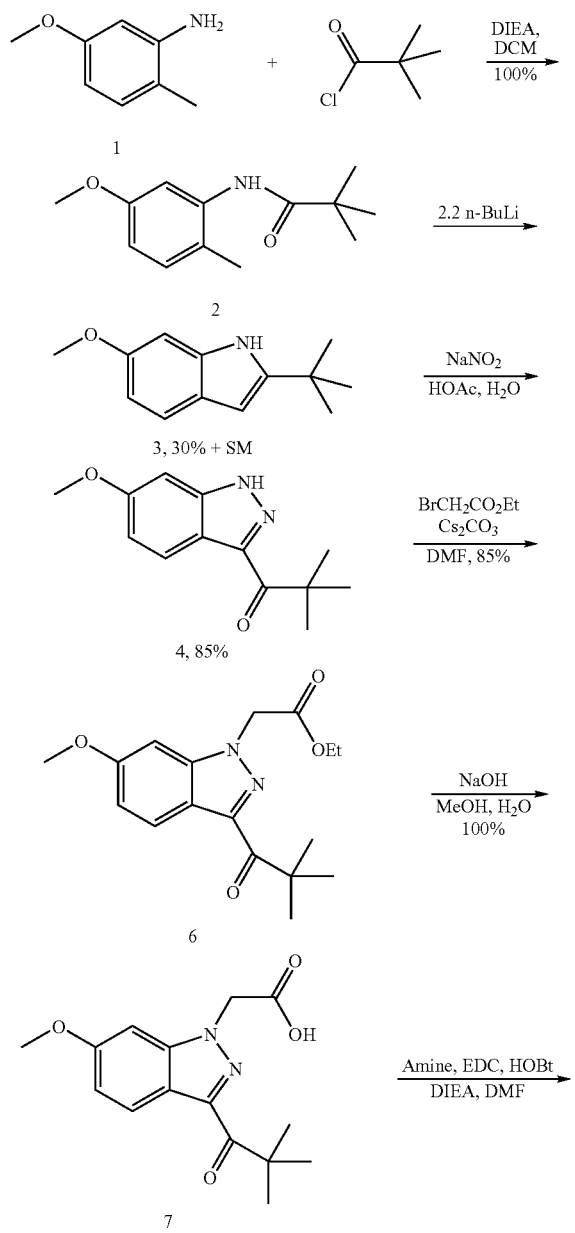

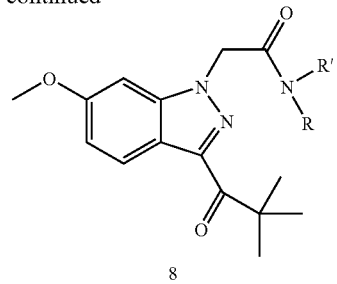

General Experimental Conditions: NMR spectra were recorded at room temperature on Varian Instruments referenced to residual solvent peak. LC-MS were measured on an Agilent HPLC and Micromass ZQ detector with electrospray ionization using a 2.0×50 mm X-Terra C18 column and 10-98% MeCN gradient over 3.75 minutes followed by 98% MeCN for 1 minute. The aqueous and MeCN eluents contained 0.06 and 0.05% (v/v) trifluoroacetic acid, respectively. Preparative HPLC separations were done using an YMC 20×150 mm 5 □ ProC18 column or a 9.4×250 mm SB-C18 Zorbax column.

EXAMPLE 27

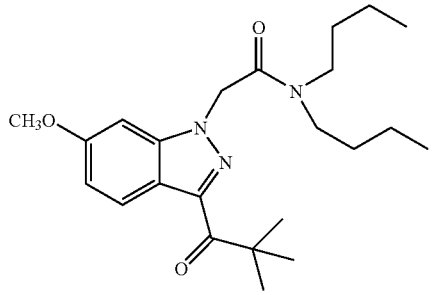

N,N-Dibutyl-2-[3-(2,2-dimethylpropanoyl)-6-methoxy-1H-indazol-1-yl]acetamide

Step A: N-(5-Methoxy-2-methylphenyl)-2,2-dimethylpropanamide To a solution of 10.44 g 2-methyl-5-methoxyaniline in 200 mL DCM was added 10.82 g DIEA followed by 9.64 g trimethylacetyl chloride with stir. After 40 hours, most solvent was removed under reduced pressure. The residue was diluted with ether and washed with 0.25 M HCl (2×), 5% NaHCO₃, and saturated brine, dried over anhydrous Na₂SO₄ and evaporated to give the title compound as light tan solid. ¹H NMR (CDCl₃, 500 MHz) δ 7.74 (d, J=2.5 Hz, 1H), 7.29 (br s, NH), 7.08 (d, J=8.5 Hz, 1H), 6.64 (dd, J=2.5 & 8.5 Hz, 1H), 3.82 (s, 3H), 2.22 (s, 3H), 1.37 (s, 9H). LC-MS: 2.97 min. (m/Z=222).

Step B: 2-tert-Butyl-6-methoxy-1H-indole

To a solution of 17.20 g N-(5-methoxy-2-methylphenyl)-2,2-dimethylpropanamide prepared in Step A above in 300 mL anhydrous THF under nitrogen in a −3° C. bath was added 62.2 mL 2.5 M n-BuLi in hexanes. After stirring for 1 hour, the cooling bath was removed. After four days, it was quenched by addition of saturated ammonium chloride solution and concentrated under reduced pressure to remove solvents. The residue was diluted with 1 N HCl and extracted with ether. The combine ether extract was washed with 5% NaHCO₃, and saturated brine, dried over anhydrous Na₂SO₄ and evaporated to give a crude product. It was purified by SGC with 10-25% EtOAc in hexanes to give title compound as yellowish solid followed by recovered starting material. $^1$H NMR (CDCl₃, 500 MHz) δ 7.85 (br s, 1NH), 7.42 (d, J=8.7 Hz, 1H), 6.87 (d, J=2.3 Hz, 1H), 6.77 (dd, J=2.3 & 8.4 Hz, 1H), 6.19 (d, J=2.2 Hz, 1H), 3.86 (s, 3H), 1.40 (s, 9H). LC-MS: 3.68 min. (m/Z=204.1).

Step C: 1-(6-Methoxy-1H-indazol-3-yl)-2,2-dimethylpropan-1-one

To a magnetically stirred solution of 0.203 g 2-tert-butyl-6-methoxy-1H-indole in 10 mL acetic acid and 0.5 mL water was added 0.138 g sodium nitrite solid. The reaction mixture was filtered to collect a yellowish solid. It was washed with 9:1 HOAc and water and dried to give the title compound. The filtrate and wash was allowed to stand at room temperature for about 2 weeks and evaporated under reduced pressure. The residue was dissolve in 1:1:1 mixture of HOAc, MeCN, and water and purified on RP-HPLC to give another crop of title compound. It can also be purified using SGC with 20-40% EtOAc in hexanes. This product has identical NMR and LC-MS as that prepared from 6-methoxy-3-cyano indazole. $^1$H NMR (CDCl₃, 500 MHz) δ 8.275 (d, J=8.9 Hz, 1H), 6.99 (dd, J=2.3 & 8.9 Hz, 1H), 6.90 (d, J=2.1 Hz, 1H), 3.90 (s, 3H), 1.52 (s, 9H). LC-MS: 3.49 min. (m/Z=215.1, 233.1, 190.1).

Step D: Ethyl [3-(2,2-dimethylpropanoyl)-6-methoxy-1H-indazol-1-yl]acetate

To a solution of 1.43 g (6-methoxy-1H-indazol-3-yl)-2,2-dimethylpropan-1-one from the Step C above in 45 mL anhydrous DMF was added 1.13 g ethyl bromoacetate and 2.41 g cesium carbonate. The mixture was stirred under nitrogen at room temperature for 2.5 days. It was diluted with ether and cold water with 15 mL 1 N HCl. The aqueous layer was separated and extracted with ether three times. The combined ether extract was washed with water (5×) and saturated brine, dried over anhydrous Na₂SO₄ and evaporated to give a crude product. It was purified by SGC with 20-40% EtOAc in hexanes to give title compound as solid. $^1$H NMR (CDCl₃, 500 MHz) δ 8.27 (d, J=8.9 Hz, 1H), 6.985 (dd, J=2.1 & 8.9 Hz, 1H), 6.68 (d, J=2.0 Hz, 1H), 5.15 (s, 2H), 4.27 (q, J=7.1 Hz, 2H), 3.90 (s, 3H), 1.50 (s, 9H), 1.28 (t, J=7.1 Hz, 3H). LC-MS: 3.93 min. (m/Z=319.3).

Step E: [3-(2,2-Dimethylpropanoyl)-6-methoxy-1H-indazol-1-yl]acetic acid

To a solution of 0.30 g ethyl [3-(2,2-dimethylpropanoyl)-6-methoxy-1H-indazol-1-yl]acetate from the Step D above in 20 mL MeOH and 2 mL water was added 0.50 mL of 5 N NaOH solution. After the solution was stirred at room temperature for 16 hours, the solvents were removed under reduced pressure. The residue was partitioned between cold water and EtOAc with 3 mL 1 N HCl. Separate the layers. Extract the aqueous layer with EtOAc (4×). The combined EtOAc extract was washed with saturated brine (2×), dried over anhydrous Na₂SO₄, and evaporated to give the title compound as yellowish solid. $^1$H NMR (CDCl₃, 500 MHz) δ 8.27 (d, J=8.9 Hz, 1H), 7.00 (dd, =2.1 & 8.9 Hz, 1H), 6.68 (d, =2.1 Hz, 1H), 5.21 (s, 2H), 3.90 (s, 3H), 1.50 (s, 9H). LC-MS: 3.40 min. (m/Z=245.1, 291.1).

Step F: N,N-Dibutyl-2-[3-(2,2-dimethylpropanoyl)-6-methoxy-1H-indazol-1-yl]acetamide To a solution of 28.3 mg [3-(2,2-dimethylpropanoyl)-6-methoxy-1H-indazol-1-yl]acetic acid from the Step E above in 1 mL DMF was added 23.0 mg HOBt, 19.4 mg dibutylamine, 38.3 mg EDC, and 45.2 mg DIEA in that order. The mixture was stirred at room temperature over night and purified by RP-HPLC using 65~100% MeCN gradient. The pure product fractions were pooled and lyophilized to give the title compound as white solid. LC-MS: 4.33 min. (m/Z=402.3, 424.3).

EXAMPLE 28

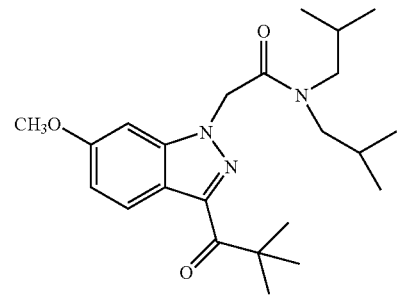

2-[3-(2,2-Dimethylpropanoyl)-6-methoxy-1H-indazol-1-yl]-N,N-diisobutylacetamide

To a solution of 28.3 mg [3-(2,2-dimethylpropanoyl)-6-methoxy-1H-indazol-1-yl]acetic acid in 1 mL DMF was added 23.0 mg HOBt, 19.4 mg diisobutylamine, 38.3 mg EDC, and 45.2 mg DIEA in that order. The mixture was stirred at room temperature over night and purified by RP-HPLC using 65-100% MeCN gradient. The pure product fractions were pooled and lyophilized to give the title compound as white solid. LC-MS: 4.29 min. (m/Z=402.3, 424.3).

EXAMPLE 29

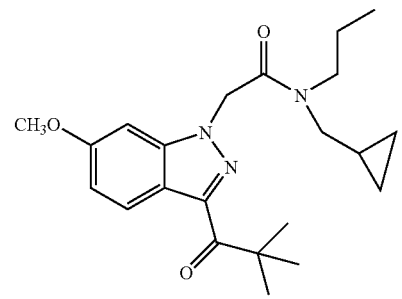

N-(Cyclopropylmethyl)-2-[3-(2,2-diethylpropanoyl)-6-methoxy-1H-indazol-1-yl]-N-propylacetamide To a solution of 28.3 mg [3-(2,2-dimethylpropanoyl)-6-methoxy-1H-indazol-1-yl]acetic acid in 1 mL DMF was added 23.0 mg HOBt, 17.0 mg N-propylcyclopropanemethylamine, 38.3 mg EDC, and 45.2 mg DIEA in that order. The mixture was stirred at room temperature over night and purified by RP-HPLC using 60-100% MeCN gradient. The pure product fractions were pooled and lyophilized to give the title compound as white solid. LC-MS: 4.07 min. (m/Z=386.3, 408.3).

EXAMPLE 30

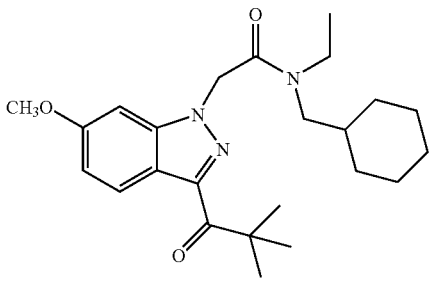

N-(Cyclohexylmethyl)-2-[3-(2,2-dimethylpropanoyl)-6-methoxy-1H-indazol-1-yl]-N-ethylacetamide To a solution of 28.3 mg [3-(2,2-dimethylpropanoyl)-6-methoxy-1H-indazol-1-yl]acetic acid in 1 mL DMF was added 23.0 mg HOBt, 19.1 mg N-ethylcyclohexylamine, 38.3 mg EDC, and 45.2 mg DIEA in that order. The mixture was stirred at room temperature over night and purified by RP-HPLC using 65-100% MeCN gradient. The pure product fractions were pooled and lyophilized to give the title compound as white solid. LC-MS: 4.20 min. (m/Z=318.2, 400.3, 422.2).

EXAMPLE 31

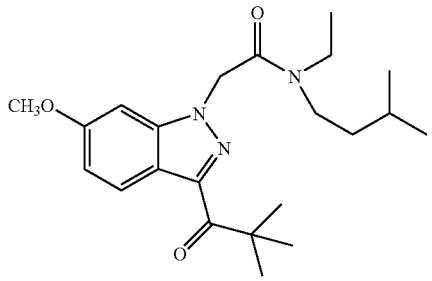

2-[3-(2,2-Dimethylpropanoyl)-6-methoxy-1H-indazol-1-yl]-N-ethyl-N-(3-methylbutyl)acetamide To a solution of 29.0 mg [3-(2,2-dimethylpropanoyl)-6-methoxy-1H-indazol-1-yl]acetic acid in 1 mL DMF was added 23.0 mg HOBt, 17.3 mg N-ethyl-iso-amylamine, 38.3 mg EDC, and 45.2 mg DIEA in that order. The mixture was stirred at room temperature over night and purified by RP-HPLC using 60-100% MeCN gradient. The pure product fractions were pooled and lyophilized to give the title compound. LC-MS: 4.16 min. (m/Z=388.3, 4.10.2).

EXAMPLE 32

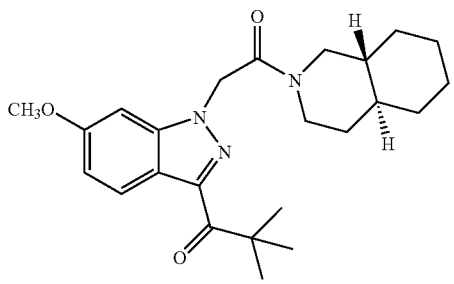

1-(6-methoxy-1-{2-[trans-octahydroisoquinolin-2(1H)-yl]-2-oxoethyl}-1H-indazol-3-yl)-2,2-dimethylpropan-1-one To a solution of 29.0 mg [3-(2,2-dimethylpropanoyl)-6-methoxy-1H-indazol-1-yl]acetic acid in 1 mL DMF was added 23.0 mg HOBt, 20.9 mg trans-decahydroisoquinoline, 38.3 mg EDC, and 45.2 mg DIEA in that order. The mixture was stirred at room temperature over night and purified by RP-HPLC using 65-100% MeCN gradient. The pure product fractions were pooled and lyophilized to give the title compound. LC-MS: 4.29 min. (m/Z=412.3, 434.3).

EXAMPLE 33

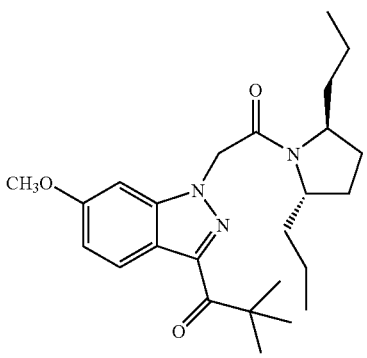

1-(1-{2-[Trans-2,5-dipropylpyrrolidin-1-yl]-2-oxoethyl}-6-methoxy-1H-indazol-3-yl)-2,2-dimethylpropan-1-one Step A: N,N'-Dimethoxy-N,N'-dimethylsuccinamide Dissolve 136.2 g of succinyl dichloride and 180.0 g N,O-dimethylhydroxylamine hydrochloride in 1.2 L dichloromethane and cool it in an ice bath. Add 305.9 g pyridine from an addition funnel with stir over 1.5 hours. Let the reaction mixture warm up to room temperature over night. Pour the reaction mixture into ice and water and separate the layers. Wash the organic layer with cold 2 N HCl (2×), water, 5% NaHCO$_3$ (2×), and saturated brine. Dry over anhydrous Na$_2$SO$_4$ and evaporate to give crude product. It was washed with 3:1 hexanes and dichloromethane and dried to give the title compound as a light tan solid $^1$H NMR (CDCl$_3$, 500 MHz) δ: 3.70 (s, 6H), 3.15 (s, 6H), 2.74 (s, 4H).

Step B: Decane-4,7-dione

Cool a suspension of 20.42 g N,N'-dimethoxy-N,N'-dimethylsuccinamide from the Step A above in 1 L anhydrous ether in an ice bath under nitrogen. Add 300 mL of 2 M propylmagnesium chloride in ether over 15 minutes with mechanical stir. Continue to stir the reaction mixture in the cooling bath for 2.25 hours. Quench the reaction by adding 30 mL ethanol in 50 mL ether over 30 minutes. Pour the resulting suspension into 1 L ice and water containing 75 mL concentrated HCl. Separate the layers, wash the organic layer with dilute HCl, 5% NaHCO$_3$ and saturated brine. Dry over anhydrous Na$_2$SO$_4$. Evaporate the clear yellowish solution to give the title compound as yellow solid. $^1$H NMR (CDCl$_3$, 500 MHz) δ: 2.69 (s, 4H), 2.46 (t, J=7.4 Hz, 4H), 1.60-1.67 (m, 4H), 0.935 (t, J=7.5 Hz, 6H).

Step C: Cis- and trans-1-benzyl-2,5-dipropylpyrrolidine

Dissolve 11.92 g-decane-4,7-dione from the Step B above in 4.62 g acetic acid and 100 mL methanol. Add 1.16 g potassium hydroxide pellets. Stir to dissolve the potassium hydroxide. Cool the reaction mixture in an ice acetone bath at −15° C. Add 7.50 g benzylamine followed immediately with 5.4 g sodium cyanoborohydride in several portions. Let the reaction mixture warm up to room temperature over two days. Add 45 mL 4 N HCl drop-wise and stir for 30 minutes. Evaporate the reaction mixture under reduced pressure to remove most of the solvents. Dilute the residue with water, filter off some white solid, and extract the aqueous layer with ether. This ether solution contained 2,5-dipropylpyrrole. Cool the aqueous layer with an ice bath and add solid sodium hydroxide in small portions with stir until pH ~13. Dissolve the white solid above in this mixture. Extract with ether several times. Wash the combined ether solution with saturated brine, dry over anhydrous Na$_2$SO$_4$ and evaporate to give the crude 1-benzyl-2,5-dipropylpyrrolidine. The cis and trans isomers were separated on silica gel (5-10% EtOAc in hexanes with 1% Et$_3$N). The fast eluting isomer was trans-1-benzyl-2,5-dipropylpyrrolidine. $^1$H NMR (CDCl$_3$, 500 MHz) δ7.38 (d, J=7.6 Hz, 2H), 7.29-7.33 (m, 2H), 7.21-7.24 (m, 1H), 3.83 (d, J=13.9 Hz, 1H), 3.66 (d, J=14.0 Hz, 1-1), 2.86 (br.s, 2H), 1.85-1.94 (m, 2H), 1.45-1.60 (m, 4H), 1.27-1.37 (m, 2H), 1.09-1.20 (m, 4H), 0.875 (t, J=7.2 Hz, 6H). The slower-eluting isomer was cis-1-benzyl-2,5-dipropylpyrrolidine. $^1$H NMR (CDCl$_3$, 500 MHz) δ7.29-7.35 (m, 4H), 7.24-7.26 (m, 1H), 3.77 (s, 2H), 2.53-2.58 (m, 2H), 1.77-1.84 (m, 2H), 1.52-1.58 (m, 2H), 1.27-1.44 (m, 4H), 1.13-1.25 (m, 4H), 0.865 (t, J=7.2 Hz, 6H).

Step D: Trans-2,5-dipropylpyrrolidine

Dissolve 1.56 g trans-1-benzyl-2,5-dipropylpyrrolidine from the Step C above in 100 mL methanol and add 4.01 g ammonium formate and 156 mg Pd(OH)$_2$/C. Let the reaction mixture stir under nitrogen over night. Filter the reaction mixture through Celite to remove the catalyst. Concentrate the filtrate under reduced pressure to give white solid residue. Suspend it in a small amount of water, add 5 ml 5 N NaOH solution, extract with ether several times, wash the combined ether solution with saturated brine, dry over anhydrous Na$_2$SO$_4$, and evaporate to give the title compound as yellow liquid. $^1$H NMR (CDCl$_3$, 500 MHz) δ3.11-3.16 (m, 2H), 1.91-1.98 (m, 2H), 1.26-1.50 (m, 10H), 0.93 (t, J=7.1 Hz, 6H). LC-MS: 1.89 min. (M+H=156.1).

Step E: 1-(1-{2-[Trans-2,5-dipropylpyrrolidin-1-yl]-2-oxoethyl}-6-methoxy-1H-indazol-3-yl)-2,2-dimethylpropan-1-one To a solution of 28.3 mg [3-(2,2-dimethylpropanoyl)-6-methoxy-1H-indazol-1-yl]acetic acid in 1 mL DMF was added 23.0 mg HOBt, 23.3 mg trans-2,5-dipropylpyrrolidine from the Step D above, 38.3 mg EDC, and 45.2 mg DIEA in that order. The mixture was stirred at room temperature over night and purified by RP-HPLC using 70-100% MeCN gradient. The pure product fractions were pooled and lyophilized to give the title compound as white solid. LC-MS: 4.48 min. (m/Z=428.4, 450.3).

EXAMPLE 34

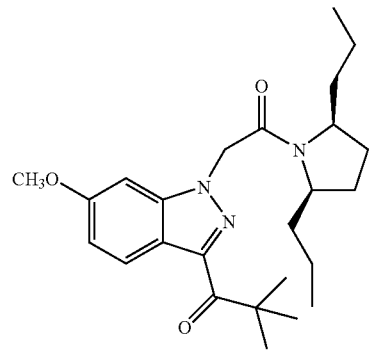

1-(1-{2-[Cis-2,5-dipropylpyrrolidin-1-yl]-2-oxoethyl}-6-methoxy-1H-indazol-3-yl)-2,2-dimethylpropan-1-one Step A: Cis-2,5-dipropylpyrrolidine The title compound was prepared from cis-1-benzyl-2,5-dipropylpyrrolidine. Dissolve 11.92 grams of decane-4,7-dione in 4.62 grams acetic acid and 100 mL methanol. Add 1.16 grams potassium hydroxide pellets. Stir to dissolve the potassium hydroxide. Cool the reaction mixture in an ice acetone bath at −15° C. Add 7.50 grams benzylamine followed immediately with 5.4 grams sodium cyanoborohydride in several portions. Let the reaction mixture warm up to room temperature over two days. Add 45 mL 4 N HCl drop-wise and stir for 30 minutes. Evaporate the reaction mixture under reduced pressure to remove most of the solvents. Dilute the residue with water, filter off some white solid, and extract the aqueous layer with ether. This ether solution contained 2,5-dipropylpyrrole. Cool the aqueous layer with an ice bath and add solid sodium hydroxide in small portions with stirring until pH-13. Dissolve the white solid above in this mixture. Extract with ether several times. Wash the combined ether solution with saturated brine, dry over anhydrous Na$_2$SO$_4$ and evaporate to give the crude 1-benzyl-2,5-dipropylpyrrolidine. The cis and trans isomers were separated on silica gel (5-10% EtOAc in hexanes with 1% Et$_3$N). The slow eluting isomer was cis-1-benzyl-2,5-dipropylpyrrolidine. $^1$H NMR (CDCl$_3$, 500 MHz) δ7.29-7.35 (m, 4H), 7.24-7.26 (m, 1H), 3.77 (s, 2H), 2.53-2.58 (m, 2H), 1.77-1.84 (m, 2H), 1.52-1.58 (m, 2H), 1.27-1.44 (m, 4H), 1.13-1.25 (m, 4H), 0.865 (t, J=7.2 Hz, 6H).

Step B: 1-(1-{2-[Cis-2,5-dipropylpyrrolidin-1-yl]-2-oxoethyl}-6-methoxy-1H-indazol-3-yl)-2,2-dimethylpropan-1-one To a solution of 28.3 mg [3-(2,2-dimethylpropanoyl)-6-methoxy-1H-indazol-1-yl]acetic acid from the Step E Example 44 in 1 mL DMF was added 23.0 mg HOBt, 23.3 mg cis-2,5-dipropylpyrrolidine from the Step A above, 38.3 mg EDC, and 45.2 mg DIEA in that order. The mixture was stirred at room temperature over night and purified by RP-HPLC using 70-100% MeCN gradient. The pure product fractions were pooled and lyophilized to give the title compound as white solid. LC-MS: 4.50 min. (m/Z=428.4, 450.3).

EXAMPLE 35

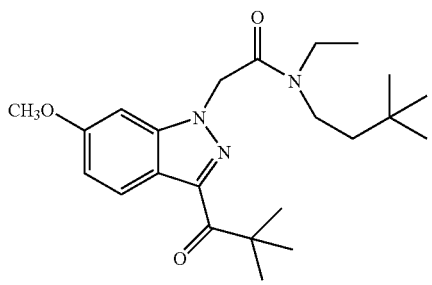

N-(3,3-Dimethylbutyl)-2-[3-(2,2-dimethylpropanoyl)-6-methoxy-1H-indazol-1-yl]-N-ethylacetamide Step A: N-Ethyl-3,3-dimethylbutan-1-amine hydrochloride The title compound was prepared from N-ethylbenzylamine and 3,3-dimethylbutyraldehye using sodium triacetoxyborohydride (Abdel-Magid, et al. J. Org. Chem. 1996, 61, 3849) followed by hydrogenolysis using Pd(OH)$_2$ and ammonium formate. $^1$H NMR (CD$_3$OD, 500 MHz) δ 3.07 (q, 7.1 Hz, 2H), 2.97-3.02 (m, 2H), 1.57-1.62 (m, 2H), 1.32 (t, 7.2 Hz, 3H), 0.98 (s, 9H).

Step B: N-(3,3-Dimethylbutyl)-2-[3-(2,2-dimethylpropanoyl)-6-methoxy-1H-indazol-1-yl]-N-ethylacetamide To a solution of 29.0 mg [3-(2,2-dimethylpropanoyl)-6-methoxy-1H-indazol-1-yl]acetic acid in 1 mL DMF was added 23.0 mg HOBt, 32.3 mg N-Ethyl-3,3-dimethylbutan-1-lamine hydrochloride from the Step A above, 38.3 mg EDC, and 45.2 mg DIEA in that order. The mixture was stirred at room temperature for four hours and heated at 45° C. over night and purified by RP-HPLC using 70-100% MeCN gradient. The pure product fractions were pooled and lyophilized to give the title compound. LC-MS: 4.29 min. (m/Z=402.4, 424.3).

EXAMPLE 36

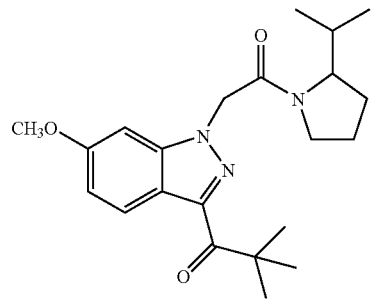

1-{1-[2-(2-Isopropylpyrrolidin-1-yl)-2-oxoethyl]-6-methoxy-1H-indazol-3-yl}-2,2-dimethylpropan-1-one To a solution of 29.0 mg [3-(2,2-dimethylpropanoyl)-6-methoxy-1H-indazol-1-yl]acetic acid 1 mL DMF was added 23.0 mg HOBt, 22.5 mg 2-isopropylpyrroline hydrochloride, 38.3 mg EDC, and 64.6 mg DIEA in that order. The mixture was stirred heated at 45° C. for two hours and purified by RP-HPLC using 60-100% MeCN gradient. The pure product fractions were pooled and lyophilized to give the title compound. LC-MS: 4.05 min. (m/Z=386.4, 408.3).

EXAMPLE 37

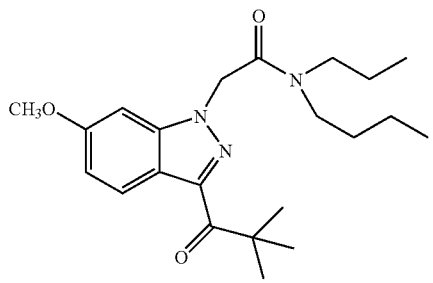

N-Butyl-2-[3-(2,2-dimethylpropanoyl)-6-methoxy-1H-indazol-1-yl]-N-propylacetamide Weigh 29.0 mg [3-(2,2-dimethylpropanoyl)-1H-indazol-1-yl]acetic acid, 23.0 mg HOBt, and 38.3 mg EDC into a 13×100 mm screw cap tube. Add 17.3 mg N-propylbutylamine followed by 1 mL DMF and 45.2 mg DIEA in that order. The mixture was stirred at 45° C. for two hours and purified by RP-HPLC using 65-100% MeCN gradient. The pure product fractions were pooled and lyophilized to give the title compound as white solid. LC-MS: 4.20 min. (m/Z=388.3, 410.3).

EXAMPLE 38

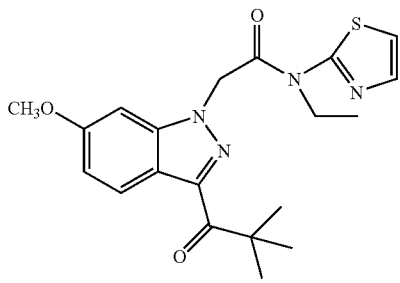

2-[3-(2,2-Dimethylpropanoyl)-6-methoxy-1H-indazol-1-yl]-N-ethyl-N-1,3-thiazol-2-ylacetamide Step A: N-Ethyl-1,3-thiazol-2-amine To a suspension of an N-ethylthiourea in ethanol was added 1,1-dimethoxy-2-bromoethane and concentrated HCl. The reaction mixture is heated at reflux to give title compound after chromatography on silica. $^1$H NMR (CDCl$_3$, 500 MHz) 87.14 (d, J=3.6 Hz, 1H), 6.51 (d, J=3.7 Hz, 1H), 5.47 (v br s, 1H), 3.34 (q, J=7.2 Hz, 2H), 1.32 (t, J=7.2 Hz, 3H).

Step B: 2-[3-(2,2-Dimethylpropanoyl)-6-methoxy-1H-indazol-1-yl]-N-ethyl-N-1,3-thiazol-2-ylacetamide Weigh 29.0 mg [3-(2,2-dimethylpropanoyl)-6-methoxy-1H-indazol-1-yl]acetic acid, 23.0 mg HOBt, and 38.3 mg EDC into a 13×100 mm screw cap tube. Add 19.2 mg N-ethyl-1,3-thiazol-2-amine followed by 1 mL DMF and 45.2 mg DIEA in that order. The mixture was stirred at 45° C. for two hours and purified by RP-HPLC using 50-90% MeCN gradient. The pure product fractions were pooled and lyophilized to give the title compound as a white solid. LC-MS: 3.96 min. (m/Z=423.2, 245.1, 273.1, 401.2).

EXAMPLE 39

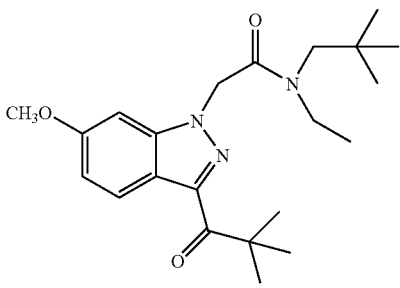

2-[3-(2,2-Dimethylpropanoyl)-6-methoxy-1H-indazol-1-yl]-N-(2,2-dimethylpropyl)-N-ethylacetamide Step A: N-ethyl-2,2-dimethylpropan-1-amine hydrochloride The title compound was prepared from N-ethylbenzylamine and triemthylacetaldehyde using sodium triacetoxyborohydride (Abdel-Magid, et al. J. Org. Chem. 1996, 61, 3849) followed by hydrogenolysis using Pd(OH)$_2$ and ammonium formate. $^1$H NMR (CD$_3$OD, 500 MHz) δ 3.095 (q, J=7.3 Hz, 2H), 2.85 (s, 2H), 1.35 (t, J=7.3 Hz, 3H), 1.07 (s, 9H).

Step B: 2-[3-(2,2-Dimethylpropanoyl)-6-methoxy-1H-indazol-1-yl]-N-(2,2-dimethylpropyl)-N-ethylacetamide Weigh 8.7 mg [3-(2,2-dimethylpropanoyl)-6-methoxy-1H-indazol-1-yl]acetic acid, 7.7 mg HOBt, and 11.5 mg EDC into a 13×100 mm screw cap tube. Add 7.6 mg N-ethyl-2,2-dimethylpropan-1-amine hydrochloride followed by 0.5 mL DMF and 13.6 mg DIEA in that order. The mixture was stirred at 44° C. over night and purified by RP-HPLC using 50-100% MeCN gradient. The pure product fractions were pooled and lyophilized to give the title compound as white solid. LC-MS: 4.04 min. (m/Z=388.3, 410.3).

EXAMPLE 40

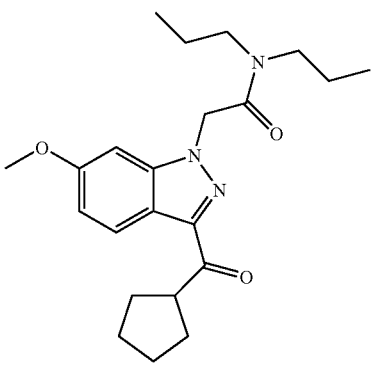

To Preparative Example 16 (45 mg, 0.148 mmol) dissolved in NMP (5 mL) was added HOBt (30.1 mg, 0.223 mmol), and EDC (56.5 mg, 0.296 mmol). After 10 min dipropyl amine (0.014 mL, 0.106 mmol) was added to the reaction and the mixture stirred overnight at RT. Upon completion the reaction was diluted with water and extracted with EtOAc. The combined organic layers were washed with 1N HCl, water, brine, dried over MgSO$_4$, and concentrated in vacuo. The final product was purified via SiO$_2$ preparatory plate chromatography. $^1$H NMR (CDCl$_3$) δ: 0.865 (3H, t), 0.980 (3H, m), 1.578 (4H, m), 1.607 (m, 2H), 1.795 (2H, m), 1.987 (4H, m), 3.318 (4H, m), 3.894 (3H, s), 4.045 (1H, m), 5.239 (2H, s), 6.848 (1H, s), 6.985 (1H, d), 8.219 (1H, d).

EXAMPLE 41

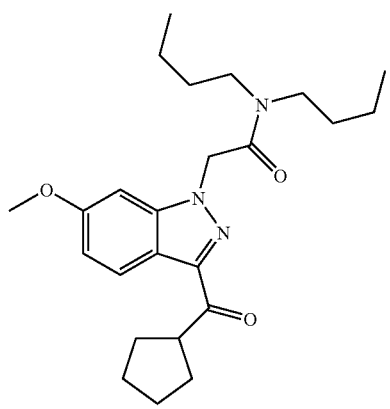

Using Preparative Example 16 (45 mg, 0.148 mmol) dissolved in NMP (5 mL) was added HOBt (30.1 mg, 0.223 mmol), and EDC (56.6 mg, 0.296 mmol). After 10 minutes dibutyl amine (0.014 mL, 0.106 mmol) was added to the reaction and the mixture stirred overnight at room temperature. Upon completion the reaction was diluted with water and extracted with EtOAc. The combined organic layers were washed with 1N HCl, water, brine, dried over MgSO$_4$, and concentrated in vacuo. The title compound was purified via SiO$_2$ preparatory plate chromatography. $^1$H NMR (CDCl$_3$) δ: 0.896 (3H, m), 0.979 (3H, m), 1.269-1.395 (4H, m), 1.551 (4H, m), 1.688 (2H, m), 1.797 (2H, m), 1.985 (4H, m), 3346 (4H, m), 3.897 (3H, s), 4.045 (1H, m), 5.228 (2H, s), 6.850 (1H, s), 6.986 (1H, d), 8.238 (1H, d).

EXAMPLE 42

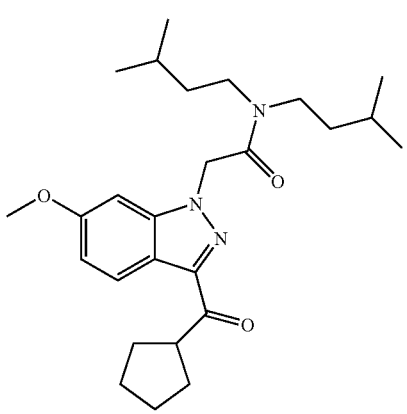

Using Preparative Example 16, this compound was prepared as described in Example 41 but diisoamyl amine was used in place of dipropyl amine. The title compound was purified via SiO$_2$ preparatory plate chromatography. $^1$H NMR (CDCl$_3$) δ: 0.902 (6H, d), 0.915 (6H, d), 1.426 (4H, m), 1.475-1.684 (4H, m), 1.795 (2H, m), 1.982 (4H, m), 3.411 (4H, m), 3.891 (3H, s), 4.045 (1H, m), 5.210 (2H, s), 6.849 (1H, s), 6.985 (1H, d), 8.236 (1H, d).

EXAMPLE 43

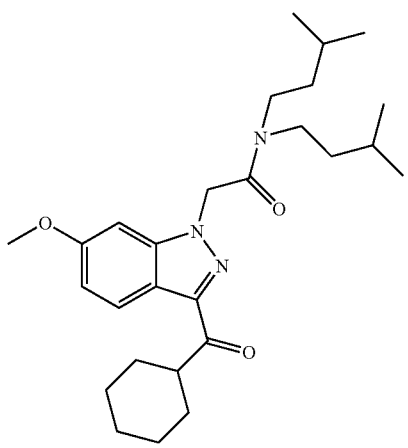

To a solution of Preparative Example 17 (30 mg, 0.116 mmol) and Cs$_2$CO$_3$ (88 mg, 0.348 mmol) in DMF (2 mL) was added Preparative Example 9 (51 mg, 0.232 mmol). After 30 min the reaction was complete and diluted with EtOAc and H$_2$O. The aqueous layer was extracted with EtOAc and the combined organic layers were washed with H$_2$O, brine, dried over MgSO$_4$, and concentrated to an oil. The crude residue was purified via column chromatography. $^1$H NMR (CDCl$_3$) δ: 0.900 (6H, d), 1.001 (6H, d), 1.292 (12H, m), 1.842 (2H, d), 1.986 (2H, d), 3.414 (4H, m), 3.623 (1H, m), 3.894 (3H, s), 5.209 (2H, s), 6.857 (1H, s), 6.975 (1H, d), 8.225 (1H, d).

EXAMPLE 44

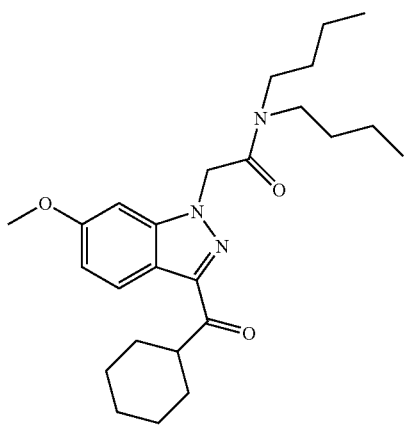

Using Preparative Example 17, this compound was prepared as described in Example 43 but Preparative Example 5 was used in place of Preparative Example 9. The title compound was purified via SiO$_2$ preparatory plate chromatography. $^1$H NMR (CDCl$_3$) δ: 0.897 (3H, t), 0.992 (3H, t), 1.284-

1.745 (14H, m), 1.870 (2H, d), 1.986 (2H, d), 3.363 (4H, m), 3.622 (1H, m), 3.886 (3H, s), 5.229 (2H, s), 6.850 (1H, s), 6.982 (1H, d), 8.227 (1H, d).
EXAMPLE 45
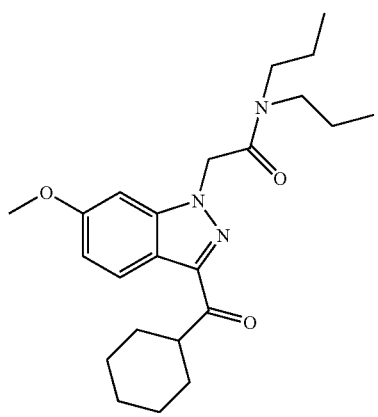
Using Preparative Example 17, this compound was prepared as described in Example 43 but Preparative Example 8 was used in place of Preparative Example 9. The title compound was purified via $SiO_2$ preparatory plate chromatography. $^1$H NMR (CDCl$_3$) δ: 0.875 (3H, t), 0.991 (3H, t), 1.318 (8H, m), 1.744 (2H, m), 1.875 (2H, d), 1.992 (2H, d), 3.374 (4H, m), 3.625 (1H, m), 3.890 (3H, s), 5.239 (2H, s), 6.847 (1H, s), 6.981 (1H, d), 8.225 (1H, d).
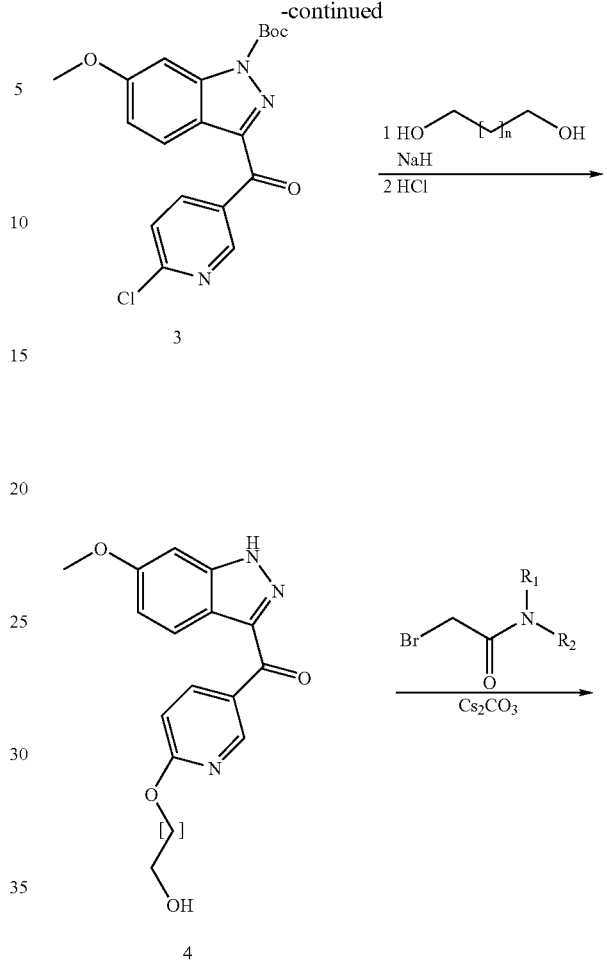
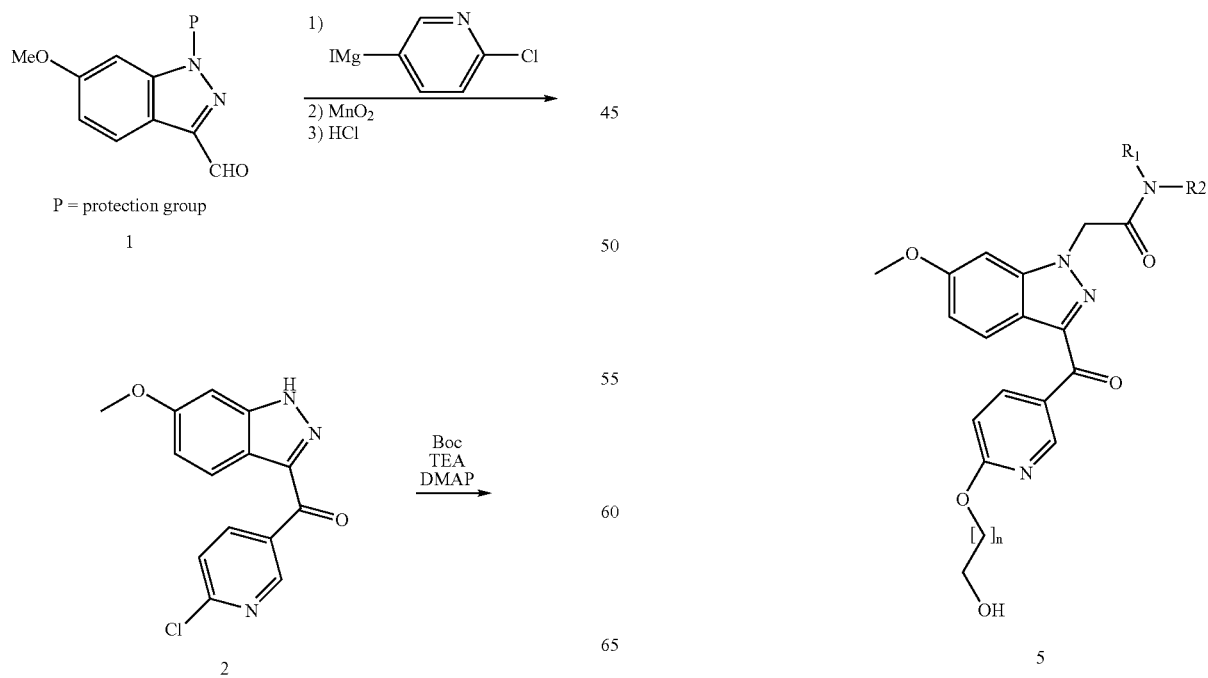

EXAMPLE 46

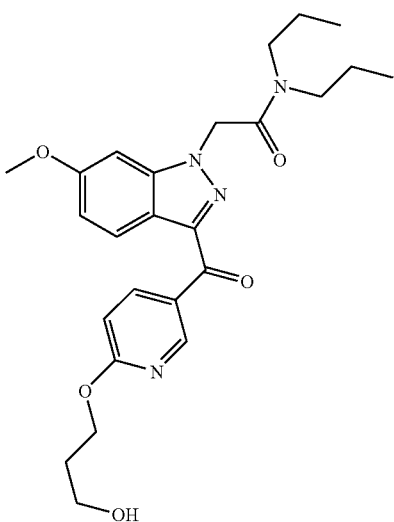

To a solution of Preparative Example 18 (50 mg, 0.152 mmol) and Cs$_2$CO$_3$ (148 mg, 0.456 mmol) in DMF (2 mL) was added Preparative Example 8 (84.2 mg, 0.304 mmol). After 30 min the reaction was complete and diluted with EtOAc and H$_2$O. The aqueous layer was extracted with EtOAc and the combined organic layers were washed with H$_2$O, brine, dried over MgSO$_4$, and concentrated to an oil. The crude residue was purified via column chromatography.

$^1$H NMR (CDCl$_3$) δ: 0.876 (3H, t), 0.991 (3H, t), 1.623 (4H, m), 2.073 (2H, m), 3.330 (2H, t), 3.3419 (2H, t), 3.771 (2H, t), 3.916 (3H, s), 4.666 (2H, t), 5.295 (2H, s), 6.862 (2H, m), 7.039 (1H, d), 8.285 (1H, d), 8.542 (1H, d), 9.354 (1H, s).

EXAMPLE 47

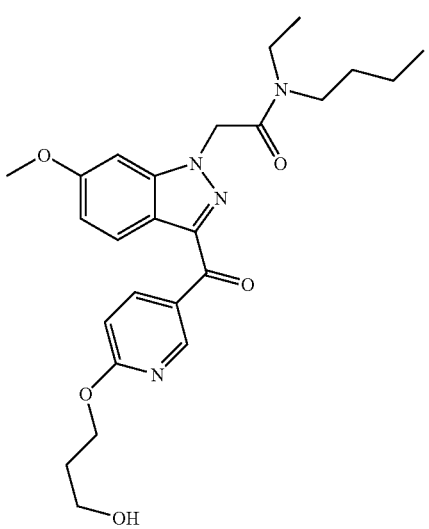

Using Preparative Example 18, this compound was prepared as described in Example 45 but Preparative Example 5 was used in place of Preparative Example 8. The title compound was purified via SiO$_2$ preparatory plate chromatography. $^1$H NMR (CDCl$_3$) δ: 0.895 (3H, m), 1.166 (3H, m), 1.347 (2H, m), 1.533 (2H, m), 2.031 (2H, m), 3.435 (4H, m), 3.755 (2H, m), 3.903 (3H, s), 4.626 (2H, m), 5.265 (2H, s), 6.853 (2H, m), 7.025 (1H, d), 8.034 (1H, m), 8.508 (1H, m), 9.325 (1H, s).

EXAMPLE 48

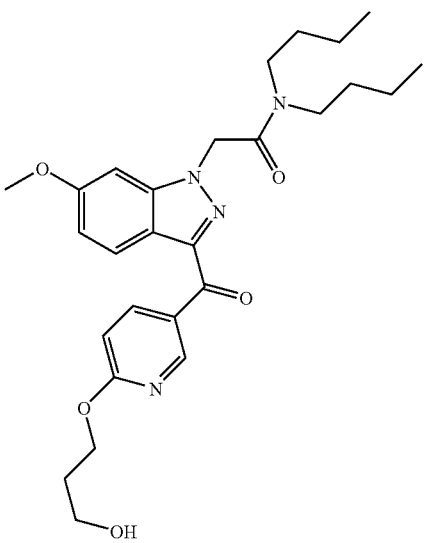

Using Preparative Example 18, this compound was prepared as described in Example 45 but Preparative Example 5 was used in place of Preparative Example 8. The title compound was purified via SiO$_2$ preparatory plate chromatography. $^1$H NMR (CDCl$_3$) δ: 0.896 (3H, t), 0.976 (3H, t), 1.361 (4H, m), 1.557 (4H, m), 2.066 (2H, m), 3.414 (4H, m), 3.777 (2H, m), 3.912 (3H, s), 4.652 (2H, m), 5.277 (2H, s), 6.862 (2H, m), 7.019 (1H, d), 8.312 (1H, d), 8.547 (1H, d), 9.336 (1H, s).

EXAMPLE 49

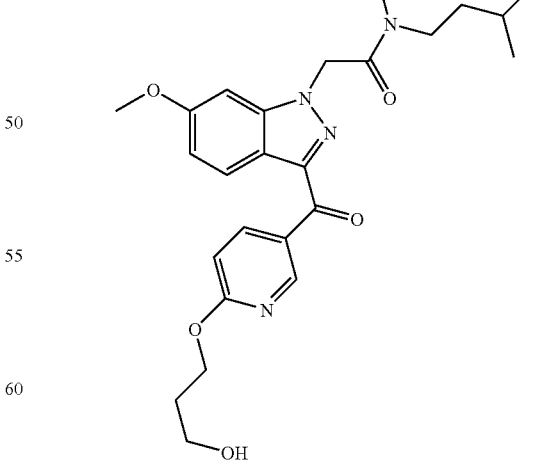

Using Preparative Example 18, this compound was prepared as described in Example 45 but Preparative Example 9 was used in place of Preparative Example 8. The title compound was purified via SiO$_2$ preparatory plate chromatography. $^1$H NMR (CDCl$_3$) δ: 0.905 (6H, d), 0.973 (6H, d), 1.440-1.652 (6H, m), 2.057 (2H, m), 3.433 (4H, m), 3.769 (2H, m), 3.919 (3H, s), 4.656 (2H, m), 5.270 (2H, s), 6.865 (2H, m), 7.019 (1H, d), 8.318 (1H, d), 8.552 (1H, d), 9.343 (1H, s).

Functional Assays

A. Maxi-K Channel

The identification of inhibitors of the Maxi-K channel can be accomplished using Aurora Biosciences technology, and is based on the ability of expressed Maxi-K channels to set cellular resting potential after transient transfection of both α and β subunits of the channel in TsA-201 cells. In the absence of inhibitors, cells display a hyperpolarized membrane potential, negative inside, close to $E_K$ (−80 mV) which is a consequence of the activity of the Maxi-K channel. Blockade of the Maxi-K channel will cause cell depolarization. Changes in membrane potential can be determined with voltage-sensitive fluorescence resonance energy transfer (RET) dye pairs that use two components, a donor coumarin (CC$_2$DMPE) and an acceptor oxanol (DiSBAC$_2$(3)). Oxanol is a lipophilic anion and distributes across the membrane according to membrane potential. Under normal conditions, when the inside of the cell is negative with respect to the outside, oxanol is accumulated at the outer leaflet of the membrane and excitation of coumarin will cause FRET to occur. Conditions that lead to membrane depolarization will cause the oxanol to redistribute to the inside of the cell, and, as a consequence, to a decrease in FRET. Thus, the ratio change (donor/acceptor) increases after membrane depolarization.

Transient transfection of the Maxi-K channel in TsA-201 cells can be carried out as previously described (Hanner et al. (1998) J. Biol. Chem. 273, 16289-16296) using FUGENE6™ as the transfection reagent. Twenty four hours after transfection, cells are collected in Ca$^{2+}$—Mg$^{2+}$-free Dulbecco's phosphate-buffered saline (D-PBS), subjected to centrifugation, plated onto 96-well poly-d-lysine coated plates at a density of 60,000 cells/well, and incubated overnight. The cells are then washed 1× with D-PBS, and loaded with 100 μl of 4 μM CC$_2$DMPE-0.02% pluronic-127 in D-PBS. Cells are incubated at room temperature for 30 min in the dark. Afterwards, cells are washed 2× with D-PBS and loaded with 100 μl of 60 μM DiSBAC$_2$(3) in (mM): 140 NaCl, 0.1 KCl, 2 CaCl$_2$, 1 MgCl$_2$, 20 Hepes-NaOH, pH 7.4, 10 glucose. Test compounds are diluted into this solution, and added at the same time. Cells are incubated at room temperature for 30 min in the dark.

Plates are loaded into a voltage/ion probe reader (VIPR) instrument, and the fluorescence emission of both CC$_2$DMPE and DiSBAC$_2$(3) are recorded for 10 sec. At this point, 100 μl of high-potassium solution (mM): 140 KCl, 2 CaCl$_2$, 1 MgCl$_2$, 20 Hepes-KOH, pH 7.4, 10 glucose are added and the fluorescence emission of both dyes recorded for an additional 10 sec. The ratio CC$_2$DMPE/DiSBAC$_2$(3), before addition of high-potassium solution equals 1. In the absence of any inhibitor, the ratio after addition of high-potassium solution varies between 1.65-2.0. When the Maxi-K channel has been completely inhibited by either a known standard or test compound, this ratio remains at 1. It is possible, therefore, to titrate the activity of a Maxi-K channel inhibitor by monitoring the concentration-dependent change in the fluorescence ratio.

The compounds of this invention were found to cause concentration-dependent inhibition of the fluorescence ratio with IC$_{50}$'s in the range of less than 20 μM.

B. Electrophysiological Assays of Compound Effects on High-Conductance Calcium-Activated Potassium Channels Human Non-Pigmented Ciliary Epithelial Cells The activity of high-conductance calcium-activated potassium (maxi-K) channels in human non-pigmented ciliary epithelial cells was determined using electrophysiological methods. Currents through maxi-K channels were recorded in the inside-out configuration of the patch clamp technique, where the pipette solution faces the extracellular side of the channel and the bath solution faces the intracellular side. Excised patches contained one to about fifty maxi-K channels. Maxi-K channels were identified by their large single channel conductance (250-300 pS), and by sensitivity of channel gating to membrane potential and intracellular calcium concentration. Membrane currents were recorded using standard electrophysiological techniques. Glass pipettes (Garner 7052) were pulled in two stages with a Kopf puller (model 750), and electrode resistance was 1-3 megohms when filled with saline. Membrane currents were recorded with EPC9 (HEKA Instruments) or Axopatch 1D (Axon Instruments) amplifiers, and digital conversion was done with ITC-16 interfaces (Instrutech Corp). Pipettes were filled with (mM); 150 KCl, 10 Hepes, 1 MgCl$_2$, 0.01 CaCl$_2$, 3.65 KOH, pH 7.20. The bath (intracellular) solution was identical, except, in some cases, calcium was removed, 1 mM EGTA was added and 20 mM KCl was replaced with 20 mM KF to eliminate calcium to test for calcium sensitivity of channel gating. Drugs were applied to the intracellular side of the channel by bath perfusion.

Human non-pigmented ciliary epithelial cells were grown in tissue culture as described (Martin-Vasallo, P., Ghosh, S., and Coca-Prados, M., 1989, J. Cell. Physiol. 141, 243-252), and plated onto glass cover slips prior to use. High resistance seals (>1 Gohm) were formed between the pipette and cell surface, and inside out patches were excised. Maxi-K channels in the patch were identified by their gating properties; channel open probability increased in response to membrane depolarization and elevated intracellular calcium. In patches used for pharmacological analysis, removing intracellular calcium eliminated voltage-gated currents. Maxi-K currents were measured after depolarizing voltage steps or ramps that caused channel opening.

The compounds of this invention were applied to the intracellular side of the channel in appropriate concentrations (0.001 to 10 μM). The compounds reduced channel open probability, and this effect was reversed upon washout of compounds from the experimental chamber. The IC50 for block of maxi-K channels under these conditions for the compounds of this invention ranged from about less than 20 μM.

What is claimed is:

1. A compound of the structural formula I:

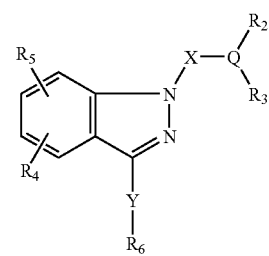

Formula I or a pharmaceutically acceptable salt, enantiamer, diastereomer or mixture thereof:
wherein,
R represents hydrogen, or $C_{1-6}$ alkyl;
X represents —$(CHR_7)_pCO$—;
Y represents —$CO(CH_2)_n$—;
Q represents N;
$R_w$ represents H, $C_{1-6}$ alkyl, —$C(O)C_{1-6}$ alkyl, —$C(O)OC_{1-6}$ alkyl, —$SO_2N(R)_2$, —$SO_2C_{1-6}$ alkyl, —$SO_2C_{6-10}$ aryl, $NO_2$, CN or —$CON(R)_2$;
$R_2$ represents hydrogen, $C_{1-10}$ alkyl, —$(CH_2)_nC_{3-8}$ cycloalkyl, said alkyl, optionally substituted with 1-3 groups selected from $R^a$;
$R_3$ represents hydrogen, $C_{1-10}$ alkyl, —$(CH_2)_nC_{3-8}$ cycloalkyl, said alkyl, optionally substituted with 1-3 groups of $R^a$;
$R_4$ and $R_5$ independently represent hydrogen, $C_{1-6}$ alkoxy, OH, $C_{1-6}$ alkyl, $SO_qC_{1-6}$ alkyl, $COC_{1-6}$ alkyl, COOR, $SO_3H$, —$O(CH_2)_nN(R)_2$, —$O(CH_2)_nCO_2R$, $CF_3$, $OCF_3$, —$N(R)_2$, nitro, cyano, $C_{1-6}$ alkylamino, or halogen;
$R_6$ represents hydrogen, $C_{1-10}$ alkyl, —$(CH_2)_nC_{6-10}$ aryl, $NR_cR_d$, —$NR(CH_2)_nC_{6-10}$ aryl, —$N((CH_2)_nC_{6-10}$ aryl$)_2$, —$(CH_2)_nC_{3-10}$ heterocyclyl, —$NR(CH_2)_nC_{3-10}$ heterocyclyl, —$N((CH_2)_nC_{3-10}$ heterocyclyl$)_2$, $(C_{6-10}$ aryl)O—, —$(CH_2)_nC_{3-8}$ cycloalkyl, —COOR, —$C(O)CO_2R$, said aryl, heterocyclyl and alkyl optionally substituted with 1-3 groups selected from $R^a$, wherein the $R^a$(s) can be attached to any carbon atom or heteroatom selected from N and S;
$R_c$ and $R_d$ independently represent H, C1-6 alkyl, $C_{2-6}$ alkenyl, $C_{1-6}$ alkylSR, —$(CH_2)_nO(CH_2)_mOR$, —$(CH_2)_nC_{1-6}$ alkoxy, —$(CH_2)_nC_{3-8}$ cycloalkyl;
or $R_c$ and $R_d$ taken together with the intervening N atom form a 4-10 membered heterocyclic carbon ring optionally interrupted by 1-2 atoms of O,S,C(O) or NR, and optionally having 1-4 double bonds, and optionally substituted by 1-3 groups selected from $R^a$;
$R_7$ represents hydrogen, $C_{1-6}$ alkyl, —$(CH_2)_nCOOR$ or —$(CH_2)_nN(R)_2$,
$R_8$ represents —$(CH_2)_nC_{3-8}$ cycloalkyl, —$(CH_2)$n 3-10 heterocyclyl, $C_{1-6}$ alkoxy or $(CH_2)_nC_{6-10}$ aryl said heterocyclyl, or aryl optionally substituted with 1-3 groups selected from $R^a$;
$R^a$ represents F, Cl, Br, I, $CF_3$, $N(R)_2$, $NO_2$, CN, —O—, —$COR_8$, -$CONHR_8$, —$CON(R_8)_2$, —$O(CH_2)_nCOOR$, —$NH(CH_2)_nOR$, —COOR, —$OCF_3$, $CF_2CH_2OR$, —NHCOR, —$SO_2R$, —$SO_2NR_2$, —SR, $(C_1$-$C_6$ alkyl)O—, —$(CH_2)_nO(CH_2)_mOR$, —$O(CH_2)_nO(CH_2)_mOR$, —$(CH_2)_nC_{1-6}$ alkoxy, (aryl)O—, —$(CH_2)_nOH$, $(C_1$-$C_6$ alkyl)$S(O)_m$—, $H_2N$—C(NH)—, $(C_1C_6$alkyl)$C(O)$—, $(C_1$-$C_6$ alkyl)OC(O)NH—, —$(C_1$-$C_6$ alkyl)$NR_w(CH_2)_n$ $C_{3-10}$ heterocyclyl-$R_w$, —$(C_1$-$C_6$ alkyl)$O(CH_2)_nC_{3-10}$ heterocyclyl-$R_w$, —$(C_1$-$C_6$ alkyl)$S(CH_2)_nC_{3-10}$heterocyclyl-$R_w$, —$(C_1$-$C_6$ alkyl)—$C_{3-10}$ heterocyclyl-$R_w$, —$(CH_2)$n-$Z^1$—$C(=Z^2)N(R)_2$, —$(C_{2-6}$ alkenyl)$NR_w(CH_2)_nC_{3-10}$ heterocyclyl-$R_w$, —$(C_{2-6}$ alkenyl)$O(CH_2)_nC_{3-10}$ heterocyclyl-$R_w$, —$(C_{2-6}$ alkenyl)$S(CH_2)_nC_{3-10}$ heterocycly-$R_w$, —$(C_{2-6}$ alkenyl)—$C_{3-10}$ heterocycly-$R_w$, —$(C_{2-6}$ alkenyl)—$Z^1$—$C(=Z_2)N(R)_2$, —$(CH_2)_nSO_2R$, —$(CH_2)_nSO_3H$, —$C_{3-10}$ cycloalkyl, $C_{6-10}$ aryl, $C_{3-10}$ heterocyclyl, $C_{2-6}$ alkenyl, and $C_1$-$C_{10}$ alkyl, said alkyl, alkenyl, alkoxy, heterocyclyl and aryl optionally substituted with 1-3 groups selected from $C_1$-$C_6$ alkyl, halogen, CN, $NO_2$, —$(CH_2)_n$ OH, $CON(R)_2$ and COOR;
$Z^1$ and $Z_2$ independently represents $NR_w$, O, $CH_2$, or S;
m is 0-3;
n is 0-3;
p is 0-3 and
q is 0-2.

2. A compound according to claim 1 wherein $R_6$ is $(CH_2)_n$ $C_{6-10}$ aryl, $(CH_2)_nC_{3-10}$ heterocyclyl, $NR_cR_d$ or $(CH_2)_nC_{3-8}$ cycloalkyl, said aryl, heterocyclyl and alkyl optionally substituted with 1 to 3 groups of $R^a$, and $R_4$ and $R_5$ independently represent hydrogen, $C_{1-6}$ alkoxy, OH, $C_{1-6}$ alkyl.

3. A compound of Table 1 through 4 which is

TABLE 1

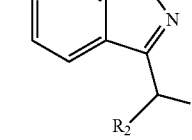

| R1 | R2 | R3 |
|---|---|---|
| H | Phenyl |  |
| H | Phenyl | 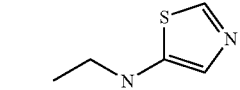 |
| H | Phenyl |  |
| H | Phenyl | 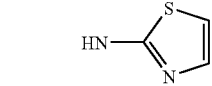 |
| H | Phenyl |  |
| H | Phenyl |  |
| H | Phenyl | 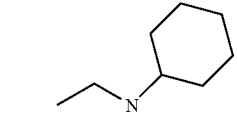 |
| OMe | Phenyl |  |
| OMe | Phenyl |  |
| OMe | Phenyl |  |

TABLE 1-continued
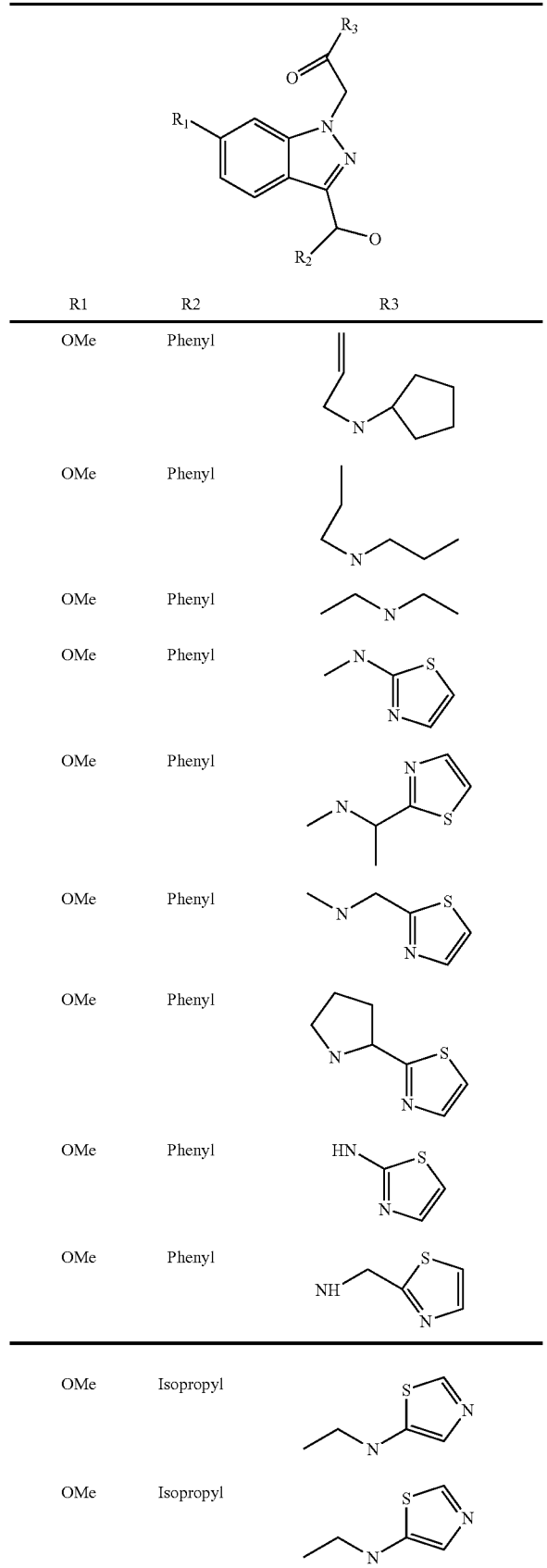
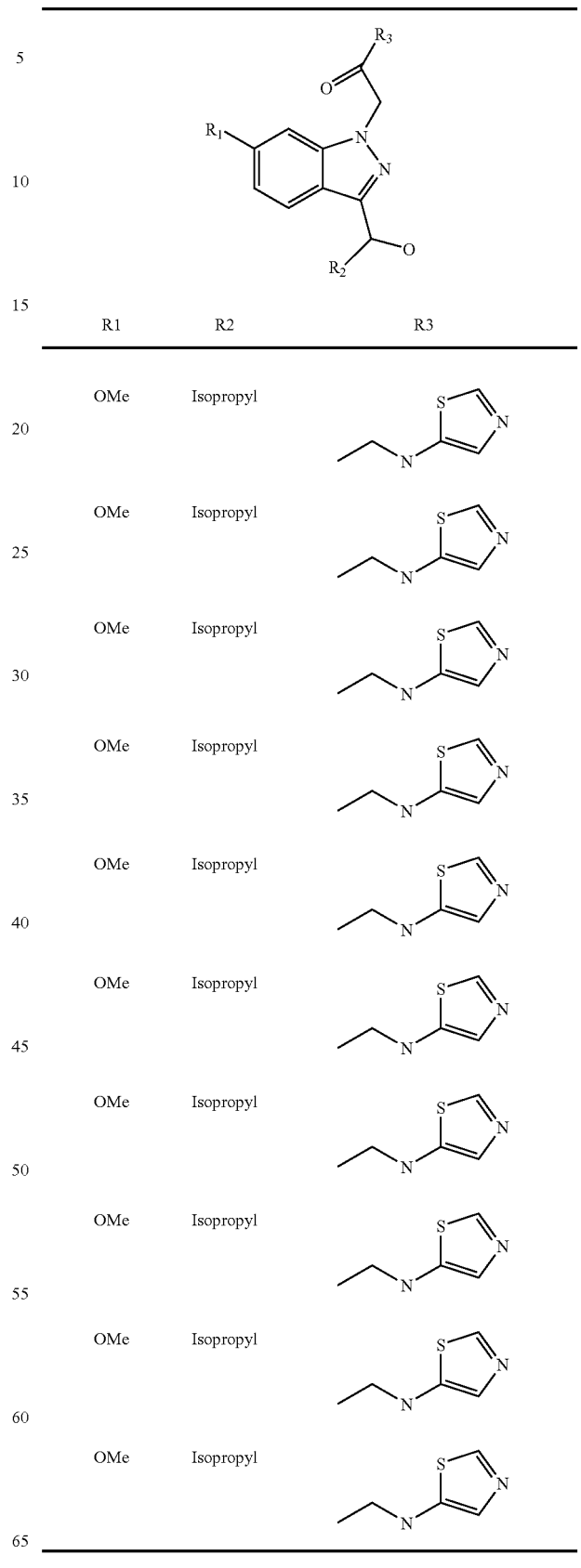

TABLE 2
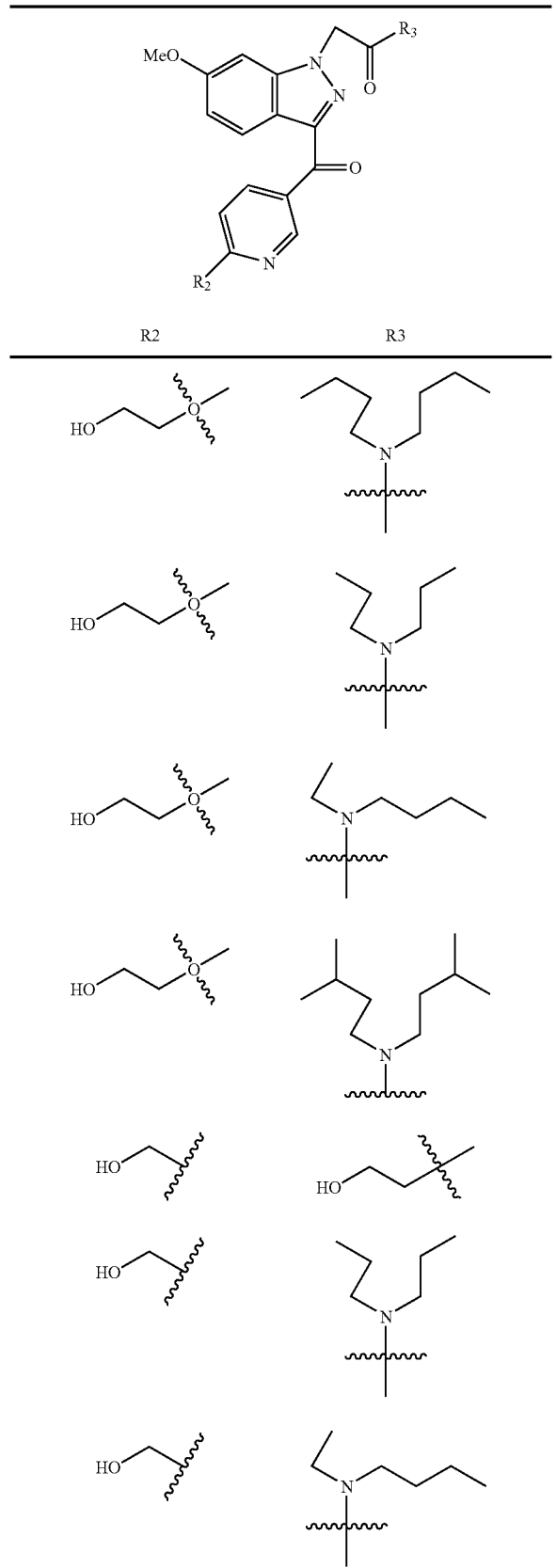
TABLE 2-continued
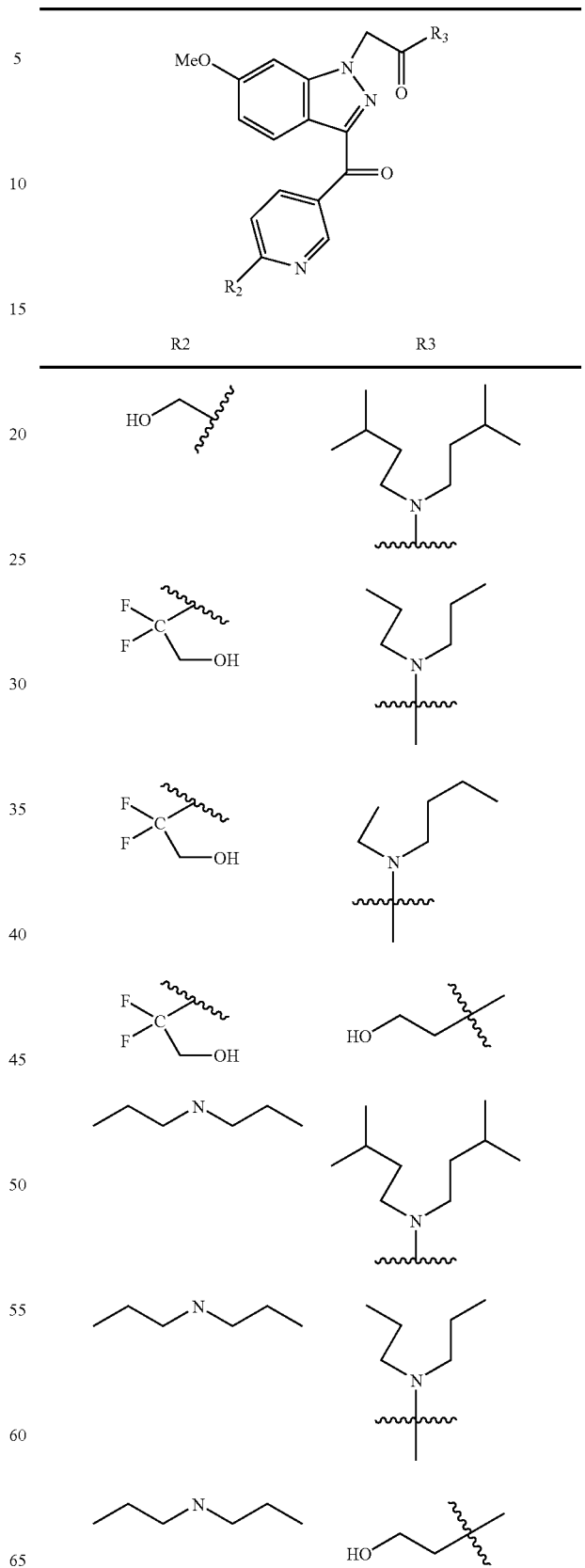

TABLE 2-continued
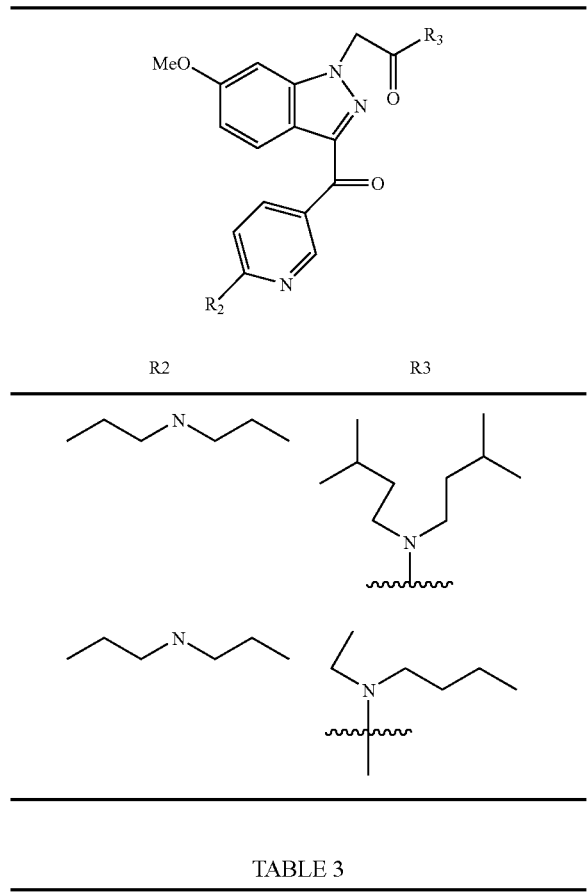
TABLE 3
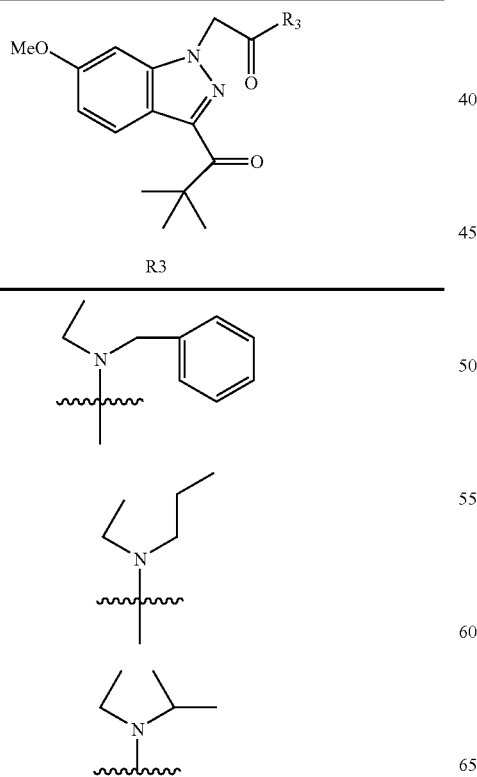
TABLE 3-continued
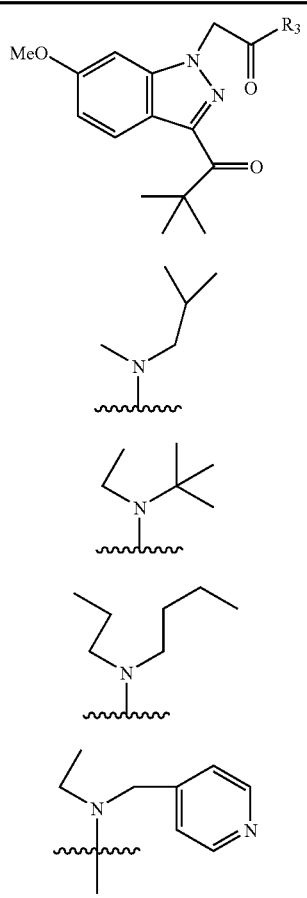

TABLE 3-continued
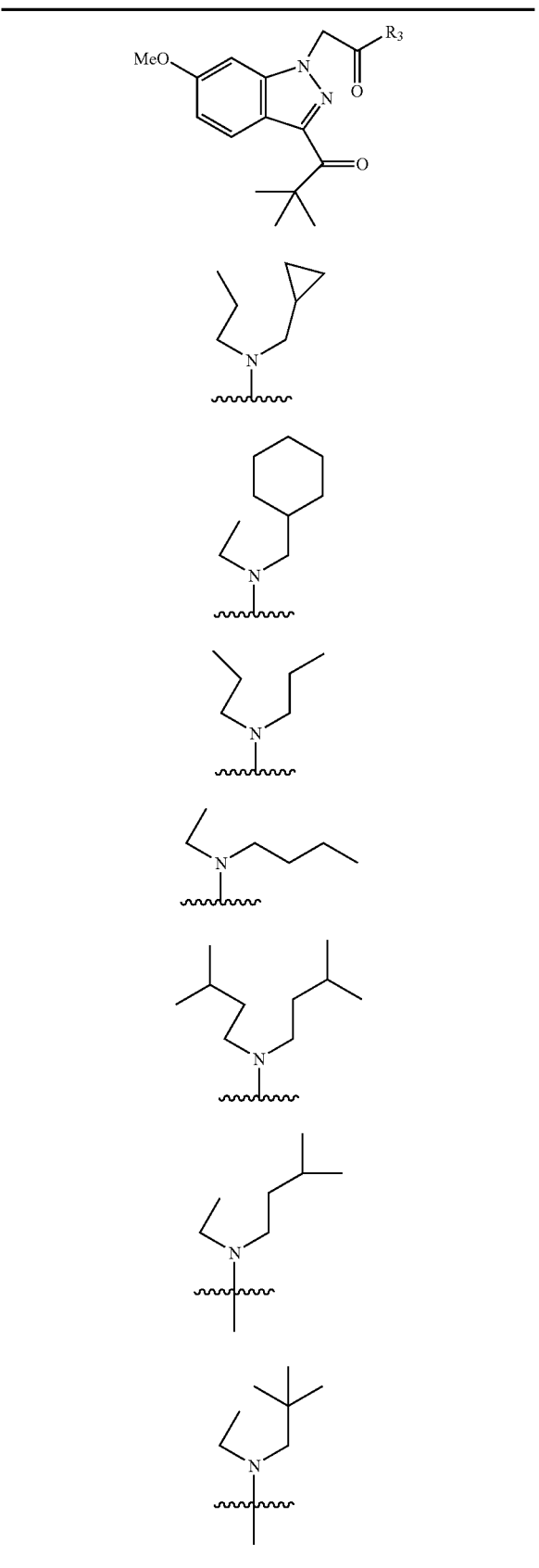
TABLE 3-continued
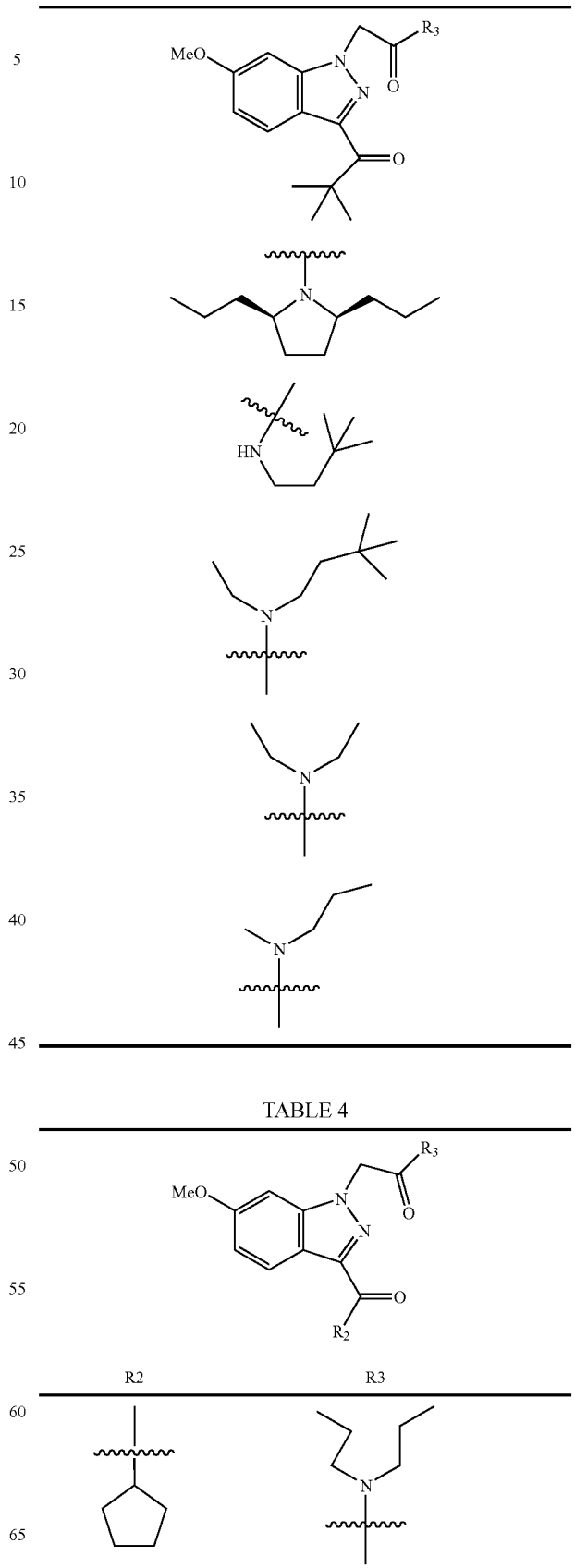
TABLE 4

TABLE 4-continued
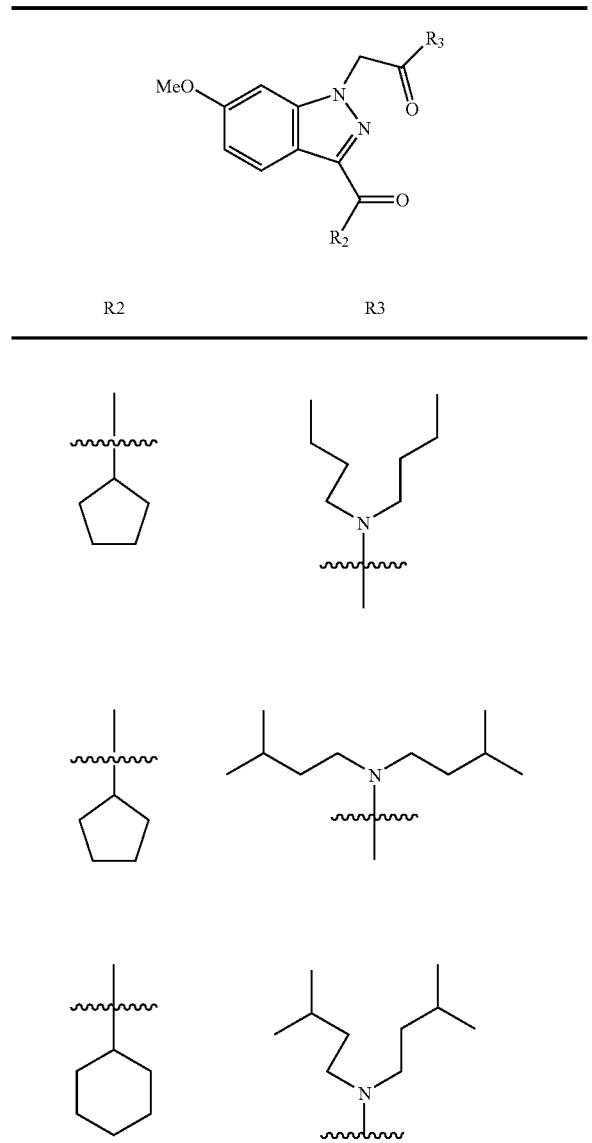
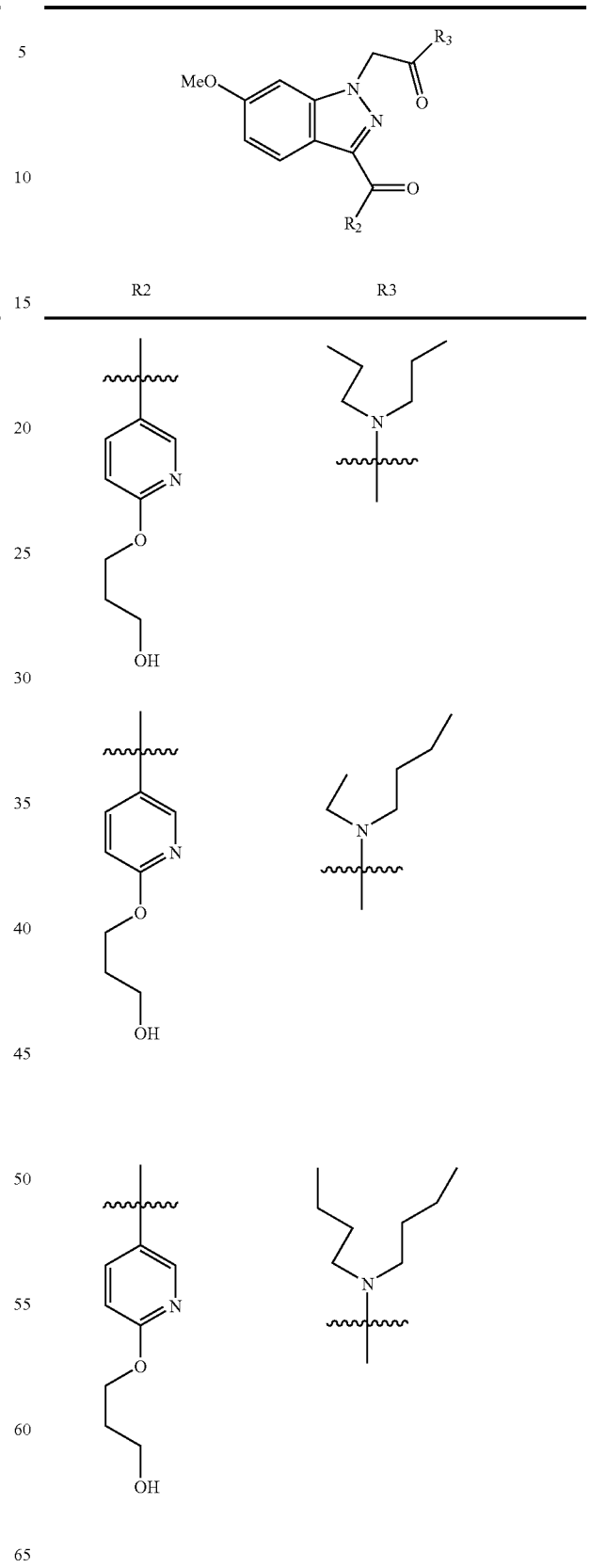

TABLE 4-continued

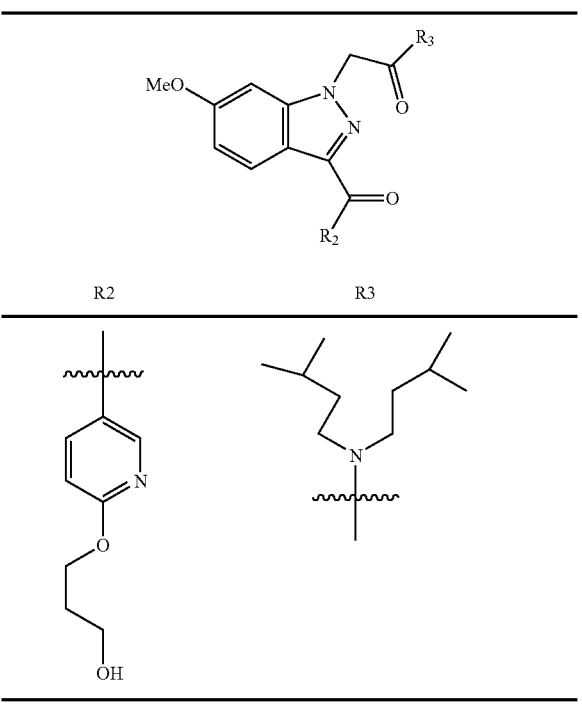

| R2 | R3 |
|---|---| or pharmaceutically acceptable salt, enantiomer, diastereomer or mixture thereof.

4. A composition comprising a compound of formula I of claim 1 and a pharmaceutically acceptable carrier.

5. The composition according to claim 4 wherein the compound of formula I is applied as a topical formulation, said topical formulation administered as a solution or suspension and optionally containing xanthan gum or gellan gum.

6. A composition according to claim 4 wherein an active ingredient belonging to the group consisting of: beta-adrenergic blocking agent, parasympatho-mimetic agent, sympathomimetic agent, carbonic anhydrase inhibitor, EP4 agonist, a prostaglandin or derivative thereat hypotensive lipid, neuroprotectant, and/or 5-HT2 receptor agonist is optionally added.

7. A composition according to claim 6 wherein the beta-adrenergic blocking agent is timolol, betaxolol, levobetaxolol, carteolol, or levobunolol; the parasympathomimctic agent is pilocarpine; the sympathomimetic agent is epinephrine, brimonidine, apraclonidine, clonidine, or para-aminoclonidine, the carbonic anhydrase inhibitor is dorzolamide, acetazolamide, metazolamide or brinzolamide; the prostaglandin is latanoprost, travaprost or unoprostone , the hypotensive lipid is an bimatoprost, the neuroprotectant is eliprodil, R-eliprodil or memantine; and the 5-HT2 receptor agonist is 1-(2-aminopropyl)-3-methyl-1H-imdazol-6-ol fumarate or 2-(3-chloro-6-methoxy-indazol- 1-yl)- I-methyl -ethylamine.

* * * * *